US010961288B2

(12) United States Patent
Scholler et al.

(10) Patent No.: US 10,961,288 B2
(45) Date of Patent: *Mar. 30, 2021

(54) ISOLATED B7-H4 SPECIFIC COMPOSITIONS AND METHODS OF USE THEREOF

(71) Applicant: THE TRUSTEES OF THE UNIVERSITY OF PENNSYLVANIA, Philadelphia, PA (US)

(72) Inventors: Nathalie Scholler, Mountain View, CA (US); Denarda Dangaj, Vaud (CH); Aizhi Zhao, Wallingford, PA (US); Daniel J. Powell, Bala Cynwyd, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/293,241

(22) Filed: Mar. 5, 2019

(65) Prior Publication Data

US 2020/0024314 A1    Jan. 23, 2020

Related U.S. Application Data

(60) Division of application No. 15/009,082, filed on Jan. 28, 2016, now Pat. No. 10,259,849, which is a division of application No. 14/181,931, filed on Feb. 17, 2014, now Pat. No. 9,279,008, which is a continuation of application No. PCT/US2012/063546, filed on Nov. 5, 2012.

(60) Provisional application No. 61/555,406, filed on Nov. 3, 2011.

(51) Int. Cl.
| | |
|---|---|
| *A61K 39/395* | (2006.01) |
| *C07K 16/28* | (2006.01) |
| *A61P 35/00* | (2006.01) |
| *C07K 14/47* | (2006.01) |
| *G01N 33/574* | (2006.01) |
| *G01N 33/68* | (2006.01) |
| *C07K 14/705* | (2006.01) |
| *C07K 16/18* | (2006.01) |

(52) U.S. Cl.
CPC ........ *C07K 14/47* (2013.01); *C07K 14/70532* (2013.01); *C07K 16/18* (2013.01); *C07K 16/2827* (2013.01); *G01N 33/574* (2013.01); *G01N 33/57492* (2013.01); *G01N 33/6863* (2013.01); *C07K 2317/54* (2013.01); *C07K 2317/55* (2013.01); *C07K 2317/622* (2013.01); *C07K 2317/76* (2013.01); *G01N 2333/70532* (2013.01)

(58) Field of Classification Search
None
See application file for complete search history.

(56) References Cited

U.S. PATENT DOCUMENTS

| | | |
|---|---|---|
| 4,444,887 A | 4/1984 | Hoffmann |
| 4,694,778 A | 9/1987 | Learn et al. |
| 4,716,111 A | 12/1987 | Osband et al. |
| 4,816,567 A | 3/1989 | Cabilly et al. |
| 5,199,942 A | 4/1993 | Gillis et al. |
| 5,225,539 A | 7/1993 | Winter |
| 5,229,275 A | 7/1993 | Goroff et al. |
| 5,350,674 A | 9/1994 | Boenisch et al. |
| 5,413,923 A | 5/1995 | Kucherlapati et al. |
| 5,530,101 A | 6/1996 | Queen et al. |
| 5,545,806 A | 8/1996 | Lonberg et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,573,905 A | 11/1996 | Lerner et al. |
| 5,585,089 A | 12/1996 | Queen et al. |
| 5,585,362 A | 12/1996 | Wilson et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,766,886 A | 6/1998 | Studnicka et al. |
| 5,814,318 A | 9/1998 | Lonberg et al. |
| 5,858,358 A | 1/1999 | June et al. |
| 5,883,223 A | 3/1999 | Gray |
| 5,939,598 A | 8/1999 | Kucherlapati et al. |
| 6,120,766 A | 9/2000 | Hale et al. |
| 6,326,193 B1 | 12/2001 | Liu et al. |
| 6,331,415 B1 | 12/2001 | Cabilly et al. |
| 6,352,694 B1 | 3/2002 | June et al. |
| 6,407,213 B1 | 6/2002 | Carter et al. |
| 6,534,055 B1 | 3/2003 | June et al. |
| 6,548,640 B1 | 4/2003 | Winter |
| 6,692,964 B1 | 2/2004 | June et al. |
| 6,797,514 B2 | 9/2004 | Berenson et al. |

(Continued)

FOREIGN PATENT DOCUMENTS

| | | |
|---|---|---|
| EP | 239400 A2 | 9/1987 |
| EP | 519596 A1 | 12/1992 |

(Continued)

OTHER PUBLICATIONS

Greenwald et al. 2005 Annu. Rev. Immunol. 23: 515-548.*
Yi et al. 2009 Immunological Reviews vol. 229: 145-151.*
He et al. 2011 Clinical and Developmental Immunology, vol. 2011, Article ID 695834, 8 pages.*
European Search Report for European Patent Application No. 12846241.3 dated Jul. 15, 2015.
International Search Report for PCT/US12/63546, dated Feb. 4, 2013.
Allavena , et al., "Immunology in the clinic review series; focus on cancer: tumour-associated macrophages: undisputed starts of the inflammatory tumour microenvironment", Clinical and Experimental Immunology 167, 2012, 195-205.

(Continued)

*Primary Examiner* — Ilia I Ouspenski
(74) *Attorney, Agent, or Firm* — Saul Ewing Arnstein & Lehr LLP; Kathryn Doyle; Jacque Young

(57) ABSTRACT

The present invention relates to B7-H4-specific compositions and methods of use thereof.

9 Claims, 33 Drawing Sheets

Specification includes a Sequence Listing.

(56) References Cited

U.S. PATENT DOCUMENTS

| | | | |
|---|---|---|---|
| 6,867,041 B2 | 3/2005 | Berenson et al. | |
| 6,887,466 B2 | 5/2005 | June et al. | |
| 6,891,030 B2 | 5/2005 | Chen | |
| 6,905,874 B2 | 6/2005 | Berenson et al. | |
| 7,067,318 B2 | 6/2006 | June et al. | |
| 7,144,575 B2 | 12/2006 | June et al. | |
| 7,172,869 B2 | 2/2007 | June et al. | |
| 7,175,843 B2 | 2/2007 | June et al. | |
| 7,232,566 B2 | 6/2007 | June et al. | |
| 7,902,340 B2 | 3/2011 | Lichtlen et al. | |
| 8,444,971 B2 * | 5/2013 | Papkoff | A61P 13/12 424/130.1 |
| 8,906,369 B2 * | 12/2014 | Papkoff | A61K 51/1027 424/130.1 |
| 9,296,822 B2 * | 3/2016 | Korman | A61P 37/06 |
| 9,422,351 B2 | 8/2016 | Scholler et al. | |
| 9,447,186 B2 * | 9/2016 | Zang | A61K 39/39558 |
| 9,676,854 B2 * | 6/2017 | Liu | A61P 37/06 |
| 2004/0101519 A1 | 5/2004 | June et al. | |
| 2005/0042664 A1 | 2/2005 | Wu et al. | |
| 2005/0048617 A1 | 3/2005 | Wu et al. | |
| 2006/0034810 A1 | 2/2006 | Riley et al. | |
| 2006/0121005 A1 | 6/2006 | Berenson et al. | |
| 2009/0142342 A1 | 6/2009 | Chen et al. | |
| 2011/0085970 A1 | 4/2011 | Terrett et al. | |
| 2011/0091449 A1 | 4/2011 | Payne et al. | |
| 2011/0123541 A1 | 5/2011 | Bachmann et al. | |
| 2012/0148552 A1 | 6/2012 | Jensen et al. | |
| 2014/0004132 A1 | 1/2014 | Brenner et al. | |
| 2014/0308259 A1 | 10/2014 | Scholler et al. | |

FOREIGN PATENT DOCUMENTS

| | | |
|---|---|---|
| EP | 592106 A1 | 4/1994 |
| EP | 1921142 A1 | 5/2008 |
| WO | 9109967 A1 | 7/1991 |
| WO | 9110741 A1 | 7/1991 |
| WO | 9317105 A1 | 9/1993 |
| WO | 9633735 A1 | 10/1996 |
| WO | 9634096 A1 | 10/1996 |
| WO | 9816654 A1 | 4/1998 |
| WO | 9824893 A2 | 6/1998 |
| WO | 9846645 A2 | 10/1998 |
| WO | 9850433 A2 | 11/1998 |
| WO | 0129058 A1 | 4/2001 |
| WO | 0196584 A2 | 12/2001 |
| WO | 2010025177 A1 | 3/2010 |
| WO | 2010091637 A1 | 8/2010 |
| WO | 2013067492 A1 | 5/2013 |
| WO | 2014055657 A1 | 4/2014 |
| WO | 2014100439 A2 | 6/2014 |
| WO | 2014190356 A2 | 11/2014 |

OTHER PUBLICATIONS

Andris-Widhopf, et al., "Generation of Human scFv Antibody Libraries: PCR Amplication and Assembly of Light- and Heavy-Chain Coding Sequences", Cold Spring Harbor Protocols http://cshprotocols.cship.org, 2001.

Baca, et al., "Antibody Humanization Using Monovalent Phage Display", The Journal of Biological Chemistry 272, 1997, 10678-10684.

Beatty, et al., "CD40 Agonists Alter Tumor Stroma and Show Efficacy Against Pancreatic Carcinoma in Mice and Humans", Science 331(6024), 2011, 1612-1616.

Bergan, et al., "Development and in vitro validation of anti-mesothelin biobodies that prevent CA125/Mesothelin-dependent cell attachment", Cancer Letters 255, 2007, 263-274.

Bierer, et al., "Cyclosporin A and FK506: molecular mechanisms of immunosuppression and probes for transplantation biology", Current Opinion in Immunology 5, 1993, 763-773.

Bird, et al., "Single-Chain Antigen-Binding Proteins", Science, New Series 242(4877), 1988, 423-426.

Brentjens, et al., "Safety and persistence of adoptively transferred autologous CD19-targeted T cells in patients with relapsed or chemotherapy refractory B-cell leukemias", Blood 118(18), 2011, 4817-4828.

Brüggemann, et al., "Designer Mice: The Production of Human Antibody Repertoires in Transgenic Animals", Generation of Antibodies by Cell and Gene Immortalization, 7, 1993, 33-40.

Caldas, et al., "Design and synthesis of germline-based hemi-humanized single-chain Fv against the CD18 surface antigen", Protein Engineering 13(5), 2000, 353-360.

Carpenito, et al., "Control of large, established tumor xenografts with genetically retargeted human T cells containing CD28 and CD137 domains", PNAS 106(9):, 2009, 3360-3365.

Carter, et al., "Humanization of an anti-p185HER2 antibody for human cancer therapy", Proc. Natl. Acad. Sci. 89, 1992, 4285-4289.

Chen, et al., "Induced expression of B7-H4 on the surface of lung cancer cell by the tumor-associated macrophages: A potential mechanism of immune escape", Cancer Letters 317, 2012, 99-105.

Cheng, et al., "Overexpression of B7-H4 in tumor infiltrated dendritic cells", Journal of Immunoassay and Immunochemistry 32(4), 2011, 353-364.

Choi, et al., "Genomic Organization and Expression Analysis of B7-H4, an Immune Inhibitory Molecule of the B7 Family", The Journal of Immunology 171, 2003, 4650-4654.

Chothia, et al., "Canonical Structures for the Hypervariable Regions of Immunoglobulins", J. Mol. Biol. 196, 1987, 901-917.

Clackson, et al., "Making antibody fragments using phage display libraries", Nature 352, 1991, 624-628.

Coffelt, et al., "Tumor-associated macrophages: Effectors of angiogenesis and tumor progression", Biochimica et Biophysica Acta. 1796, 2009, 11-18.

Couto, et al., "Anti-BA46 Monoclonal Antibody Mc3: Humanization Using a Novel Positional Consensus and in Vivo and in Vitro Characterization", Cancer Research 55, 1995, 1717-1722.

Couto, et al., "Designing Human Consenus Antibodies with Minimal Positional Templates", Cancer Research 55(23 Suppl.), 1995, 5973s-5977s.

Curiel, et al., "Specific recruitment of regulatory T cells in ovarian carcinoma fosters immune privilege and predicts reduced survival", Nature Medicine 10(9), 2004, 942-949.

Dangaj, et al., "A Novel anti-B7-H4 human recombinant antibody overcomes TAM-mediated T-cell inhibition", The Journal of Immunology 188, 2012, 46.43 (abstract only).

Dangaj, et al., "Mannose Receptor (MR) Engagement by Mesothelin GPI Anchor Polarizes Tumor-Associated Macrophages and Is Blocked by Anti-MR Human Recombinant Antibody", PLoS One 6(12), 2011, e28386.

Dangaj, et al., "Novel Recombinant Human B7-H4 Antibodies Overcome Tumoral Immune Escape to Potentiate T-Cell Antitumor Responses", Cancer Res. 73(15), 2013, 4820-4829.

Duchosal, et al., "Immunization of hu-PBL-SCID mice and the rescue of human monoclonal Fab fragments through combinatorial libraries", Nature 355, 1992, 258-262.

Garland, et al., "The use of Teflon cell culture bags to expand functionally active CD8+ cytotoxic T lymphocytes", Journal of Immunological Methods 227, 1999, 53-63.

Griffiths, et al., "Human anti-self antibodies with high specificity from phage display libraries", The EMBO Journal 12(2), 1993, 725-734.

Haanen, et al., "Selective Expansion of Cross-reactive CD8+ Memory T Cells by Viral Variants", J. Exp. Med. 190(9), 1999, 1319-1328.

Hagemann, et al., "Ovarian Cancer Cells Polarize Macrophages Toward a Tumor-Associated Phenotype", The Journal of Immunology 176, 2006, 5023-5032.

He, et al., "The inhibitory role of b7-h4 in antitumor immunity: association with cancer progression and survival", Clin Dev Immunol. vol. 2011, Article ID 685834, 8 pages, Epub Oct. 13, 2011, 2011.

Henderson, et al., "Comparison of the effects of FK-506, cyclosporin A and rapamycin on IL-2 production", Immunology 73, 1991, 316-321.

(56) References Cited

OTHER PUBLICATIONS

Huston, et al., "Protein engineering of antibody binding sites: Recovery of specific activity in an anti-digoxin single-chain Fv analogue produced in *Escherichia coli*", Proc. Natl. Acad. Sci. 85, 1988, 5879-5883.
Jakobovits, et al., "Analysis of homozygous mutant chimeric mice: Deletion of the immunoglobulin heavy-chain joining region blocks B-cell development and antibody production", Proc. Natl. Acad. Sci. 90, 1993, 2551-2555.
Jakobovits, et al., "Germ-line transmission and expression of a human-derived yeast artificial chromosome", Nature 362, 1993, 255-258.
Jiang, et al., "Tumor expression of B7-H4 predicts poor survival of patients suffering from gastric cancer", Cancer Immunol. Immunother. 59, 2010, 1707-1714.
Johnson, et al., "Gene Transfer of Tumor-Reactive TCR Confers Both High Avidity and Tumor Reactivity to Nonreactive Peripheral Blood Mononuclear Cells and Tumor-Infiltrating Lymphocytes1", J. Immunol. 177(9), 2006, 6548-6559.
Johnson, et al., "Human antibody engineering", Current Opinion in Structural Biology 3, 1993, 564-571.
Jones, et al., "Replacing the complementarity-determining regions in a human antiboby with those from a mouse", Nature 321, 1986, 522-525.
Krambeck, et al., "B7-H4 expression in renal cell carcinoma and tumor vasculature: Associations with cancer progression and survival", PNAS 103(27), 2006, 10391-10396.
Kryczek, et al., "B7-H4 expression identifies a novel suppressive macrophage population in human ovarian carcinoma", The Journal of Experimental Medicine 203(4), 2006, 871-881.
Kryczek, et al., "Cutting-Edge: Induction of B7-H4 on APCs through IL-10: Novel Suppressive Mode for Regulatory T Cells", The Journal of Immunology 177, 2006, 40-44.
Kryczek, et al., "Relationship between B7-H4, Regulatory T Cells, and Patient Outcome in Human Ovarian Carcinoma", Cancer Res. 67(18), 2007, 8900-8905.
Lanitis, et al., "Redirected Antitumor Activity of Primary Human Lymphocytes Transduced With a Fully Human Anti-mesothelin Chimeric Receptor", Molecular Therapy, 20(3), 2012, 633-643.
Levine, et al., "Effects of CD28 Costimulation on Long-Term Proliferation of CD4+ T Cells in the Absence of Exogenous Feeder Cells1", The Journal of Immunology 159, 1997, 5921-5930.
Liu, et al., "Calcineurin Is a Common Target of Cyclophilin-Cyclosporin A and FKBP-FK506 Complexes", Cell 66, 1991, 807-815.
Lonberg, et al., "Human Antibodies from Transgenic Mice", Intern. Rev. Immunol. 13, 1995, 65-93.
Marks, et al., "By-passing Immunization Human Antibodies from V-gene Libraries Displayed on Phage", J. Mol. Biol. 222, 1991, 581-597.
McCafferty, et al., "Phage antibodies: filamentous phage displaying antibody variable domains", Nature 348, 1990, 552-554.
Miyatake, et al., "B7-H4 (DD-O110) is overexpressed in high risk uterine endometriod adenocarcinomas and inversely correlated with tumor T-cell infiltration", Gynecol. Oncol. 106(1), 2007, 119-127.
Morea, et al., "Antibody Modeling: Implications for Engineering and Design", Methods 20, 2000, 267-279.
Mumtaz, et al., "Design of liposomes for circumventing the reticuloendothelial cells", Glycobiology 1(5), 1991, 505-510.
Padlan, et al., "A possible procedure for reducing the immunogenicity of antibody variable domains while preserving their ligand-binding properties", Molecular Immunology 28(4/5), 1991, 489-498.
Paul, et al., GenBank Direct Submission Accession No. AF329456, Dec. 18, 2000.
Pedersen, et al., "Comparison of Surface Accessible Residues in Human and Murine Immunoglobulin Fv Domains, Implications for Humanization of Murine Antibodies", J. Mol. Biol. 235, 1994, 959-973.
Porter, et al., "Chimeric antigen receptor-modified T cells in chronic lymphoid leukemia", NEJM 365(8), 2011, 725-733.
Prasad, et al., "B7S1, a novel B7 family member that negatively regulates T cell activation", Immunity, 18(6), 2003, 863-873.
Presta, "Antibody engineering", Current Opinion in Biotechnology 3, 1992, 394-398.
Presta, et al., "Humanization of an Antibody Directed Against IgE", The Journal of Immunology 151, 1993, 2623-2632.
Pule, et al., "Virus-specific T cells engineered to coexpress tumor-specific receptors: persistence and antitumor activity in individuals with neuroblastoma", Nat Med. 14(11), 2008, 1264-1270.
Qian, et al., "Development of a novel monoclonal antibody to B7-H4: characterization and biological activity", Eur J Med Res. 16(7), 2011, 295-302.
Quandt, et al., "B7-H4 Expression in Human Melanoma: Its Association with Patients' Survival and Antitumor Immune Response", Clin. Cancer Res. 17(10), 2011, 3100-3111.
Riechmann, et al., "Reshaping human antibodies for therapy", Nature 332, 1988, 323-327.
Roder, et al., "The EBV-Hybridoma Technique", Methods in Enzymology, 121, 1986, 140-167.
Roguska, et al., "A comparison of two murine monoclonal antibodies humanized by CDR-grafting and variable domain resurfing", Protein Engineering 9(10), 1996, 895-904.
Roguska, et al., "Humanization of murine monoclonal antibodies through variable domain resurfacing", Proc. Natl. Acad. Sci. 91, 1994, 969-973.
Rolny, et al., "HRG Inhibits Tumor Growth and Metastasis by Inducing Macrophage Polarization and Vessel Normalization through downregulation of PIGF", Cancer Cell 19, 2011, 31-44.
Salter, et al., "Impaired assembly and transport of HLA-A and -B antigens in a mutant TxB cell hybrid", The EMBO Journal 5(5), 1986, 943-949.
Sandhu, "A rapid procedure for the humanization of monoclonal antibodies", Gene 150, 1994, 409-410.
Scoller, et al., "Method for Generation of in vivo Biotinylated Recombinant Antibodies by Yeast Mating", J. Immunol. Methods 317(1-2), 2006, 132-143.
Sica, et al., "B7-H4, a molecule of the B7 family, negatively regulates T cell immunity", Immunity 18(6), 2003, 849-861.
Simon, et al., "B7-H4 Is a Novel Membrane-Bound Protein and a Candidate Serum and Tissue Biomarker for Ovarian Cancer", Cancer Research 66(3), 2006, 1570-1575.
Sims, et al., "A Humanized CD18 Antibody Can Block Function without Cell Destruction", The Journal of Immunology 151(4), 1993, 2296-2308.
Skerra, et al., "Assembly of a Functional Immunoglobulin Fv Fragment in *Escherichia coli*", Science, 240, 1988, 1038-1041.
Sood, "PDEF and PDEF-induced proteins as candidate tumor antigens for T cell and antibody-mediated immunotherapy of breast cancer", Immunol Res 46, 2010, 206-215.
Studnicka, et al., "Human-engineered monoclonal antibodies retain full specific binding activity by preserving non-CDR complementarity-modulating residues", Protein Engineering 7(6), 1994, 805-814.
Sun, et al., "B7-H3 and B7-H4 expression in non-small-cell lung cancer", Lung Cancer 53(2), 2006, 143-151.
Taguchi, et al., GenBank Direct Submission Accession No. FJ231720, Sep. 23, 2008.
Tan, et al., "Superhumanized Antibodies: Reduction of Immunogenic Potential by Complementarity-Determining Region Grafting with Human Germline Sequences: Application to an Anti-CD28", The Journal of Immunology 169, 2002, 1119-11125.
Ten Berge, et al., "Selective Expansion of a Peripheral Blood CD8+ Memory T Cell Subset Expressing Both Granzyme B and L-Selectin During Primary Viral Infection in Renal Allograft Recipients", Transplantation Proceedings 30, 1998, 3975-3977.
Thompson, et al., "Serum-Soluble B7x is Elevated in Renal Cell Carcinoma Patients and is Associated with Advanced Stage", Cancer Res. 68(15), 2008, 6054-6058.
Tringler, et al., "B7-H4 is Highly Expressed in Ductal and Lobular Breast Cancer", Clinical Cancer Research 11, 2005, 1842-1848.

(56) References Cited

OTHER PUBLICATIONS

Ui-Tei, et al., "Sensitive assay of RNA interference in *Drosophila* and Chinese hamster cultured cells using firefly luciferase gene as target", FEBS Letters 479, 2000, 79-82.

Vaughan, et al., "Human antibodies with sub-nanomolar affinities isolated from a large non-immunized phage display library", Nat. Biotechnol.14(3), 1996, 309-314.

Verhoeyen, et al., "Reshaping Human Antibodies: Grafting an Antilysozyme Activity", Science 239(4847), 1988, 1534-1536.

Wang, et al., "Mining a Yeast Library for Brain Endothelial Cell-Binding Antibodies", Nat. Methods 4(2), 2007, 143-145.

Ward, et al., "Binding activities of a repertoire of single immunoglobulin variable domains secreted from *Escherichia coli*", Nature 341, 1989, 544-546.

Wu, et al., "Humanization of a Murine Monoclonal Antibody by Simultaneous Optimization of Framework and CDR Residues", J. Mol. Biol. 294, 1999, 151-162.

Yu, et al., "B7-H4's role beyond the tumor", Inflammation 36(4), Aug. 2013, 941-947.

Zeisberger, et al., "Clodronate-liposome-mediated depletion of tumour-associated macrophages: a new and highly effective antiangiogenic therapy approach", British Journal of Cancer 95, 2006, 272-281.

Zhang, et al., "In Vivo Gene Delivery by Nonviral Vectors: Overcoming Hurdles?", Molecular Therapy 20(7), 2012, 1298-1304.

Zhang, et al., "Intratumoral T cells, Recurrence, and Survival in Epithelial Ovarian Cancer", N. Engl. J. Med. 348(3), 2003, 203-213.

Zhao, et al., "Rapid isolation of high affinity human antibodies against the tumor vascular marker Endosialin/TEM1, using a paired yeast display/secretory scFv library platform", J. Immunol. Methods 363(2), 2011, 221-232.

Zhu, et al., "B7-H4-deficient mice display augmented neutrophil-mediated innate immunity", Blood 113(8), 2009, 1759-1767.

* cited by examiner

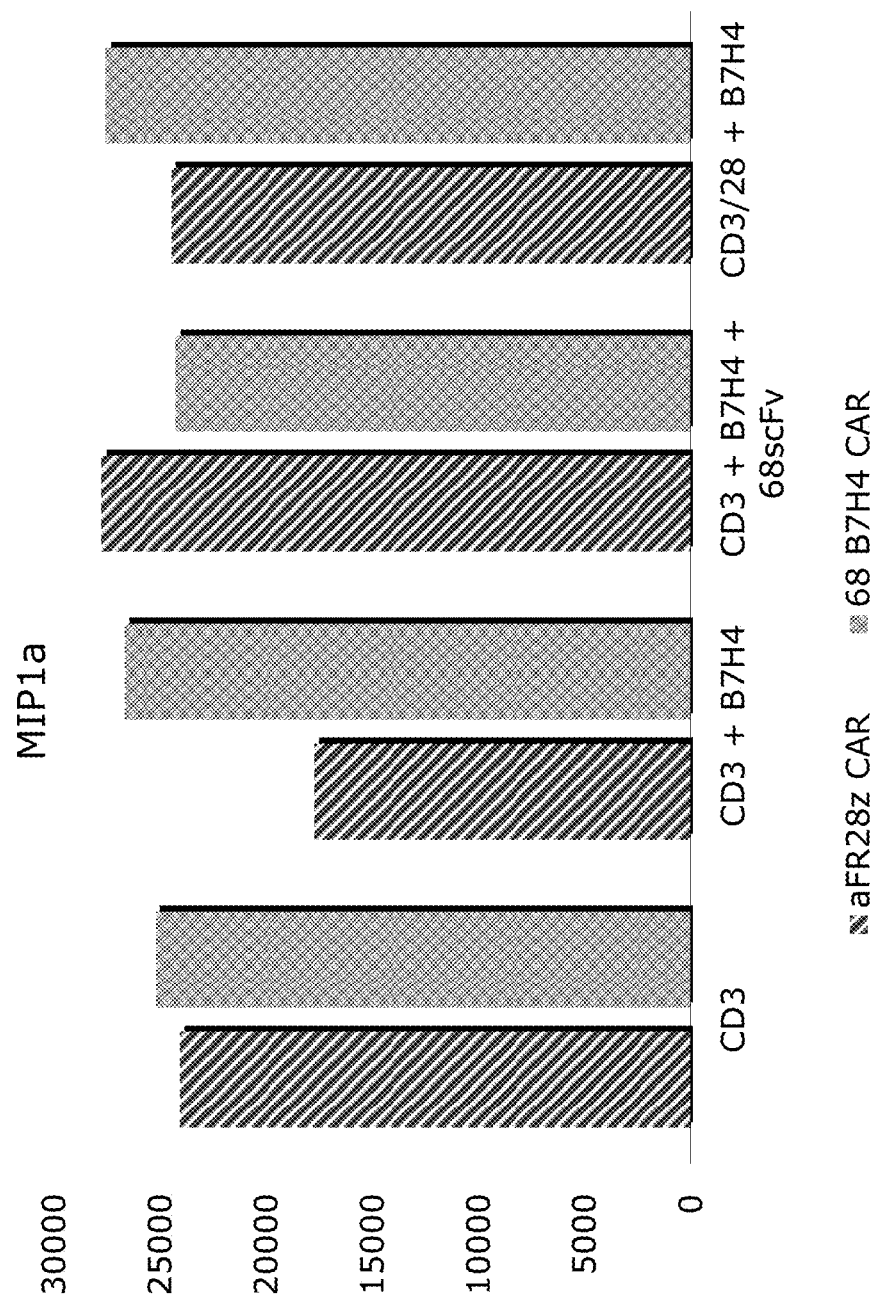

ISOLATED B7-H4 SPECIFIC COMPOSITIONS AND METHODS OF USE THEREOF

CROSS-REFERENCE TO RELATED APPLICATION

This application is a divisional of, and claims priority to, U.S. patent application Ser. No. 15/009,082, filed Jan. 28, 2016, now U.S. Pat. No. 10,259,849, which is a divisional of U.S. patent application Ser. No. 14/181,931, filed on Feb. 17, 2014, now U.S. Pat. No. 9,279,008, which is a continuation of PCT International Application No. PCT/US2012/063546, filed on Nov. 5, 2012, which claims the benefit pursuant to 35 U.S.C. § 119(e) of U.S. Provisional Application No. 61/555,406, filed on Nov. 3, 2011, each of which are hereby incorporated by reference in their entirety herein.

STATEMENT REGARDING FEDERALLY SPONSORED RESEARCH OR DEVELOPMENT

This invention was made with government support under grant number W81XWH-12-1-0602 awarded by the Army and the Medical Research and Material Command Office. The government has certain rights in the invention.

BACKGROUND OF THE INVENTION

Tumor-associated macrophages (TAMs) inhibit anti-tumor immune responses through the release of humoral mediators such as cytokines, prostaglandins, growth factors and metalloproteases. TAMs can also protect tumors from immune recognition by hampering cell-mediated immune responses through the cell-surface expression of inhibitory molecules such as B7-H4 (Kryczek et al., 2006, J Exp Med 203(4):871-81). TAMs derive from resident macrophages or from monocytes recruited by the tumor microenvironment and polarized at the tumor site (Qia and Pollard, 2010, Cell 141(1):39-51; Allavena and Mantovani, 2012, Clin Exp Immunol 167(2): 195-205). Tumor infiltration with TAMs has been associated with poor patient survival and higher microvessel density (Coffelt et al., 2009, Biochim Biophys Acta 1796(1): 11-8). Targeting TAMs represents a promising strategy against cancer and several approaches have already been developed, including depletion with clodronate liposomes (Zeisberger et al., 2006, Br J Cancer 95(3):272-81); inhibition of tumor recruitment by targeting of CFSR-1 and CCL2 (Loberg et al., 2007, Cancer Res 67(19):9417-24); and "re-education" through activation, via CD40 with anti-CD40 mAbs (Beatty et al., 2011, Science 331(6024): 1612-6) or via HRG plasma protein (Rolny et al., 2011, Cancer Cell 19(1):31-44) or mannose receptor (Dangaj et al., 2011, PLoS One 6(12):e28386).

B7-H4 or B7x/B7s is a member of the B7 superfamily and has recently identified as an inhibitory modulator of T-cell response (Sica et al., 2003, Immunity 18(6):849-61; Prasad et al., 2003, Immunity 18(6):863-73; Zang et al., 2003, Proc Natl Acad Sci USA, 100(18):10388-92). When present at the surface of antigen presenting cells, B7-H4 negatively regulates T cell activation, possibly through interaction with a ligand that remains to be identified (Kryczek et al., 2006, J Immunol 177(1):40-4). B7-H4 adenoviral overexpression in pancreatic islets protected mice from autoimmune diabetes maintaining peripheral tolerance (Wei et al., 2011, J Exp Med, 208(8): 1683-94). Consistently with this observation, B7-H4 knock-out mice are more resistant to infection by *Listeria monocytogenes* than their wild type littermates due to a higher proliferation of neutrophils in peripheral organs (Zhu et al., 2009, Blood, 113(8):1759-67).

B7-H4 is widely expressed at the mRNA level, but its restricted pattern of protein expression in normal tissues suggests posttranscriptional regulation. B7-H4 expression in tumor tissues was observed in various types of human cancers such as breast (Tringler et al., 2005, Clin Cancer Res 11(5):1842-8), ovarian (Kryczek et al., 2006, J Exp Med 203(4):871-81), pancreatic, lung (Choi et al., 2003, J Immunol 171(9):4650-4; Sun et al., 2006, Lung Cancer 53(2): 143-51) melanoma (Quandt et al., 2011, Clin Cancer Res 17(10):3100-11) and renal cell carcinoma (Jung et al., 2011, Korean J Urol 52(2):90-5; Krambeck et al., 2006, Proc Natl Acad Sci USA 103(27): 10391-6). B7-H4 expression was evaluated by immunohistochemistry in most studies, either as a cytoplasm or a plasma membrane protein (Quandt et al., 2011, Clin Cancer Res 17(10):3100-11; Krambeck et al., 2006, Proc Natl Acad Sci USA 103(27): 10391-6; Jiang et al., 2010, Cancer Immunol Immunother 59(11): 1707-14; Zang et al., 2007, Proc Natl Acad Sci USA, 104(49):19458-63; Miyatake et al., 2007, Gynecol Oncol 106(1): 119-27). In ovarian cancer cells, B7-H4 expression was assessed by flow cytometry and was also reported to be mainly intracellular (Kryczek et al., 2006, J Exp Med 203(4):871-81), to the exception of some cell lines where cell surface expression was observed (Choi et al., 2003, J Immunol 171(9): 4650-4). B7-H4 has also been detected in a soluble form in blood samples from cancer patients (Simon et al., 2006, Cancer Res 66(3):1570-5; Thompson et al., 2008, Cancer Res 68(15):6054-8). The broad presence in various cancers of a negative regulator of T cell activation suggests a role of B7-H4 in down-regulating antitumor immunity. In fact, ovarian cancer-derived B7-H4$^+$ TAMs suppress HER2 antigen-specific T-cell proliferation and cytotoxicity, and the blocking of B7-H4 expression on macrophages using morpholino antisense oligonucleotides in vitro and in vivo improves tumor-associated antigen T-cell responses (Kryczek et al., 2006, J Exp Med 203(4):871-81).

Altogether, these results support B7-H4 translational value as a target molecule for anti-tumor immunotherapy. However, the use of antisense nucleic acids remains limiting in clinics, in part because of a low stability in vivo due to serum inactivation, enzyme degradation, and innate immune activation, but also because of the lack of specific targeting and rapid elimination when oligonucleotides are delivered in a naked form (Zhang et al., 2012, Mol Ther 20(7): 1298-304). Other means for blocking B7-H4 activity need to be developed for clinical applications. The present invention addresses this need.

SUMMARY OF THE INVENTION

The invention provides an isolated polynucleotide encoding a human anti-B7-H4 antibody or a fragment thereof, wherein the antibody or a fragment thereof comprises an amino acid sequence selected from the group consisting of SEQ ID NOs: 1-4. In one embodiment, the isolated polynucleotide encoding a human anti-B7-H4 antibody or a fragment thereof comprises a nucleic acid sequence selected from the group consisting of SEQ ID NOs: 5-8.

In one embodiment, the isolated polypeptide encoding a human anti-B7-H4 antibody or a fragment thereof comprises an amino acid sequence selected from the group consisting of SEQ ID NOs: 1-4.

In one embodiment, the antibody or fragment thereof comprises a fragment selected from the group consisting of an Fab fragment, an F(ab')$_2$ fragment, an Fv fragment, and a single chain Fv (scFv).

The present invention provides a method for diagnosing a disease, disorder or condition associated with the expression of B7-H4 on a cell, the method comprising a) contacting the cell with a human anti-B7-H4 antibody or fragment thereof, wherein the antibody or a fragment thereof comprises an amino acid sequence selected from the group consisting of SEQ ID NOs: 1-4; and b) detecting the presence of B7-H4 wherein the presence of B7-H4 diagnoses for the disease, disorder or condition associated with the expression of B7-H4.

In one embodiment, the disease, disorder or condition associated with the expression of B7-H4 is cancer.

The invention also provides a method of diagnosing, prognosing, or determining risk of a B7-H4-related disease in a mammal, the method comprising detecting the expression of B7-H4 in a sample derived from the mammal comprising: a) contacting the sample with a human anti-B7-H4 antibody or fragment thereof, wherein the antibody or a fragment thereof comprises an amino acid sequence selected from the group consisting of SEQ ID NOs: 1-4; and b) detecting the presence of B7-H4 wherein the presence of B7-H4 diagnoses for a B7-H4-related disease in the mammal.

The invention also provides a method of inhibiting B7-H4-dependent T cell inhibition, the method comprising contacting a cell with a human anti-B7-H4 antibody or fragment thereof, wherein the antibody or a fragment thereof comprises an amino acid sequence selected from the group consisting of SEQ ID NOs: 1-4. In one embodiment, the cell is selected from the group consisting of a B7-H4-expressing tumor cell, a tumor-associated macrophage (TAM), and any combination thereof.

The invention also provides a method of blocking T-cell inhibition mediated by a B7-H4-expressing cell and altering the tumor microenvironment to inhibit tumor growth in a mammal, the method comprising administering to the mammal an effective amount of a composition comprising an isolated anti-B7-H4 antibody or fragment thereof, wherein the antibody or a fragment thereof comprises an amino acid sequence selected from the group consisting of SEQ ID NOs: 1-4. In one embodiment, the cell is selected from the group consisting of a B7-H4-expressing tumor cell, a tumor-associated macrophage (TAM), and any combination thereof.

The invention also provides a method of inhibiting, suppressing or preventing immunosuppression of an anti-tumor or anti-cancer immune response in a mammal, the method comprising administering to the mammal an effective amount of a composition comprising an isolated anti-B7-H4 antibody or fragment thereof, wherein the antibody or a fragment thereof comprises an amino acid sequence selected from the group consisting of SEQ ID NOs: 1-4. In one embodiment, the antibody or fragment thereof inhibits the interaction between a first cell with a T cell, wherein the first cell is selected from the group consisting of a B7-H4-expressing tumor cell, a tumor-associated macrophage (TAM), and any combination thereof.

The invention also provides an isolated nucleic acid sequence encoding a chimeric antigen receptor (CAR), wherein the isolated nucleic acid sequence comprises the sequence of a human B7-H4 binding domain and the sequence of a CD3 zeta signaling domain. In one embodiment, isolated nucleic acid sequence further comprises the sequence of a co-stimulatory signaling domain.

In one embodiment, the co-stimulatory signaling domain is selected from the group consisting of the CD28 signaling domain, the 4-1BB signaling domain, and any combination thereof.

In one embodiment, the human B7-H4 binding domain is a human antibody or a fragment thereof is selected from the group consisting of an Fab fragment, an F(ab')$_2$ fragment, an Fv fragment, and a single chain Fv (scFv).

In one embodiment, the antibody or a fragment thereof comprises an amino acid sequence selected from the group consisting of SEQ ID NOs: 1-4. In another embodiment, the antibody or a fragment thereof comprises a nucleic acid sequences selected from the group consisting of SEQ ID NOs: 5-8.

The invention also provides an isolated chimeric antigen receptor (CAR) comprising a human B7-H4 binding domain and a CD3 zeta signaling domain. In one embodiment, the CAR further comprises the sequence of a co-stimulatory signaling domain.

In one embodiment, the co-stimulatory signaling domain is selected from the group consisting of the CD28 signaling domain, the 4-1BB signaling domain, and any combination thereof.

In another embodiment, the human B7-H4 binding domain is a human antibody or a fragment thereof is selected from the group consisting of an Fab fragment, an F(ab')$_2$ fragment, an Fv fragment, and a single chain Fv (scFv). In one embodiment, the antibody or a fragment thereof comprises an amino acid sequence selected from the group consisting of SEQ ID NOs: 1-4.

The invention also provides a method of providing an anti-tumor immunity in a mammal, the method comprising administering to the mammal an effective amount of a genetically modified cell comprising an isolated nucleic acid sequence encoding a chimeric antigen receptor (CAR), wherein the isolated nucleic acid sequence comprises the sequence of a human B7-H4 binding domain and the nucleic acid sequence of a CD3 zeta signaling domain.

In one embodiment, the cell is an autologous T cell.

In one embodiment, the mammal is a human.

The invention also provides a method of treating a mammal having a disease, disorder or condition associated with dysregulated expression of B7-H4, the method comprising administering to the mammal an effective amount of a genetically modified cell comprising an isolated nucleic acid sequence encoding a chimeric antigen receptor (CAR), wherein the isolated nucleic acid sequence comprises the sequence of a human B7-H4 binding domain and the nucleic acid sequence of a CD3 zeta signaling domain.

In one embodiment, the disease, disorder or condition associated with dysregulated expression of B7-H4 is selected from the group consisting of liver cancer, pancreatic cancer, ovarian cancer, stomach cancer, lung cancer, endometrial cancer, hepatocellular carcinoma, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 2A is an image of the morphology of M1 and M2 macrophages after in vitro cytokine maturation. FIGS. 2B-2D demonstrate that induction of macrophage B7-H4 expression was determined by (FIG. 2B) qRT-PCR; and (FIGS. 2C-2D) flow cytometry, after (FIG. 2B lanes 1-2 and FIG. 2C) cytokine stimulation, or (FIG. 2B lane 3 and FIG. 2D) co-culture with Ovcar3 tumor cell line.

FIG. 3A demonstrates anti-B7-H4 scFv binding to serial dilutions of recombinant B7-H4 vs. irrelevant antigen as measured by capture ELISA. FIG. 3B is an image of a flow cytometry analysis of anti-B7-H4 biobodies binding to M1 and M2 macrophages after pre-coupling to fluorescent streptavidin beads (Myltenyi).

FIGS. 4A-4D demonstrate that T cell proliferation was assessed after analyzing CFSE dilution in anti-CD3/CD28 stimulated T cells alone (FIG. 4A); T cells with M1 macrophages (FIG. 4B); T cells in transwell co-culture with ovcar3 (FIG. 4C); T cells with TAMs in transwell co-culture with ovcar3 (FIG. 4D). FIG. 4E demonstrates that T cell activation was evaluated based on CD69 expression after anti-CD3/CD28 stimulation of T cells alone or in presence of M1 or TAMs.

FIG. 5A is an image of a flow cytometry and western blot analysis of B7-H4 expression in ovarian cancer cell lines. Cell lines (as indicated) were labeled with PE-conjugated anti-B7-H4 mAb (open histogram) or PE-conjugated isotype control (grey filled histogram). EBV B cells, M2 macrophages and B7-H4 transduced C30 cells were used as positive control (upper panel). The lower panel shows a Western blot analysis of B7-H4 expression in four ovarian cancer cell lines (OVCAR5, SKOV3, A1857, OVCAR3). IL4-IL10 in vitro maturated macrophages (M2 MP) were used as positive controls for B7-H4 expression. (3-actin detection was used as endogenous protein loading control. FIG. 5B shows a flow cytometry evaluation of B7-H4 surface expression in human ovarian cancer ascites and solid tumors samples. Dead cells were excluded from total cells based on 7-AAD uptake. Tumor cells and leukocytes were distinguished through the detection of Epcam and CD45 surface markers. Macrophage population that expressed surface B7-H4 were characterized by the co-expression of $CD45^+CD14^+CD206^+$ $B7-H4^+$. Tumor cells that expressed surface B7-H4 were characterized by the co-expression of $Epcam^+B7-H4^+$. FIGS. 5C-5D depict B7-H4 cell surface expression on tumor cells in ascites and solid tumor samples derived from a xenogeneic mouse model of human ovarian cancer. FIG. 5C shows a representative flow cytometry analysis of B7-H4 cell surface expression on freshly harvested, uncultured $Epcam^+$ tumor cells (upper panels) vs. $Epcam^+$ tumor cells after short in vitro culture (lower panels). FIG. 5D is an image of a plot of percentages of B7-H4+ EpCAM+ cells derived from ascites and solid tumors before and after short term culture, as measured by flow cytometry (n=6). Isotype PE IgG1 was used as staining control for B7-H4.

FIG. 6A is a schematic representation of protein-based (FIG. 6B) and cell-based isolation (FIG. 6C) strategies. Protein-based and cell-based isolated anti-B7-H4 scFvs were plastic-immobilized and incubated with serial dilutions of biotinylated recombinant B7-H4 (black diamonds) or irrelevant control antigen (BSA, grey triangles) (FIGS. 6B-6C). Protein binding to scFv was detected with SA-HRP. Colorimetric signal was developed with TMB substrate solution, quenched with sulfuric acid and read at 450 nm on a Biotek ELISA reader.

FIG. 7A depicts IFN-γ production (ELISA assays). p=0.032 for CD3-stimulated T cells and p=0.097 for CD3/CD28-stimulated T cells in the absence or in the presence of B7-H4. Error bars represent standard error of mean (SEM). FIG. 7B depicts a flow cytometry analysis of CD69 T cell expression and T cell proliferation as measured by CFSE dilutions, as indicated. FIG. 7C illustrates IFN-γ production (ELISA assays) from T cells stimulated with plate bound anti-CD3 in the presence of immobilized recombinant B7-H4 (black bars) or of irrelevant control protein (FOLR1, grey bars) in regular medium (untreated) or in the presence of anti-B7-H4 scFvs clones #26, #56, 3#54, or 3#68, as indicated. Untreated samples, p=0.0014; #26, p=0.0019; #56, p<0.0001; 3#54 p=0.0406; 3#68, p=0.1305. Error bars represent standard error of mean (SEM). FIG. 7D depicts a flow cytometry analysis of CD69 T cell expression and T cell proliferation as measured by CFSE dilutions, as indicated.

FIG. 8A depicts a flow cytometry analysis of B7-H4 surface expression in wild type or B7-H4 transduced T2 APCs using PE anti-B7-H4 mAb (open histogram) or isotype PE (grey filled histogram). IFN-γ production of HER-2 (FIG. 8B) and MART-1 (FIG. 8C) TCR specific T cells after stimulation with B7-H4 transduced T2 APCs (T2 B7-H4, black bars) or wild type T2 (T2, grey bars) pulsed with MART-1 or HER-2 peptides. p=0.0362 for HER-2 TCR T cells stimulated with HER-2-pulsed T2 vs T2 B7-H4; p=0.0024 for MART-1 TCR T cells stimulated with MART-1-pulsed T2 vs T2 B7-H4; IFN-γ production of HER-2 (FIG. 8D) and MART-1 (FIG. 8E) TCR specific T cells after stimulation with B7-H4 expressing T2 APCs (T2 B7-H4, black bars) or GFP transduced T2 APCs (GFP T2, dark grey bars), pulsed with HER-2 (FIG. 8D) or MART-1 (FIG. 8E) peptides, in the presence of anti-B7-H4 scFvs, as indicated, or in regular medium (untr.). One Way Anova analysis for IFNγ production of antigen-specific T cells stimulated by peptide-loaded GFP T2 APCs, p=0.7893 (FIG. 8D, dark grey bars) and p=0.2931 (FIG. 8E, dark grey bars). One Way Anova analysis for IFNγ production of antigen-specific T cells stimulated by peptide-loaded T2 B7-H4 APCs, p=0.0066 (FIG. 8D, black bars) and p<0.0001 (FIG. 8E, black bars). In presence of anti-B7-H4 scFvs 3#68, p=0.5748 for HER-2 TCR T cells stimulated by peptide-loaded GFP vs. T2 B7-H4 APCs (FIG. 8D) and p=0.2892 for MART-1 TCR T cells stimulated by peptide-loaded GFP vs. T2 B7-H4 APCs (FIG. 8E). Error bars represent standard error of mean (SEM).

FIG. 9A depicts a flow cytometry analysis of B7-H4 surface expression in wild type 624 (WT 624) or B7-H4 transduced HLA A2$^+$ HER2$^+$624 (B7-H4$^+$624) cells, and wild type (WT MDA231) or B7-H4 transduced HLA A2$^{high}$ HER2$^+$ MDA231 (B7-H4$^+$ MDA231) cells, with PE anti-B7-H4 mAb (open histogram) or isotype PE (grey filled histogram). FIG. 9B depicts IFN-γ secretion of HER-2 TCR specific T cells after stimulation with WT 624 vs. B7-H4+ 624 (N/A), and with WT MDA231 vs. B7-H4 MDA231 (p=0.0451). FIG. 9C depicts IFN-γ secretion of HER-2 TCR specific T cells after stimulation with WT MDA231 vs. B7-H4 MDA231 in the presence of anti-B7-H4 scFvs, as indicated. One Way Anova analysis for IFNγ production of antigen-specific T cells stimulated by WT MDA231, p=0.1726 (dark grey bars). One Way Anova analysis for IFNγ production of antigen-specific T cells stimulated by B7-H4+ MDA231, p=0.0066 (black bars). With anti-B7-H4 scFv 3#54 stimulation with WT vs. B7-H4+ MDA231, p=0.4393; with anti-B7-H4 scFv 3#68 stimulation with WT vs. B7-H4+ MDA231, p=0.2179. Error bars represent standard error of mean (SEM).

FIG. 10A depicts IFN-γ production of MART-1 TCR specific T cells in the presence (black bars) or in the absence (grey bars) of B7-H4$^+$TAMs during stimulation with T2 APCs pulsed with serial dilutions of MART-1 peptide or constant concentration (1 μM) of HER-2 peptide to control for specific MART-1 TCR T cell stimulation. At dilution 0.0025 μM, p=0.0287; at dilution 0.05 μM, p=0.2777; at dilution 1 μM, p=0.1268. FIG. 10B depicts IFN-γ production of MART-1 TCR specific T cells in the presence (black bars) or in the absence (grey bars) of B7-H4$^+$TAMs during stimulation with T2 APCs pulsed with MART-1 peptide in the presence of anti-B7-H4 scFvs, as indicated. ANOVA to calculate. Error bars represent standard error of mean (SEM).

FIG. 11A depicts cDNA expression of B7-H4 in macrophages (1) after 2 and 5 hrs of stimulation with IL10/IL4 or (2) after 72 hrs in transwell co-culture with OVCAR3 cell line. Simultaneous (3-actin amplification was used as control. FIG. 11B is a schematic of mammalian cloning vector (pTT28) encoding soluble recombinant B7-H4 protein fused to a 6×HIS Tag. FIG. 11C depicts detection of recombinant B7-H4 (1) by western blot in the supernatant of 293-F cells using a HIS-probe followed by anti-mouse HRP or (2) after purification using an anti-human B7-H4 goat polyclonal Ab followed by polyclonal rabbit anti-goat HRP; (3) by coumassie staining after electrophoresis.

FIG. 15A demonstrates that B7-H4 CARs specifically react against B7H4+ ovarian cancer cells. FIG. 15B demonstrates differential B7H4 scFv CAR recognition of varying B7H4-expressing solid tumor cell lines and a lymphoma tumor cell line.

FIG. 16A is an image demonstrating that B7-H4 CAR transduced T cells are reactive against macrophages expressing differential levels of B7H4. FIG. 16B is an image demonstrating that #68 B7H4 CAR is comparable to the well-established anti-CD19 CAR in response to the respective tumor antigen.

FIGS. 17A-7B are a series of images demonstrating the inhibition of B7-H4 CARs. FIG. 17A is a set of images demonstrating that B7-H4 CAR T cells are not inhibited by immobilized B7-H4 protein.

FIG. 19 is an image demonstrating that 68scFv B7H4 CAR MIP1a cytokine secretion is not diminished as a result of B7-H4 CAR-B7H4 Ag signaling.

DETAILED DESCRIPTION

Figure 1A:
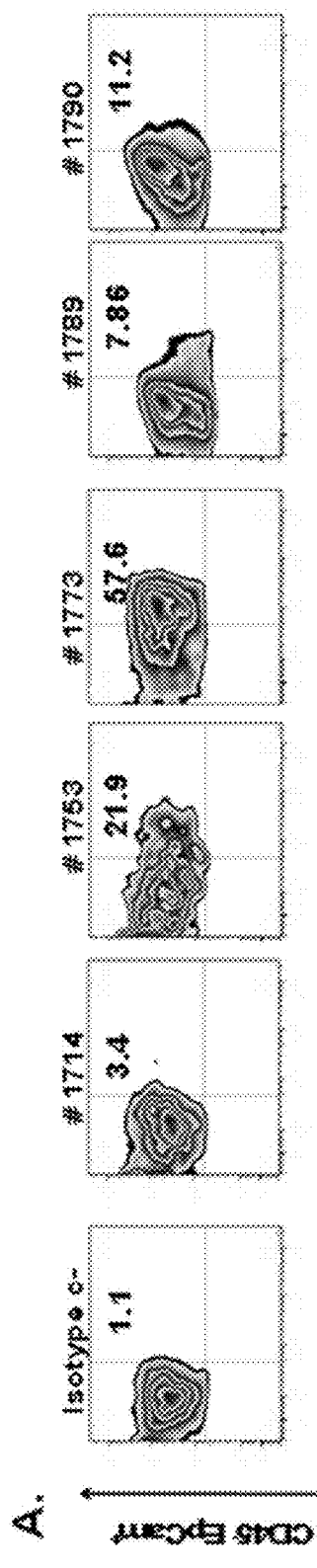
FIGS. 1A-1B are a series of images showing flow cytometry analysis of B7-H4 cell surface expression on ovarian cancer samples. PE-labeled anti-B7-H4 mAb staining of CD45-EpCam+ tumor cells (FIG. 1A) and CD45+CD14+ monocytes (FIG. 1B) from 5 ovarian cancer patients.

The present invention is based partly on the identification of human-derived antibodies that target B7-H4. The antibodies of the invention are used for diagnostic and in vivo therapeutic applications. In one embodiment, the antibodies of the invention specifically bind to B7-H4.

In another embodiment, the antibodies of the invention block the inhibition of T cell proliferation. In yet another embodiment, the anti-B7-H4 antibodies of the invention reverse T-cell inhibition mediated by a B7-H4 signalling. In one embodiment, the antibodies block B7-H4-dependent T cell inhibition.

In another embodiment, the antibodies of the invention restore T cell proliferation against tumor cells in the presence of macrophages and hence are a useful therapeutic composition against cancer. For example, blocking B7-H4 using an antibody of the invention overcomes antigen-specific T cell inhibition mediated by B7-H4 expressed on the tumor cell surface.

In one embodiment, the antibodies of the invention are scFv antibodies. In some embodiments, the antibodies of the invention are used for diagnosing the presence of B7-H4 in a biological sample.

In one embodiment, the antibodies of the invention are used for therapy against a disease, disorder or condition associated with dysregulation of B7-H4 expression. In one embodiment, the antibodies of the invention are used for cancer therapy against cancers associated with dysregulated expression of B7-H4.

The present invention relates generally to the treatment of a patient having a cancer associated with dysregulated expression of B7-H4, or at risk of having a cancer associated with dysregulated expression of B7-H4, using cellular infusion. In one embodiment, lymphocyte in fusion, preferably autologous lymphocyte infusion is used in the treatment.

In one embodiment, PBMCs are collected from a patient in need of treatment and T cells therefrom are engineered and expanded using the methods described herein and then infused back into the patient. The invention is not limited to a particular cell or cell type. Rather, any cell or cell type can be engineered and expanded using the methods described herein and then infused back into the patient.

The present invention also relates generally to the use of T cells engineered to express a Chimeric Antigen Receptor (CAR). CARs combine an antigen recognition domain of a specific antibody with an intracellular signaling molecule. For example, in some embodiments, the intracellular signaling molecule includes, but is not limited to, CD3-zeta chain, 4-1BB and CD28 signaling modules and combinations thereof. Preferably, the antigen recognition domain binds to B7-H4. More preferably, the antigen recognition domain comprises a fully human anti-B7-H4. Accordingly, the invention provides a fully human anti-B7-H4-CAR engineered into a T cell and methods of their use for adoptive therapy.

In one embodiment, the invention includes autologous cells that are transfected with a vector comprising a fully-human anti-B7-H4 CAR transgene. Preferably, the vector is a retroviral vector. More preferably, the vector is a self-inactivating lentiviral vector as described elsewhere herein.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "autoimmune disease" as used herein is defined as a disorder that results from an autoimmune response. An autoimmune disease is the result of an inappropriate and excessive response to a self-antigen. Examples of autoimmune diseases include but are not limited to, Addision's disease, alopecia greata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

As used herein, the term "B7-H4" refers to B7-H4 from any mammalian species and the term "hB7-H4" refers to human B7-H4. Further details on B7-H4 polypeptides and nucleic acids are provided in U.S. Pat. No. 6,891,030, the disclosure of which is incorporated herein by reference in its entirety. The nucleotide and amino acid sequences of hB7-H4 can be found in GenBank under Accession Nos. AY280972 and AAP37283, respectively. B7-H4 is a negative regulator of T cell-mediated immunity.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for the ability to bind B7-H4 using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83. A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "dysregulated" when used in the context of the level of expression or activity of B7-H4 refers to the level of expression or activity that is different from the expression level or activity of B7-H4 in an otherwise identical healthy animal, organism, tissue, cell or component thereof. The term "dysregulated" also refers to the altered regulation of the level of expression and activity of B7-H4 compared to the regulation in an otherwise identical healthy animal, organism, tissue, cell or component thereof "Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell. An example of a "cell surface receptor" is human B7-H4.

"Single chain antibodies" refer to antibodies formed by recombinant DNA techniques in which immunoglobulin heavy and light chain fragments are linked to the Fv region via an engineered span of amino acids. Various methods of generating single chain antibodies are known, including those described in U.S. Pat. No. 4,694,778; Bird (1988) Science 242:423-442; Huston et al. (1988) Proc. Natl. Acad. Sci. USA 85:5879-5883; Ward et al. (1989) Nature 334: 54454; Skerra et al. (1988) Science 242:1038-1041.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-$\beta$, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides isolated antibodies, particularly human antibodies that bind specifically to B7-H4. In certain embodiments, the antibodies of the invention comprise particular structural features such as CDR regions comprising particular amino acid sequences. The invention also provides methods of making such antibodies.

In one embodiment, the invention provides a number of antibodies or fragments thereof engineered for enhanced binding to a B7-H4 protein expressed on a cell surface. In another embodiment such antibody fragments are functional in that they provide a biological response including but is not limited to, activation of an immune response, inhibition of signal-transduction origination from its target antigen, inhibition of kinase activity, and the like, as will be understood by a skilled artisan. Preferably, the antibodies and fragments thereof of the invention can block the inhibition of T cell proliferation. In yet another embodiment, the anti-B7-H4 antibodies of the invention can reverse T-cell inhibition mediated by a B7-H4 signalling. In yet another one embodiment, the antibodies can block B7-H4-dependent T cell inhibition.

In some embodiments, the antibodies of the invention are incorporated into an immunoconjugate, a chimeric antigen receptor (CAR), a pharmaceutical composition, and the like. Accordingly, the present invention provides compositions and methods for treating, among other diseases, cancer or any malignancy or autoimmune disease in which expression of B7-H4 is dysregulated.

In one embodiment, the invention provides a cell (e.g., T cell) engineered to express a chimeric antigen receptor (CAR) wherein the CAR T cell exhibits an antitumor property. A preferred antigen is B7-H4. In one embodiment, the antigen recognition domain of the CAR comprises a fully human anti-B7-H4. Accordingly, the invention provides a fully human anti-B7-H4-CAR engineered into a T cell and methods of their use for adoptive therapy.

In one embodiment, the anti-B7-H4-CAR comprises one or more intracellular domain selected from the group of a CD137 (4-1BB) signaling domain, a CD28 signaling domain, a CD3zeta signal domain, and any combination thereof. This is because the present invention is partly based on the discovery that CAR-mediated T-cell responses can be further enhanced with the addition of costimulatory domains.

Anti-B7-H4 Antibodies

The antibodies of the invention are characterized by particular functional features or properties of the antibodies. For example, the antibodies bind specifically to human B7-H4. In one embodiment, the invention relates to an isolated human antibody or functional fragment thereof, wherein the antibody specifically binds to a B7-H4 protein or fragment thereof, wherein the antibody or functional fragment thereof is encoded by an amino acid sequence comprising a sequence selected from the group of SEQ ID NO: 1, SEQ ID NO: 2, SEQ ID NO: 3, and SEQ ID NO: 2.

In one embodiment, the anti-B7H4 scFv clone 56 polypeptide is encoded by the amino acid sequence set forth in SEQ ID NO: 1. In another embodiment, the nucleic acid sequence encoding the anti-B7H4 scFv clone 56 polypeptide is set forth in SEQ ID NO: 5.

In one embodiment, the anti-B7H4 scFv clone 26 polypeptide is encoded by the amino acid sequence set forth in SEQ ID NO: 2. In another embodiment, the nucleic acid sequence encoding the anti-B7H4 scFv clone 26 polypeptide is set forth in SEQ ID NO: 6.

In one embodiment, the anti-B7H4 scFv clone 3#54 (also referred herein as anti-B7H4 scFv clone 54) polypeptide is encoded by the amino acid sequence set forth in SEQ ID NO: 3. In another embodiment, the nucleic acid sequence encoding the anti-B7H4 scFv clone 3#54 polypeptide is set forth in SEQ ID NO: 7.

In one embodiment, the anti-B7H4 scFv clone 3#68 (also referred herein as anti-B7H4 scFv clone 54) polypeptide is encoded by the amino acid sequence set forth in SEQ ID NO: 4. In another embodiment, the nucleic acid sequence encoding the anti-B7H4 scFv clone 3#68 polypeptide is set forth in SEQ ID NO: 8.

In another embodiment, the invention relates to a recombinant B7-H4 protein, wherein the recombinant protein is encoded by the amino acid sequence comprising the sequence set forth in SEQ ID NO: 9. In another embodiment, the nucleic acid sequence encoding the recombinant B7-H4 protein is set forth in SEQ ID NO: 10.

In one embodiment, the antibody fragment provided herein is a single chain variable fragment (scFv). In another embodiment, the antibodies of the invention may exist in a variety of other forms including, for example, Fv, Fab, and (Fab')$_2$, as well as bi-functional (i.e. bi-specific) hybrid antibodies (e.g., Lanzavecchia et al., Eur. J. Immunol. 17, 105 (1987)). In one embodiment, the antibodies and fragments thereof of the invention binds a B7-H4 protein with wild-type or enhanced affinity.

In one embodiment, the anti-B7-H4 scFvs provided herein are from human origin. In another embodiment, the anti-B7-H4 scFvs provided herein were isolated from a yeast-display library of antibody fragments generated from B cells isolated from ascites of ovarian cancer patients. In another embodiment, the anti-B7-H4 scFvs are screened using a recombinant B7-H4 protein such as one exemplified by SEQ ID NO: 9. In another embodiment, the anti-B7-H4 scFvs provided herein are tested in in vitro co-culture model systems of macrophages, T cells and tumor cells. In another embodiment, the anti-B7-H4 scFvs provided herein have the advantage that they can bind B7-H4 expressed on the surface of both, monocytes and tumor cells such as macrophages and ovarian cancer cells.

In one embodiment, an antibody of the invention comprises heavy and light chain variable regions comprising amino acid sequences that are homologous to the amino acid sequences of the preferred antibodies described herein, and wherein the antibodies retain the desired functional properties of the anti-B7-H4 antibodies of the invention.

In some embodiments, the antibody of the invention is further prepared using an antibody having one or more of the VH and/or VL sequences disclosed herein can be used as starting material to engineer a modified antibody, which modified antibody may have altered properties as compared to the starting antibody. In various embodiments, the antibody is engineered by modifying one or more amino acids within one or both variable regions (i.e., VH and/or VL), for example within one or more CDR regions and/or within one or more framework regions. Additionally or alternatively, an antibody is engineered by modifying residues within the constant region(s), for example to alter the effector function(s) of the antibody.

Methods

In one embodiment, scFvs provided herein are used to detect or target B7-H4, thus permitting diagnostic tests in vitro and/or in vivo (imaging), as well as the production of targeted therapeutics. In some instances, the antibodies of the invention are coupled with therapeutic reagents, for example, coupled onto nanoparticles with payload, or as a chimeric antigen receptor (CAR) for T cell therapy. Hence, because of its functional properties in vitro, scFvs provided herein can also be used in vivo as a naked reagent to boost anti-tumor immunity.

In one embodiment, the invention relates to a method of diagnosing a B7-H4-related disease in a subject, the method comprising the step of a) administering to a subject an effective amount of composition comprising an anti-B7-H4 antibody or fragment thereof operably linked to a labeling agent, b) obtaining a biological sample from the subject, c) detecting binding of the composition to the biological sample, d) wherein detecting the binding of the composition to the biological sample from the subject is indicative of the subject having a B7-H4-related disease, and wherein the antibody or fragment thereof is encoded by the amino acid sequence comprising SEQ ID NO: 1, SEQ ID NO: 2, SEQ ID NO: 3, or SEQ ID NO: 4.

In another embodiment, the invention relates to a method of diagnosing a B7-H4-related disease in a subject, the method comprising the step of a) obtaining a biological sample from the subject b) contacting the sample with an effective amount of a composition comprising an anti-B7-H4 antibody or fragment thereof operably linked to a labeling agent, c) detecting binding of the composition to the biological sample, d) wherein detecting the binding of the composition to the biological sample from the subject is indicative of the subject having a B7-H4-related disease, and wherein the antibody or fragment thereof is encoded by the amino acid sequence comprising SEQ ID NO: 1, SEQ ID NO: 2, SEQ ID NO: 3, or SEQ ID NO: 4.

In one embodiment, the invention includes a method of inhibiting, suppressing or preventing immunosuppression of an anti-tumor or anti-cancer immune response in a subject, the method comprising administering to the subject an effective amount of a composition comprising an isolated anti-B7-H4 antibody of fragment thereof, wherein the antibody or fragment thereof is encoded by the amino acid sequence comprising SEQ ID NO: 1, SEQ ID NO: 2, SEQ ID NO: 3, or SEQ ID NO: 4. In another embodiment, the inhibition of immunosuppression prevents the interaction between macrophages expressing B7-H4 protein and T cells that would otherwise function to effect an anti-tumor response. Therefore, in another embodiment, inhibiting the interaction between macrophages and T cells inhibits immunosuppression of the subject's anti-tumor immune response.

In one embodiment, the invention includes a method of treating a cancer or a tumor growth, the method comprising the step of administering to a subject an effective amount of a composition comprising an isolated anti-B7-H4 antibody or fragment thereof, wherein administering the composition blocks a tumor-associated macrophage- or tumor cell-mediated immunosuppression of an anti-tumor response and enables activation of an anti-tumor response, wherein the antibody or fragment thereof is encoded by the amino acid sequence comprising SEQ ID NO: 1, SEQ ID NO: 2, SEQ ID NO: 3, or SEQ ID NO: 4.

In one embodiment, the invention provides a method of preventing a cancer metastasis, the method comprising the step of administering to a subject a composition comprising an anti-B7-H4 antibody or fragment thereof, wherein administering the antibody or fragment thereof blocks a tumor-associated macrophage- or tumor cell-mediated immunosuppression of an anti-tumor response and prevents the cancer metastasis, wherein the antibody or fragment thereof is encoded by the amino acid sequence comprising SEQ ID NO: 1, SEQ ID NO: 2, SEQ ID NO: 3, or SEQ ID NO: 4.

In another embodiment, the invention provides a method of blocking T-cell inhibition mediated by a B7-H4-expressing cell and altering the tumor microenvironment to inhibit tumor growth in a subject, the method comprising the step of administering to the subject an effective amount of a composition comprising an isolated anti-B7-H4 antibody or fragment thereof, wherein the antibody or fragment thereof is encoded by the amino acid sequence comprising SEQ ID NO: 1, SEQ ID NO: 2, SEQ ID NO: 3, or SEQ ID NO: 4.

In one embodiment, provided herein is a method of down-regulating the expression of a B7-H4 receptor or protein on the cell surface comprising contacting the receptor or protein with an B7-H4-specific antibody or fragment thereof, wherein the antibody or fragment thereof is encoded by the amino acid sequence comprising SEQ ID NO: 1, SEQ ID NO: 2, SEQ ID NO: 3, or SEQ ID NO: 4. It is to be understood by a skilled artisan that a specifically desired level of down-regulation can be achieved by contacting the B7-H4 receptor or protein provided herein, with an empirically determined dose of the anti-B7-H4 antibody or fragment thereof. In another embodiment, the term "downregulation" refers to inhibition or reduction of expression of the cell-surface B7-H4 protein, resulting in a preventive, diagnostic or therapeutic effect. In another embodiment, the down-regulation is two-fold, three-fold, five-fold or higher. In another embodiment, the signaling pathway starting at the oncogenic receptor that leads to the expression of more oncogenic receptor is down-regulated upon contacting the receptor with the antibody or fragment thereof of the invention.

In one embodiment, the invention provides a method of blocking an interaction between a receptor and a ligand comprising contacting the receptor with an B7-H4-specific antibody or fragment thereof, wherein the antibody or fragment thereof is encoded by the amino acid sequence comprising SEQ ID NO: 1, SEQ ID NO: 2, SEQ ID NO: 3, or SEQ ID NO: 4. In another embodiment, inhibiting the interaction amongst tumor cells and macrophages that express B7-H4 on their surface, and T cells, inhibits immunosuppression of the subject's anti-tumor immune response. In another embodiment, the immune response is a cell-mediated anti-tumor immune response, where in another embodiment the immune response is a T-cell mediated immune response. In another embodiment, the T-cell mediated immune response is a CD4 or a CD8 T-cell immune response.

In one embodiment, the invention provides a method of delivering a biologically active agent to a cell expressing B7-H4 on its surface, the method comprising contacting the cell with a bioconjugate composition comprising an anti- B7-H4 antibody or fragment thereof operably linked to the biologically active agent, wherein the antibody or fragment thereof has an amino acid sequence encoded by the amino acid sequence comprising SEQ ID NO: 1, SEQ ID NO: 2, SEQ ID NO: 3, or SEQ ID NO: 4. In another embodiment, the method further comprises the delivery of one or more biologically active agents. In another embodiment, the biologically active agent is a cytotoxic agent, a chemotherapeutic agent, a cytokine, a growth inhibitory agent, an anti-hormonal agent, a kinase inhibitor, an anti-angiogenic agent, a cardioprotectants, a toxin, a radioisotope, or a combination thereof.

In one embodiment, the method provides a method of labeling a cell expressing B7-H4 on its cell surface, the method comprising the step of contacting the cell with a bioconjugate composition comprising an anti-B7-H4 antibody or fragment thereof operably linked to a labeling agent, wherein the antibody or fragment thereof is encoded by an amino acid sequence comprising SEQ ID NO: 1, SEQ ID NO: 2, SEQ ID NO: 3, or SEQ ID NO: 4. In another embodiment, the labeling is carried out in vivo. In another embodiment, the labeling enables imaging the cell, where in another embodiment, the labeling enables imaging the cell and monitoring the progression of a disease related to B7-H4 expression on the surface of the cell. In another embodiment the cell is a tumor cell or a tumor-associated macrophage (TAM). In one embodiment, TAMs inhibit T cell proliferation and activation in a B7H4-dependent manner.

In one embodiment, the invention provides a method of restoring T-cell replication associated with an anti-tumor immune response in a subject following tumor associated macrophage (TAM)-mediated immune suppression in the subject, the method comprising the step of administering to the subject a composition comprising an isolated anti-B7-H4 antibody or fragment thereof, wherein the antibody or fragment thereof is encoded by an amino acid sequence comprising SEQ ID NO: 1, SEQ ID NO: 2, SEQ ID NO: 3, or SEQ ID NO: 4.

In one embodiment, the invention provides a method of monitoring a tumor cell frequency in a subject having a tumor growth, the method comprising the step of a) obtaining a biological sample from the subject, b) contacting the biological sample with a bioconjugate composition comprising the anti-B7-H4-antibody or fragment thereof operably linked to a labeling agent, and c) monitoring the progression of cell surface expression of B7-H4 in a biological sample, wherein the antibody or fragment thereof is encoded by an amino acid sequence comprising SEQ ID NO: 1, SEQ ID NO: 2, SEQ ID NO: 3, or SEQ ID NO: 4.

In another embodiment, the labeling agent provided herein is a nanoparticle quantum dot, a fluorophore, a cyanide, a radioactively-labeled peptide, a magnetic nanoparticle, a chromophore, or a localization marker. In another embodiment, the labeling is carried out in vivo and enables the imaging of the cell.

In another embodiment, imaging of cells includes any type of imaging technique known in the art including in vivo and in vitro imaging. In another embodiment, the imaging is optical imaging, fluorescence imaging, scattering imaging, time-lapse imaging, live imaging, colorimetric imaging, electron microscopy imaging, magnetic resonance imaging, or a combination thereof.

In another embodiment, the invention relates to a method of effecting a therapeutic T-cell mediated anti-tumor immune response in a subject having an anti-tumor immune response suppression, wherein the immune suppression is mediated by a B7-H4-expressing cell in the subject, the method comprising the step of administering to the subject a composition comprising a recombinant T-cell specific for the B7-H4-expressing cell, wherein the recombinant T-cell comprises a chimeric antigen receptor comprising a) an ectodomain comprising an anti-B7-H4 antibody or fragment thereof, b) a transmembrane domain, and c) a T-cell receptor endodomain, wherein the antibody or fragment thereof is encoded by the amino acid sequence comprising SEQ ID NO: 1, SEQ ID NO: 2, SEQ ID NO: 3, or SEQ ID NO: 4.

CAR Composition

The present invention encompasses a recombinant DNA construct comprising sequences of an antibody of the invention that binds specifically to human B7-H4, wherein the sequence of the antibody or a fragment thereof is operably linked to the nucleic acid sequence of an intracellular domain. The intracellular domain or otherwise the cytoplasmic domain comprises, a costimulatory signaling region and/or a zeta chain portion. The costimulatory signaling region refers to a portion of the CAR comprising the intracellular domain of a costimulatory molecule. Costimulatory molecules are cell surface molecules other than antigens receptors or their ligands that are required for an efficient response of lymphocytes to antigen.

The present invention encompasses a recombinant DNA construct comprising sequences of a fully human CAR, wherein the sequence comprises the nucleic acid sequence of a B7-H4 binding domain operably linked to the nucleic acid sequence of an intracellular domain. An exemplary intracellular domain that can be used in the CAR includes but is not limited to the intracellular domain of CD3-zeta, CD28, 4-1BB, and the like. In some instances, the CAR can comprise any combination of CD3-zeta, CD28, 4-1BB, and the like.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

Antigen Binding Moiety

In one embodiment, the CAR of the invention comprises a target-specific binding element otherwise referred to as an antigen binding moiety. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR-mediated T-cell response can be directed to an antigen of interest by way of engineering a desired antigen into the CAR. In the context of the present invention, "tumor antigen" or "hyperproliferative disorder antigen" or "antigen associated with a hyperproliferative disorder" refers to antigens that are common to specific hyperproliferative disorders. In certain aspects, the hyperproliferative disorder antigens of the present invention are derived from, cancers including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

In one embodiment, the tumor antigen of the present invention comprises one or more antigenic cancer epitopes immunologically recognized by tumor infiltrating lymphocytes (TIL) derived from a cancer tumor of a mammal.

In a preferred embodiment, the antigen binding moiety portion of the CAR targets B7-H4, preferably human B7-H4.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or a fragment thereof. Thus, in one embodiment, the antigen biding domain portion comprises a human antibody or a fragment thereof.

For in vivo use of antibodies in humans, it may be preferable to use human antibodies. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO98/16654, WO 96/34096, WO 96/33735, and WO 91/10741; each of which is incorporated herein by reference in its entirety. A human antibody can also be an antibody wherein the heavy and light chains are encoded by a nucleotide sequence derived from one or more sources of human DNA.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Anti-B7-H4 antibodies directed against the human B7-H4 antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., Proc. Natl. Acad. Sci. USA, 90:2551 (1993); Jakobovits et al., Nature, 362:255-258 (1993); Bruggermann et al., Year in Immunol., 7:33 (1993); and Duchosal et al., Nature, 355:258 (1992).

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Alternatively, in some embodiments, a non-human antibody is humanized, where specific sequences or regions of the antibody are modified to increase similarity to an antibody naturally produced in a human. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16): 10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some instances, a human scFv may also be derived from a yeast display library.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

In some embodiments, the antibody is humanized with retention of high affinity for the target antigen and other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody, i.e., in the present invention, the ability to bind human B7-H4. However, using certain methods of humanization, the affinity and/or specificity of binding of the antibody for human B7-H4 may be increased using methods of "directed evolution," as described by Wu et al., J. Mol. Biol., 294:151 (1999), the contents of which are incorporated herein by reference herein in their entirety.

Transmembrane Domain

With respect to the transmembrane domain, in various embodiments, the CAR is designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Cytoplasmic Domain

The cytoplasmic domain or otherwise the intracellular signaling domain of the CAR of the invention is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in the CAR of the invention comprises a cytoplasmic signaling sequence derived from CD3-zeta.

In a preferred embodiment, the cytoplasmic domain of the CAR is designed to comprise the CD3-zeta signaling domain by itself or combined with any other desired cytoplasmic domain(s) useful in the context of the CAR of the invention. For example, the cytoplasmic domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Thus, while the invention in exemplified primarily with CD28 and 4-1BB as the co-stimulatory signaling element, other costimulatory elements are within the scope of the invention.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta and the signaling domain of CD28. In another embodiment, the cytoplasmic domain is designed to comprise the signaling domain of CD3-zeta and the signaling domain of 4-1BB.

Vectors

The present invention also provides vectors in which a DNA of the present invention is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

In brief summary, the expression of natural or synthetic nucleic acids encoding CARs is typically achieved by operably linking a nucleic acid encoding the CAR polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al., MOLECULAR CLONING: A LABORATORY MANUAL, volumes 1-3 ($3^{rd}$ ed., Cold Spring Harbor Press, NY 2001), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., MOLECULAR CLONING: A LABORATORY MANUAL volumes 1-3 (4th ed., Cold Spring Harbor Press, NY 2012).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Sources of T Cells

Prior to expansion and genetic modification, a source of T cells is obtained from a subject. The term "subject" is intended to include living organisms in which an immune response can be elicited (e.g., mammals). Examples of subjects include humans, dogs, cats, mice, rats, and transgenic species thereof. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD1 b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$. Alternatively, in certain embodiments, T regulatory cells are depleted by anti-C25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than $CD8^+$ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy such as agents that react with CD20, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566;

7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besangon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/

CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-$\gamma$, IL-4, IL-7, GM-CSF, IL-10, IL-12, IL-15, TGF$\beta$, and TNF-$\alpha$. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, $\alpha$-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one embodiment, the invention pertains to a method of inhibiting growth of a B7-H4-expressing tumor cell, comprising contacting the tumor cell with at least one antibody or a fragment thereof of the invention such that growth of the tumor cell is inhibited.

In one embodiment, the invention pertains to a method of inhibiting growth of a B7-H4-expressing tumor cell, comprising contacting the tumor cell with an anti-B7-H4 CAR T cell of the present invention such that growth of the tumor cell is inhibited.

In another aspect, the invention pertains to a method of treating cancer in a subject. The method comprises administering to the subject an antibody or a fragment of the invention or an anti-B7-H4 CAR T cell of the present invention such that the cancer is treated in the subject. Particularly preferred cancers for treatment are hepatocellular carcinomas, pancreatic cancers, ovarian cancers, stomach cancers, lung cancers and endometrial cancers. In still other embodiments, the cancer to be treated is selected from the group consisting of hepatocellular carcinomas, papillary serous ovarian adenocarcinomas, clear cell ovarian carcinomas, mixed Mullerian ovarian carcinomas, endometroid mucinous ovarian carcinomas, pancreatic adenocarcinomas, ductal pancreatic adenocarcinomas, uterine serous carcinomas, lung adenocarcinomas, extrahepatic bile duct carcinomas, gastric adenocarcinomas, esophageal adenocarcinomas, colorectal adenocarcinomas and breast adenocarcinomas.

The present invention includes a type of cellular therapy where T cells are genetically modified to express a chimeric antigen receptor (CAR) and the CAR T cell is infused to a recipient in need thereof. The infused cell is able to kill tumor cells in the recipient. Unlike antibody therapies, CAR-modified T cells are able to replicate in vivo resulting in long-term persistence that can lead to sustained tumor control. In various embodiments, the T cells administered to the patient, or their progeny, persist in the patient for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell to the patient.

Without wishing to be bound by any particular theory, the anti-tumor immunity response elicited by the CAR-modified T cells may be an active or a passive immune response. In another embodiment, the fully-human CAR transduced T cells exhibit specific proinflammatory cytokine secretion and potent cytolytic activity in response to human cancer cells expressing the B7-H4, resist soluble B7-H4 inhibition, mediate bystander killing and mediate regression of an established human tumor. For example, antigen-less tumor cells within a heterogeneous field of B7-H4-expressing tumor may be susceptible to indirect destruction by B7-H4-redirected T cells that has previously reacted against adjacent antigen-positive cancer cells.

The fully-human CAR-modified T cells of the invention may be a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of diseases, disorders and conditions associated with dysregulated expression of B7-H4. In certain embodiments, the cells of the invention are used in the treatment of patients at risk for developing diseases, disorders and conditions associated with dysregulated expression of B7-H4. Thus, the present invention provides methods for the treatment or prevention of diseases, disorders and conditions associated with dysregulated expression of B7-H4 comprising administering to a subject in need thereof, a therapeutically effective amount of the fully human CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

The administration of the subject compositions may be carried out in any convenient manner, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAM-PATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1: Anti-B7-H4 Antibodies

The following experiments were designed to isolate and characterize antibodies that bind to B7-H4. These antibodies are optimal for development for diagnostic and in vivo therapeutic applications.

The materials and methods employed in these experiments are now described.

Antibodies

Yeast-display scFv expression was detected with anti-cmyc mouse monoclonal antibody (mAb), 9E10 and Alexa-488 F(ab')2 fragment of goat anti-mouse IgG (H+L) (488 anti-IgG) or PE-Cy7 goat F(ab')2 anti-mouse IgG(H+L) (PE-Cu5 anti-IgG). Biotinylated antigen binding to yeast display scFv was detected with goat anti-biotin-FITC or streptavidin-PE. ScFv binding to cell lines was detected with APC-conjugated anti-V5 mouse mAb and scFv binding to plastic-immobilized antigen was detected by HRP-conjugated mouse anti-V5 mAb. Biobody binding to B7-H4-expresser cells was detected with APC-labeled streptavidin.

Identification of Anti-B7-H4 scFv

The yeast-display scFv library derived from ovarian cancer patients was first screened by magnetic and flow sorting for anti-B7-H4 scFv using progressively decreasing concentrations of human biotinylated B7-H4 recombinant protein (rhB7-H4). Briefly, the library was enriched magnetically 3 times for scFv that bound to 1 ug/ml biotinylated rhB7-H4, and two times flow sorted with 1 ug/ml and 0.5 ug/ml biotinylated rhB7-H4. Selected yeast-display scFv were flow sorted for c-myc/B7-H4 double positive clones. DNA plasmids were extracted from yeast display scFv fragments were amplified using primers allowing homologous recombination with the yeast secretion vector p416-BCCP. The primers used were: Forward shuffling primer: 5'-ggttctggtggtggaggttctggtggtggtggatctg-3'(SEQ ID NO: 11); Reverse shuffling primer: 5'-gagaccgaggagagggttaggga-taggcttaccgtcgaccaagtcttcttcagaaataagctt-3' (SEQ ID NO: 12). ScFv fragments and linearized p416-BCCP were co-transfected into YVH10 by chemical transformation. Soluble scFv screening for specific binding to biotinylated B7-H4 was performed by capture ELISA using high throughput purified yeast supernatants of 100 random transformants immobilized in amino plates. Binding to serial dilutions of biotinylated rB7-H4 or control protein was detected using streptavidin-HRP. Colorimetric signals were developed with TMB substrate solution quenched with sulfuric acid and read at 450 nm on a Fluoroskan deviations Sequencing of scFv clones 26 and 56 was identified 2 unique clones that were then produced and Ni purified.

Measurement of scFv Affinity by ELISA

To assess scFvs affinity, ELISA plates were coated with rhB7-H4 at two-fold decreasing concentrations from 0.4 to 0.05 µg/ml, in carbonate-bicarbonate buffer. After blocking with PBSM, wells were incubated with ten-fold serial dilutions of scFv, starting from 1 µM. ScFv binding to immobilized proteins was detected with HRP anti-V5. Colorimetric signals were then developed.

Flow Cytometry Analysis

Analysis of scFv expression by yeast was performed. Briefly, binding of anti-B7-H4 scFv and biobodies to B7-H4-expresser macrophages and tumor cells was evaluated Anti-B7-H4 scFv were preincubated for 30 min at RT with APC-anti-V5 at a ratio 1/1 and anti-B7-H4 biobodies were preincubated with FITC-labeled streptavidin beads. A non-relevant scFv or biobody was used as a negative control for binding.

Orthotopic Mouse Model of Ovarian Cancer

MOV1 mouse ovarian cancer cell line is derived from an ovarian cancer that spontaneously arises in female transgenic mice that express the transforming region of SV40 under control of the Mullerian inhibitory substance type II receptor gene promoter (Tg-MISIIR-Tag). MOV1 cell line expresses SV40 antigen. To emulate ovarian cancer mouse ovarian cancer cells, MOV1 were orthotopically injected in the ovarian bursa of NOD-Scid-γ null (NSG) mice. Four month-old multiparous females are anesthetized according to the protocol approved by the University of Pennsylvania Institutional Animal Care and Use Committee (IACUC). A dorsolateral incision on left caudal portion of the animal dorsum was made. The retroperitoneum is dissected to expose the left ovary using the forceps to grasp, retract, position, and secure the organ for injection. Five million MOV1 cells are injected in the ovarian bursa in a volume of 20 µl of PBS using an insulin syringe. Retroperitoneal incisions are closed, animals are administered antibiotics and fluids, and tumor growth is monitored by in vivo imaging.

Analysis of In Vivo Distribution of Anti-B7-H4 Biobodies by Confocal Microscopy

Anti-B7-H4 biobody-26 of high affinity is injected intravenously (IV) 3 weeks after tumor cell implantation. As control for the Enhanced Permeability and Retention (EPR) effect, the anti-B7-H4 biobodies of low affinity is used. Spleen, liver, kidney and ovaries are harvested 24 or 48 h after biobody injection and preserved in frozen tissue matrix OCT compound. Slides of 5 t thickness are cut from frozen sections, air dried 1 h at RT and fixed by immersion in cold 100% acetone 5 min. After 2 washes in PBS, slides are blocked for endogenous biotin by pre-treatment with avidin/biotin blocking solution (avidin-skim milk 0.001% in PBS). Anti-B7-H4 biobody binding are detected with rhodamine-conjugated streptavidin. MOV1 tumor cells derived from a Tg-MISIIR-TAg tumor express SV40 and thus could be detected with anti-SV40 Tag antibody (2 µg/ml) for 30 min at RT, followed by 1 µg/ml Alexa-488 goat anti-mouse IgG1κ for 30 min at RT. Slides are incubated with 1/2000 diluted DAPI for 30 min at RT to visualize the nuclei. Fluorescent signals are acquired by confocal analysis at 63× magnification.

The results of the experiments are now described.

Tumor Cells and Monocytes from Ascites and Solid Tumors of Ovarian Cancer Patients Express B7-H4 at the Cell Surfaces B7-H4 cell surface expression has been shown for tumor-associated macrophages but not in ovarian cancer cells. Without being bound by any particular theory, it is believed that tumor cell surface expression of B7-H4 permits targeting and suggests the existence of alternate immune inhibitory functions of ovarian tumor cells.

Figure 1B:
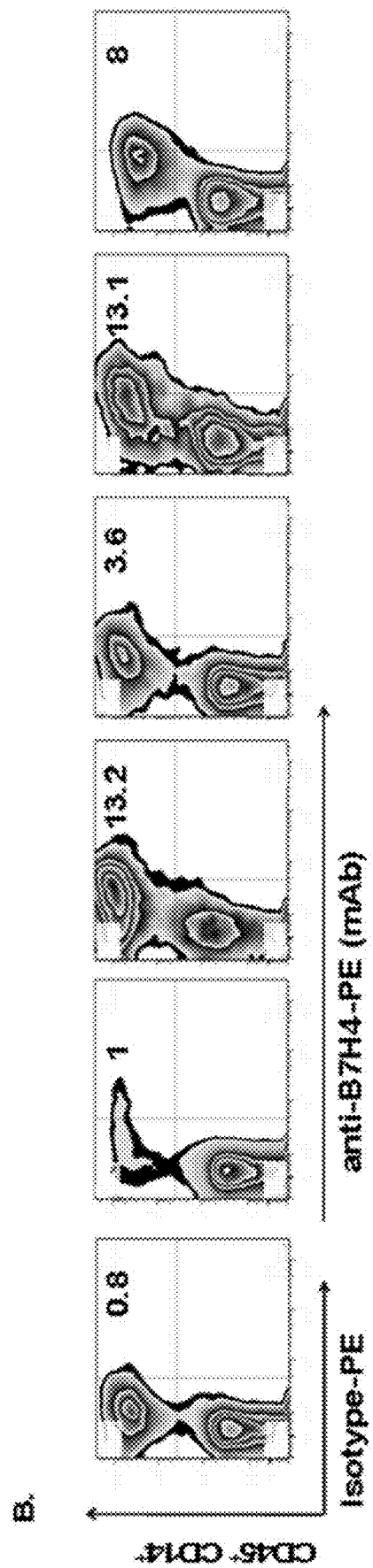

Analysis of B7-H4 surface expression on tumor cells using flow cytometry revealed that these tumor cells indeed expressed B7-H4 on the cell surface (FIGS. 1A-1B). Hence, it was confirmed that B7-H4 is expressed at the cell surface of fresh ovarian cancer cells (FIG. 1A) and monocytes (FIG. 1B).

Figures 2A, 2B:
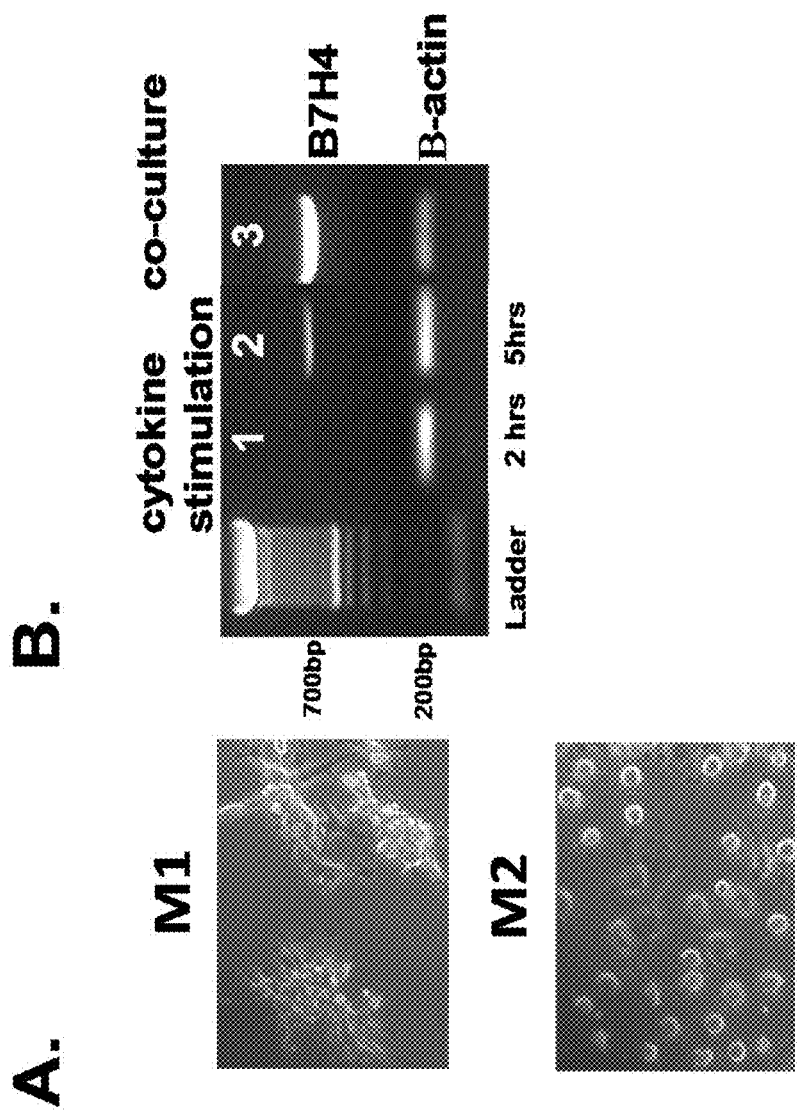
FIGS. 2A-2D are a series of images showing upregulation of B7-H4 on macrophages in vitro.
Figure 2D:
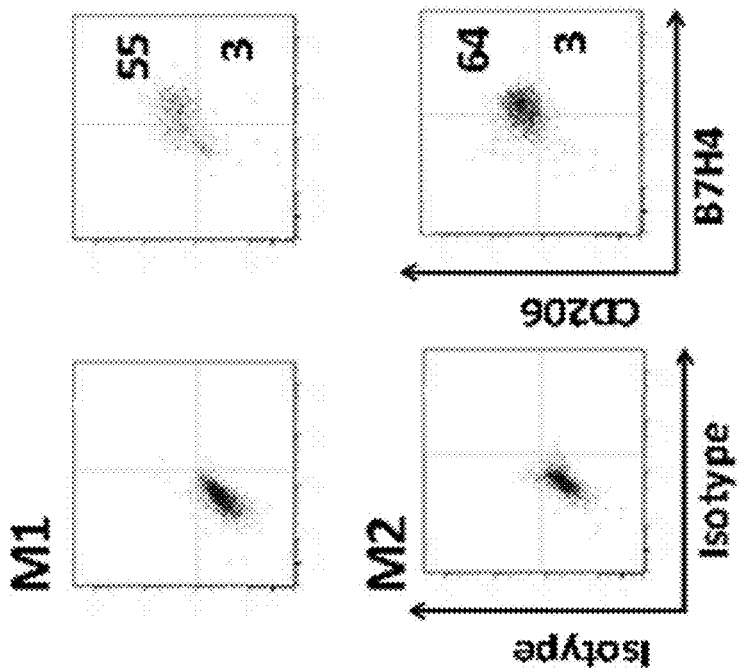
Figure 2C:
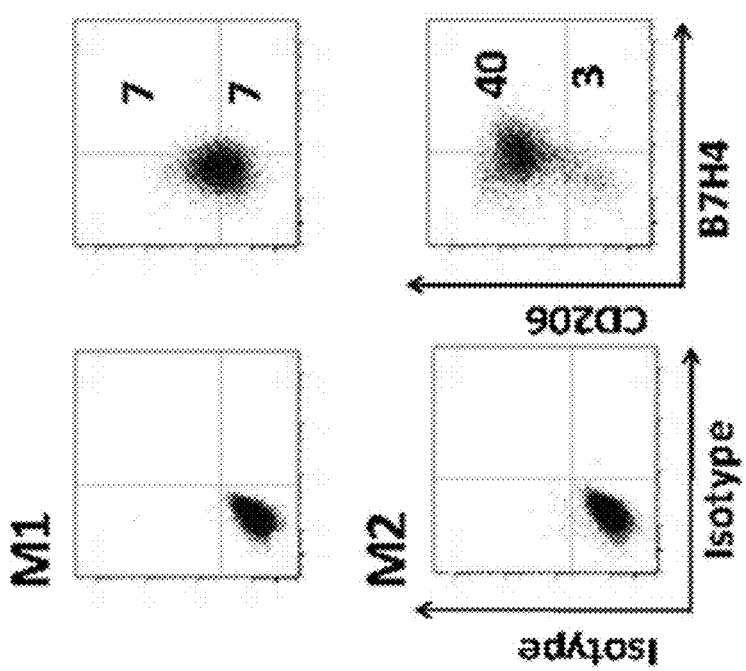

Macrophages Up-Regulate B7-H4 Expression after Co-Culture with Ovarian Cancer Cells Analysis of B7-H4 surface expression on monocytes from ascites and solid tumors from ovarian cancer patients using flow cytometry revealed that these tumor cells indeed expressed B7-H4 on the cell surface (FIGS. 2A-2D). Hence, it was confirmed that B7-H4 is expressed at the cell surface of macrophages freshly isolated from ovarian ascites or solid tumors (FIG. 2A), as well as of macrophages maturated in presence of IL4 and IL10 (FIG. 2B). In addition, it was demonstrated that co-culture with B7-H4 expresser OvCar3 tumor cell line also up-regulates the expression of B7-H4 (FIG. 2B).

Macrophages Strongly Up-Regulate B7-H4 Expression after Co-Culture with B7-H4+ Ovarian Cancer Cell Line In vitro model system of cell co-culture in transwell was carried out, allowing chemical exchanges between human monocyte-derived macrophages and human ovarian cancer cell line Ovcar3. Co-culture of macrophages with Ovcar3 polarized macrophages towards TAM phenotype.

Transwell co-culture of macrophages with tumor cells enables a superior up regulation of B7-H4 on macrophages compared to cytokine (IL4/IL10) stimulation. This model system allows for studying tumor cell induction of B7-H4 on macrophages.

Figure 3A:
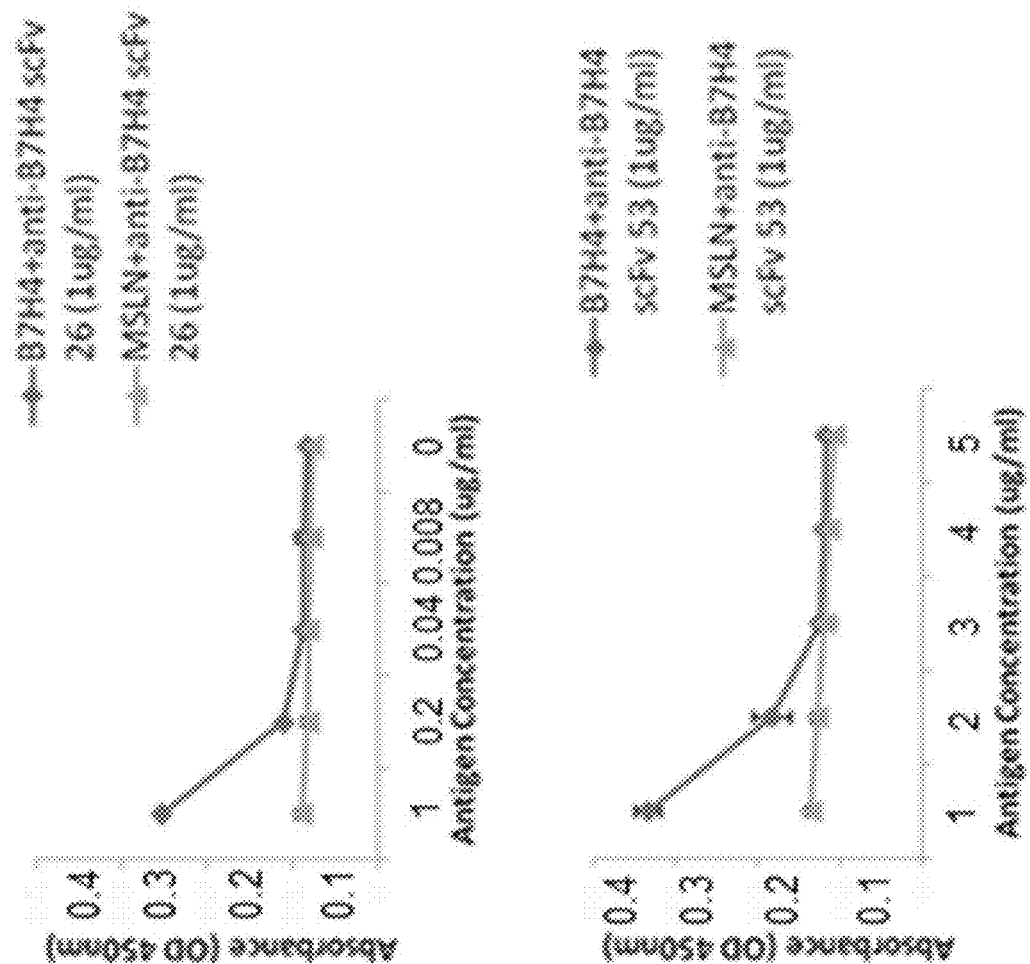
FIGS. 3A-3B are a series of images showing validation of anti-B7-H4 scFv.
Figure 3B:
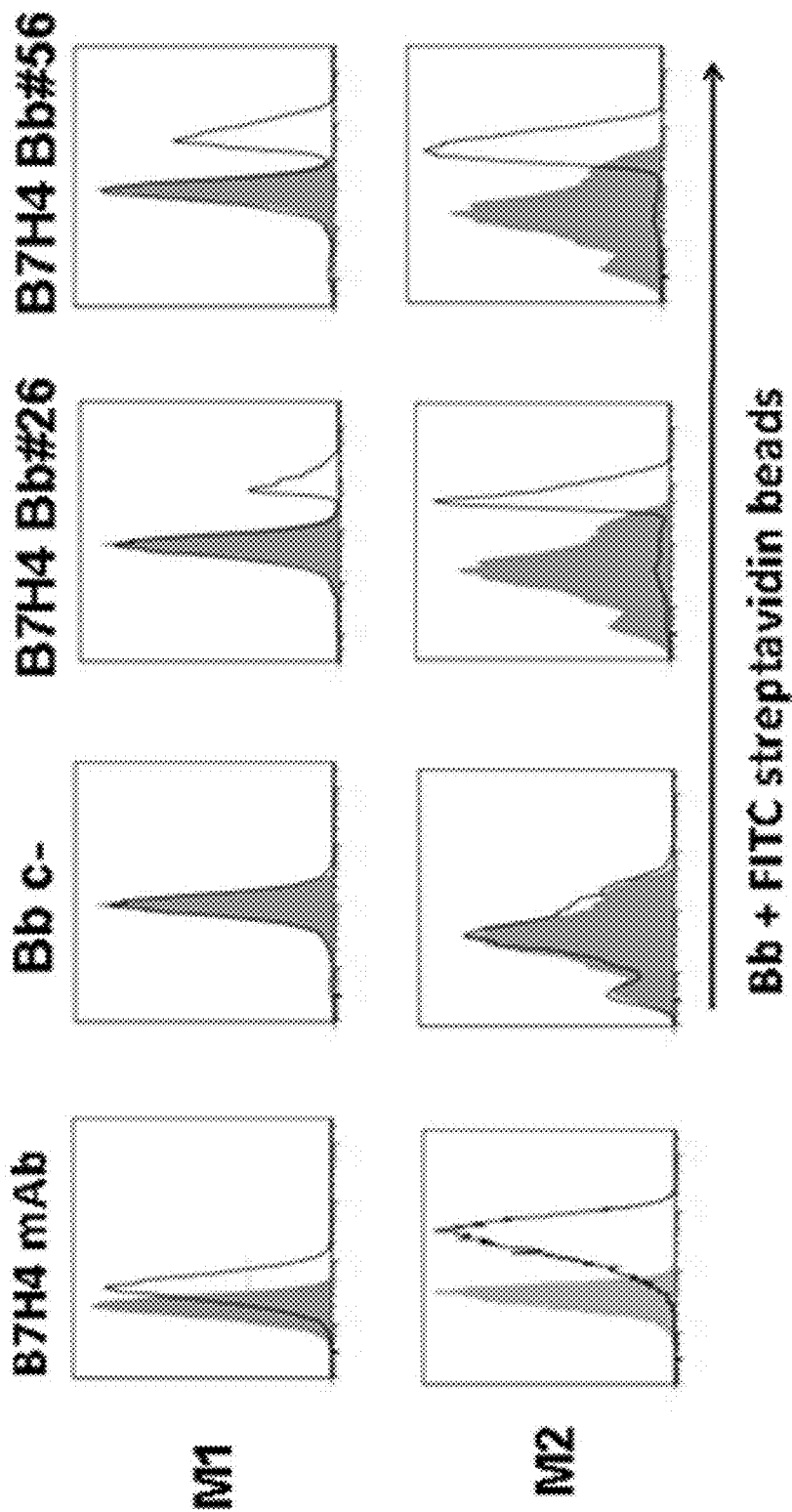
Figures 4A, 4B:
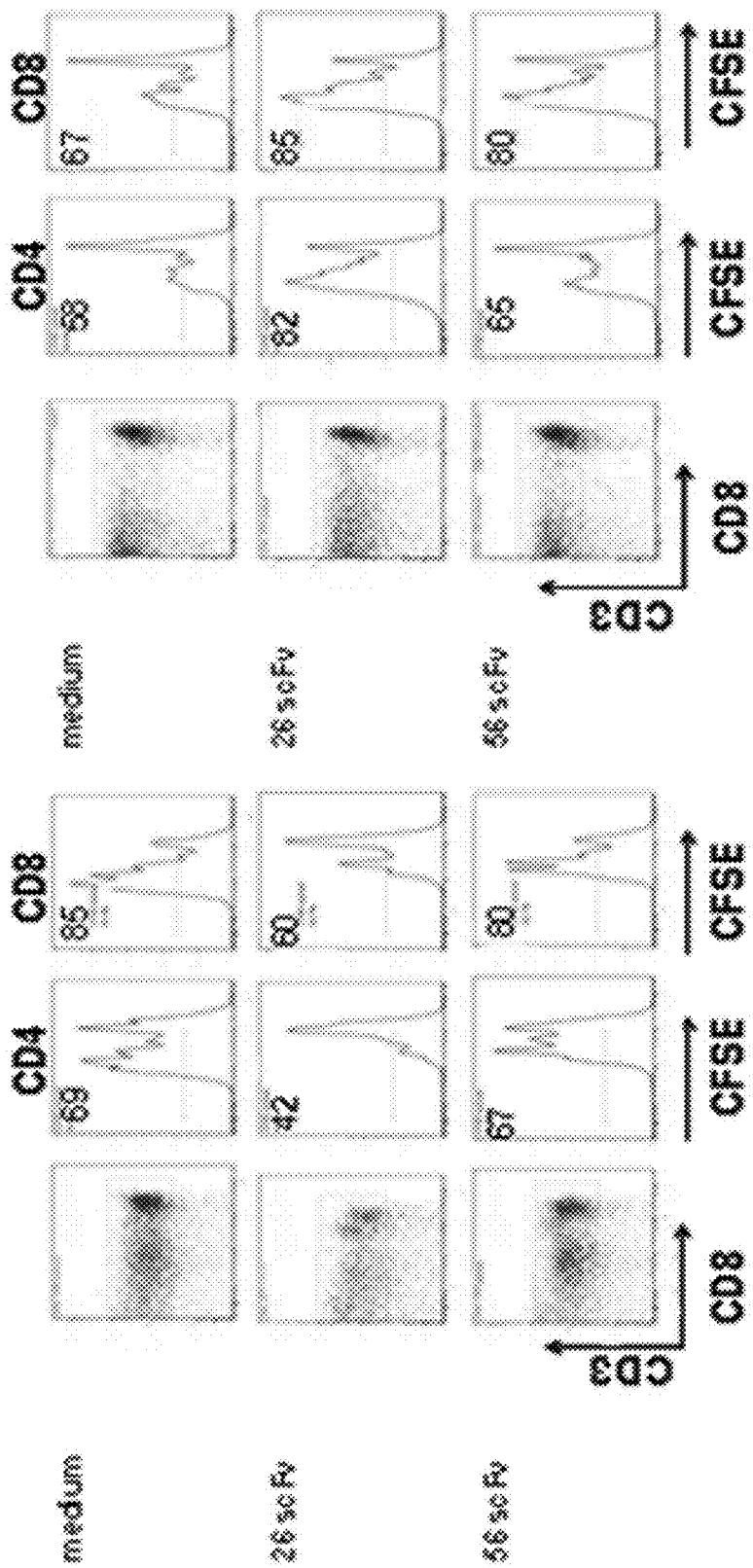
FIGS. 4A-4E are a series of images demonstrating blocking of B7-H4-mediated T cell suppression using anti-B7-H4 scFvs in vitro.
Figures 4C, 4D:
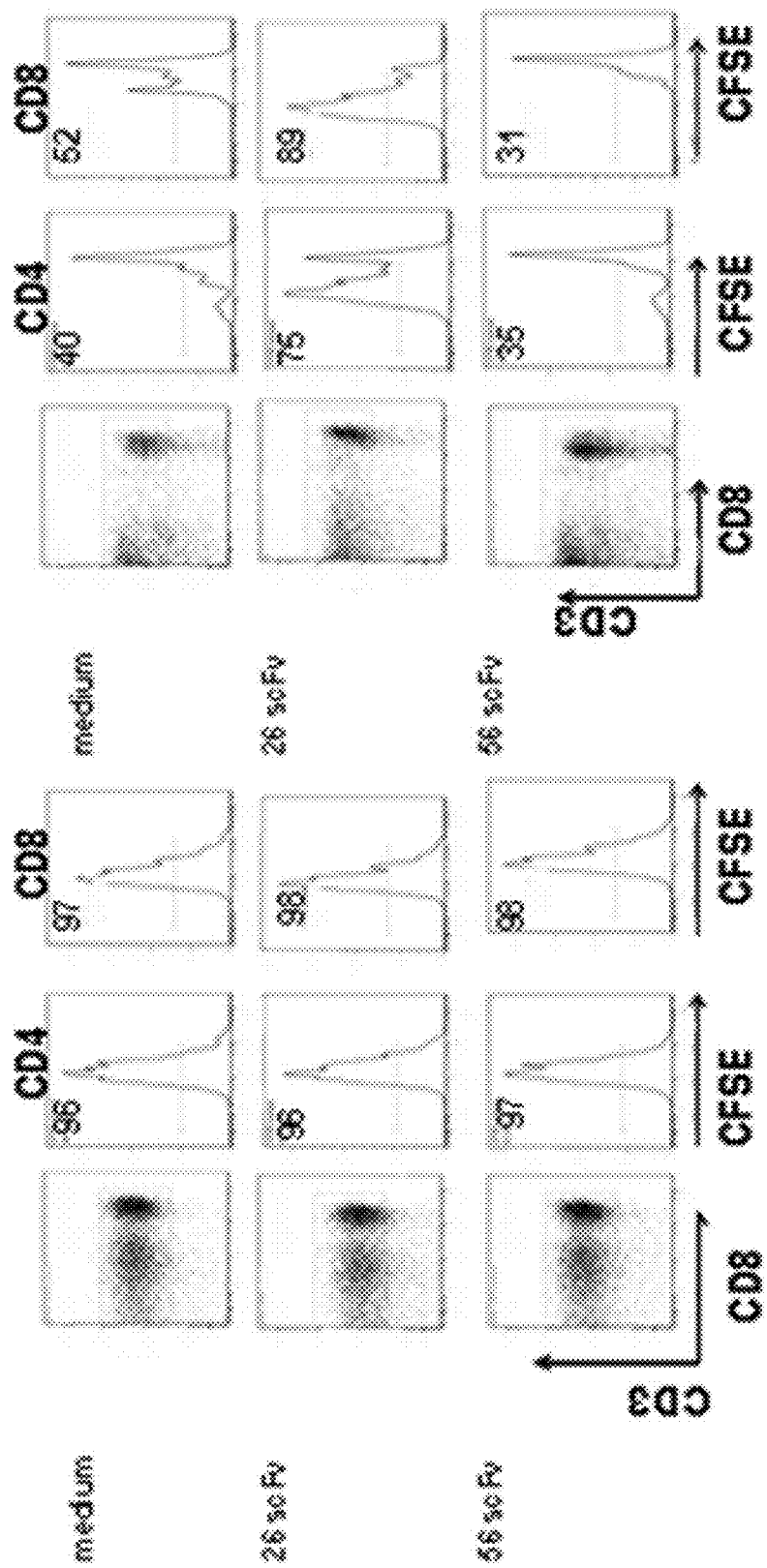
Figure 4E:
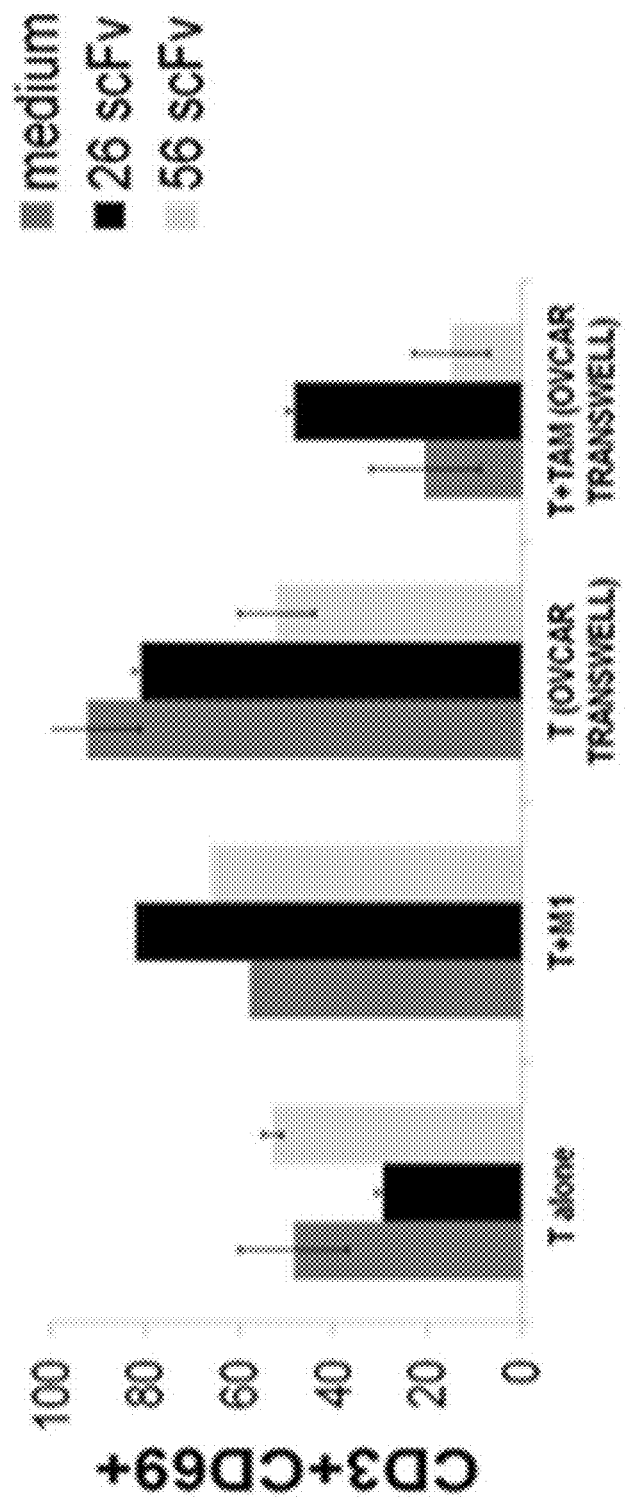

Isolation of Anti-B7-H4 Recombinant Antibodies (scFvs) from a Yeast-Display scFv Library B7-H4 extracellular domain was cloned from macrophages co-cultured with ovcar3 and expressed in mammalian cells. ScFvs against B7-H4 were isolated by screening a yeast-display scFv library. ScFvs were converted into soluble form and specific binding was validated on recombinant B7-H4 protein (FIG. 3A) and on macrophages (FIG. 3B).

These results demonstrate that the novel anti-B7-H4 biobodies in complex with streptavidin iron oxide FITC labeled beads are more sensitive than commercially available anti-B7-H4 mAb. In addition, it demonstrates that the ovcar5 cell line expresses B7-H4 since utilizing the novel scFv's B7-H4 can be detected even at low expression levels (ovcar5) that cannot be detected with commercial mAb anti-B7-H4.

The results further demonstrate that an established ovarian cancer cell line, OvCar3, expresses B7-H4 at the cell surface; and a sub-population of OvCar5 cell line also expresses B7-H4.

B7-H4 Expression on Macrophages and Tumor Cell's Frequency

After measuring the expression of B7-H4 on macrophages and the tumor cell's frequency, it was found that the two were positively correlated, in that B7-H4 expression on monocytes was correlated with the percentage of tumor cells in ovarian cancer samples.

Anti-B7-H4-Mediated Blockage of B7-H4-Mediated T Cell Suppression by Macrophages Promotes T Cell Proliferation It was further demonstrated that anti-B7-H4 clone scFv #26 could block B7-H4-mediated T cell suppression by macrophages and promote anti-tumor T cell proliferation (FIGS. 4A-4E).

Therefore, scFv 26, can unexpectedly restore T cell proliferation against tumor cells in presence of macrophages and hence can be a useful therapeutic composition against these tumor cells.

Example 2: Novel Human Anti-B7-H4 Recombinant Antibodies Overcome B7-H4-Mediated T-Cell Inhibition and Potentiate T Cell Anti-Tumor Responses B7-H4 (B7x/B7s), one of the most recently identified members of B7 superfamily, serves as an inhibitory modulator of T-cell responses. B7-H4 is expressed by various human cancers and B7-H4 expression by macrophages has been significantly correlated with advanced stages of ovarian cancer and with high numbers of tumor-infiltrating T regulatory cells. B7-H4 expressed at the surface of tumor-associated macrophages (TAMs) or surrogate APCs negatively regulates T cell activation, possibly through interaction with a putative ligand, and B7-H4 blocking by antisense oligonucleotides inhibited tumor-associated macrophages suppression and enabled anti-tumor T cells in vitro and in vivo. However, to this date, B7-H4 cell surface expression has been poorly understood.

The following experiments were designed to study cell surface expression of B7-H4 in samples from ovarian cancer ascites and solid tumors, as well as in human ovarian cancer cell lines after passage and short term culture. B7-H4 was expressed at the cell surface of tumor-infiltrating monocyte/macrophages and of freshly harvested Epcam$^+$ tumor cells from cancer patients or from xenograft mouse model, but the B7-H4 expression on tumor cells was downregulated after short term in vitro culture.

Four anti-B7-H4 recombinant antibodies (scFvs) were isolated by differential screenings of a yeast-display scFv library derived from human B lymphocytes from ovarian cancer patients. Three out of four anti-B7-H4 scFvs could reverse T-cell inhibition mediated by a B7-H4 recombinant protein, as demonstrated by IFN-γ secretion, CD69 expression and T cell proliferation in response to anti-CD3 stimulation. Furthermore, antigen-specific T cell responses were inhibited by B7-H4$^+$ antigen-loaded APCs or B7-H4$^+$ tumor cells (presentation in cis), and by B7-H4$^+$ APCs in presence of tumor cells (presentation in trans). The presence of anti-B7-H4 scFv 3#68 in antigen-specific T cell co-cultures with B7-H4$^+$ antigen-loaded APCs, B7-H4$^+$ tumor cells, or B7-H4$^+$TAMs and tumor cells, fully restored B7-H4-dependent inhibition. These data presented herein demonstrate that B7-H4 cell surface expression is inducible in vivo by the tumor microenvironment and show that blocking B7-H4 with an antibody restores anti-tumor T cell responses in vitro. Anti-B7-H4 scFvs of the invention can be used for immunotherapy against solid tumors. The materials and methods employed in these experiments are now described.

Human Samples

Ascites and solid tumors samples from ovarian cancer patients were obtained from the Ovarian Cancer Research Center's patient sample repository of the University of Pennsylvania. Purified T cells and monocytes from healthy donors were obtained from the Human Immunology Core of the University of Pennsylvania.

Human Ovarian Cancer Cell Lines

A1847, OVCAR3, C30, T2, 624, MDA231, OVCAR5 were obtained from ATCC. M2 macrophages are generated as previously described (Dangaj et al., 2011, PLoS One 6(12):e28386). EBV-B cells were kindly provided by Dr. Raj Somasundaram (Wistar Institute, Philadelphia, Pa.).

Xenograft Model of Ovarian Cancer

Balb/c nude mice were obtained from Charles River Laboratories. Mice of 6-8 weeks were injected intraperitoneally with 3×10$^6$ of OVCAR5 ovarian cancer cell line. Mice were sacrificed at 6-9 weeks after tumor implantation. Ascites and solid tumor samples were collected and analyzed by flow cytometry.

Generation of a Yeast-Display Recombinant Antibodies (scFv) Library Derived From B Cells of Ovarian Cancer Patient Ascites B cells used for VL/VH amplification were isolated from ascites of five ovarian cancer patients (stages III or IV) after Ficoll gradient and purification using CD19 magnetic beads (Miltenyi). Total RNA was extracted (1.25 mg) and twenty-two μg of mRNA (1.7%) were isolated (mRNA purification kit, Qiagen), consistent with the fact that mRNA normally accounts for 1-5% of total RNA. Fifty reverse transcription reactions were performed to permit the PCR amplification of the VH and VL gene fragments. A set of primers was designed to amplify human subfamilies of VH and VL gene fragments based on the MIGT data base (Sblattero and Bradbury, 1998, Immunotechnology 3(4):271-8). Annealing sequences were added to primers amplifying VH and VL fragments to enable gap repair with pAGA2 vector and the generation of a long-linker between VL and VH (GGSSRSSSSGGGGSGGGG; SEQ ID NO: 13) (Andris-Widhopf et al., 2011, Cold Spring Harb Protoc, 2011(9)). The long-linker DNA sequence was modified to encode yeast-optimized codons (5'-ggtggttcctctagatcttcctcctctggtggcggtgg ctcgggcggtggtggg-3'; SEQ ID NO: 14).

Figure 6A:
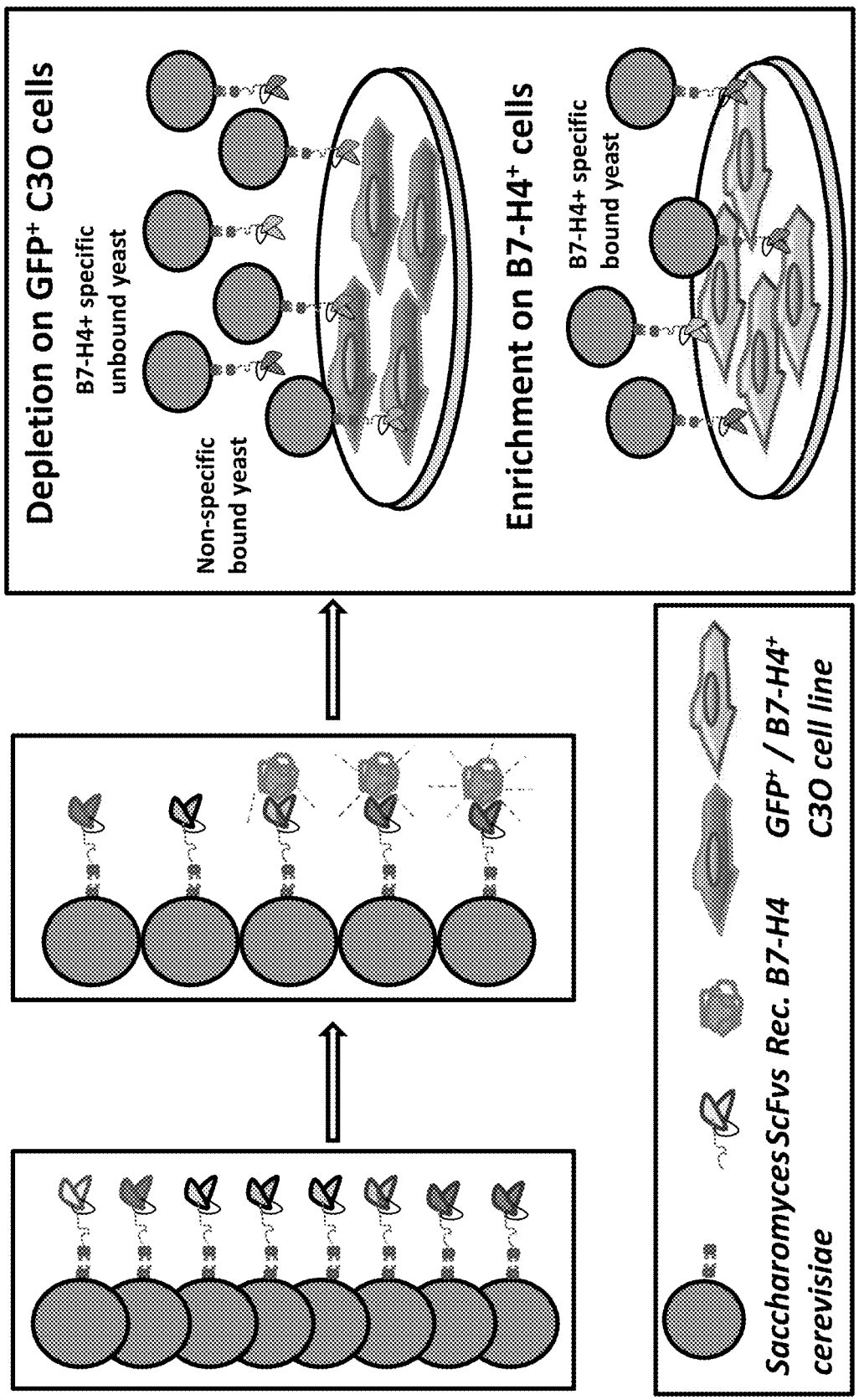
FIGS. 6A-6C are a series of images demonstrating the isolation of anti-B7-H4 scFvs from a new yeast display library of ovarian cancer patients and validation.

The following annealing sequences were added to the primers: 5'-ggtggtggaggttctggtggtggtggatctgtc-3'; SEQ ID NO: 15 to forward VL primers (annealing with 5' end of linearized Nhe I-Xho I pAGA2 vector); 5'-cgctgccaccgccgccgctggaacttgacctagaggatccgcc-3'; SEQ ID NO: 16 to reverse VL primers (annealing with long-linker); 5'-ctaggtcaagttccagcggcggcggtggcagcggaggcg gcggt-3'; SEQ ID NO: 17 to forward VH primers (annealing with long-linker); and 3'-gtcttcttcagaaataagcttttgttcggatccctcgaa-5'; SEQ ID NO: 18 to reverse VH primers (annealing with 3' end of linearized Nhe I-Xho I pAGA2 vector). PCR amplification were performed using a hot start of 5 min at 94° C., followed by 25 cycles of denaturation at 94° C. for 1 min, annealing at 55° C. for 1 min and extension at 72° C. for 1 min, with a final step of extension of 7 min at 72° C. The pAGA2 yeast display vector was linearized by Nhe I and Xho I. Linearized vector and PCR products were separated by electrophoresis, purified using a gel extraction kit (Invitrogen, Carlsbad, Calif.), and transfected into EBY100 yeast cells at a 1/3/3 ratio (FIG. 6A). Gap repair efficiency was evaluated by sequencing of fifty clones, as previously described (Zhao et al., 2011, J Immunol Methods 363(2):221-32).

Cloning of Recombinant B7-H4, Protein Expression and Purification

Figures 11A, 11B, 11C:
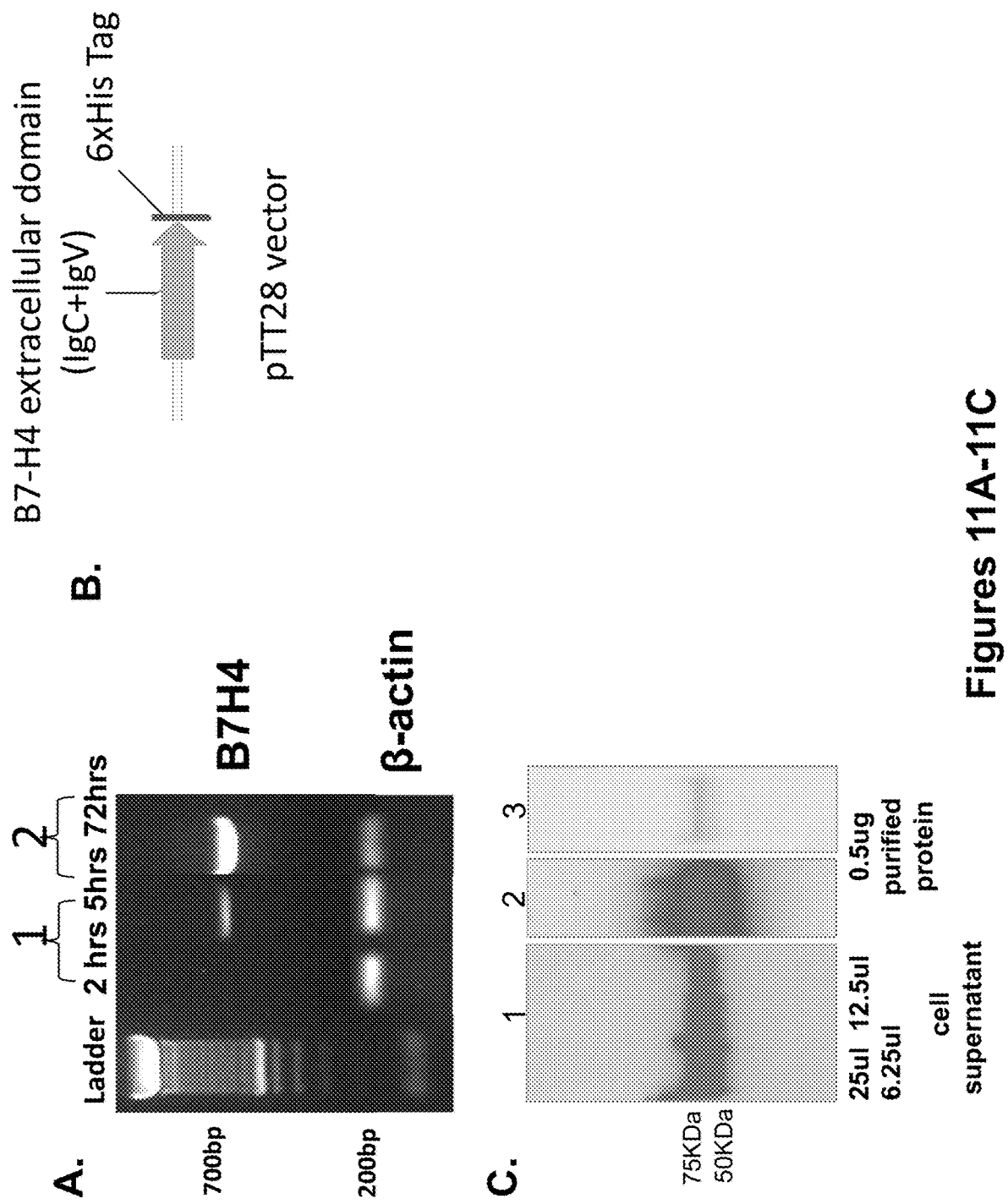
FIGS. 11A-11C depict cloning, expression, and purification of recombinant B7-H4.
Figures 12A, 12B:
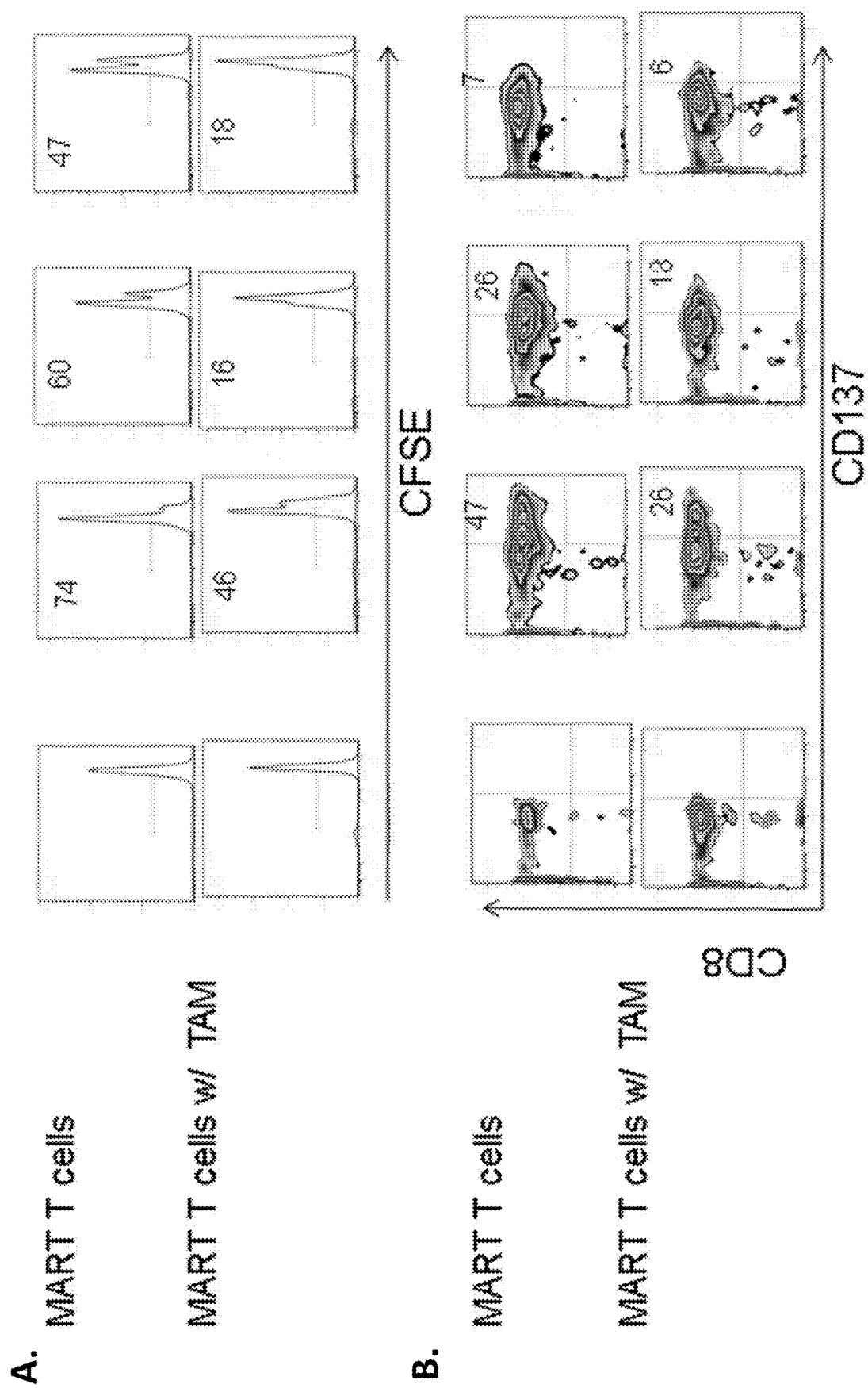
FIGS. 12A-12B are a series of images demonstrating that B7-H4$^+$ TAMs downregulate antigen-specific T cells proliferation and co-stimulation. MART-1 TCR specific T cells were stimulated with wild type T2 APCs pulsed with serial dilutions (0.0025-1 uM) of MART-1 or constant concentration (1 uM) of HER-2 irrelevant peptide to control for specific MART-1 TCR T cell stimulation. Proliferation was analyzed by CFSE dilution (FIG. 12A); co-stimulation was analyzed by detection of CD137 expression (FIG. 12B).

The extracellular domain of B7-H4 (IgC+IgV) was amplified from cDNA of human macrophages after in vitro tumor-polarization (Dangaj et al., 2011, PLoS One 6(12):e28386), using B7-H4 forward primer 5'-ggttctggtggtggaggttc tggtggtggtggatctgagtttggtatttcagggagacactccatca-3'; SEQ ID NO: 19 and B7-H4 reverse primer 5'-agaccgag-gagagggttagggataggcttaccgtcgacagaagcctttgagtttagca gctgtag-3'; SEQ ID NO: 20. B7-H4 cDNA was verified by sequencing and cloned into a mammalian expression vector (pTT28, kind gift from Yves Durocher, National Research Council of Canada) (FIG. 2B) for mammalian expression fused to 6×HIS Tag in 293-F mammalian cells. Recombinant B7-H4 (rB7-H4) was purified with Nickel sepharose beads (Sigma) and detectable by Western Blot as a 75 KDa fragment with an anti-B7-H4 polyclonal antibody (FIG. 11C).

Construction of pELNS-B7-H4 Lentivirus

For the production of cDNA encoding full B7-H4, RNA was isolated from OVCAR-3 ovarian tumor cells and reverse transcript with the kit "ready-to-go you-prime First-Strand Beads" (GE Healthcare, Piscataway, N.Y., USA). Resulting cDNA was used as template for PCR amplification of B7-H4 cDNA fragment of 795-bp with the primers B7-H4-F 5'-ACGCTCTAGAATGGCTTCCCTGGGGCA-GATC CTCT-3'; SEQ ID NO: 21 and B7-H4-R: 5'-ACGCGTCGACTTATTTTAGCATCA GGTAAGGGCTG-3'; SEQ ID NO: 22. The resulting PCR products contained an XbaI site (B7-H4-F) and a SalI site (B7-H4-R) was and were digested for cloning into a third generation self-inactivating lentiviral expression vector (pELNS, (Lanitis et al., 2012, Mol Ther 20(3):633-43)) in which the transgene expression is driven by the EF-1a promoter, to obtain pELNS-B7-H4.

Recombinant Lentivirus Production

High-titer replication-defective lentiviral vectors were produced and concentrated as previously described (Lanitis et al., 2012, Mol Ther 20(3):633-43). 293T human embryonic kidney cells were seeded at $10 \times 10^6$ per T-150 tissue culture flask 24 h before transfection. All plasmid DNA were purified using the QIAGEN Endo-free Maxi prep kit. Cells were transfected with 7 Lg pVSV-G (VSV glycoprotein expression plasmid), 18 µg of pRSV.REV (Rev expression plasmid), 18 µg of pMDLg/p.RRE (Gag/Pol expression plasmid), and 15 µg of pELNS transfer plasmid using Express Inn (Open Biosytems). Viral supernatant was harvested at 24 and 48 h post-transfection. Viral particles were concentrated by ultracentrifugation for 3 h at 25,000 rpm with a Beckman SW28 rotor (Beckman Coulter, Fullerton, Calif.) and resuspended in 4 ml of RPMI full medium.

Lentiviral Transduction of Cancer Cell Lines and T2 Cells with pELNS-B7-H4

For the transduction of the cancer cell lines C30, MDA 231 and 624 with pELNS-B7-H4 lentiviral particles $1.5 \times 10^5$ tumor cells were seeded in a six-well plate one day prior their transduction. Next day, the medium was replaced with 1 ml of lentivirus when the cells reached a confluence of about 30%. Medium was replaced twenty four hours after transduction with fresh RPMI medium (C30 and 624) or DMEM medium (MDA231). For the transduction of T2 cells, 1 ml of lentivirus was applied to $3 \times 10^5$ cells in a 24 well plate. The expression of B7-H4 was assessed at day 5 post transduction.

Production of Retroviral Particles by Transient Transfection of 293 GP Cells

The HER-2 TCR and the MART-1 TCR (DF5a) (Johnson et al., 2006, J Immunol 177(9):6548-59) used in this study were in the pMSGV1 vector backbone which is a derivative of the vector pMSGV (murine stem cell virus (MSCV)-based splice-gag vector) and utilizes a MSCV long terminal repeat (LTR) (Zhao et al., 2005, J Immunol 174(7):4415-23). To produce retroviral supernatants, $1 \times 10^6$ of 293-GP cells (transient viral producer cells) in a 6-well plate were co-transfected with 1.5 µg of retroviral vector DNA from each of the constructs and 0.5 µg of envelope DNA (RD 114) using the Lipofectamine 2000 reagent (Invitrogen) and Optimem medium (BD Biosciences). Media was changed to DMEM with 10% FBS after 18 h, and viral supernatants were harvested at the 48-h time point. These supernatants were then used to transduce T cells for expression of a TCR that targets either HER-2- or MART-1-derived peptide.

Isolation of Anti-B7-H4 scFvs from Yeast Display scFv Library

Anti-B7-H4 scFvs were first selected by magnetic and flow sorting using rB7-H4 vs. control protein, as previously described (Dangaj et al., 2011, PLoS One 6(12):e28386; Zhao et al., 2011, J Immunol Methods 363(2):221-32). In addition, the selected subpopulation of yeast-display scFvs were further selected by panning using a protocol derived from Wang et al. (Wang et al., 2007, Nat Methods 4(2):143-5) with the following specifications: C30 ovarian cancer cell line was transduced with pELNS-B7-H4 or with pELNS-GFP as negative control, and grown in monolayer to 90% confluence on poly-L-Lysine-coated dishes. Yeast were induced to express scFv, washed with PBE and depleted for non-specific binding by 2 incubations with GFP$^+$C30 cells at a ratio of 30-60:1 (yeast:cells) for 30 min at RT with gentle rotation to prevent clumping (1-2 speed). Unbound yeast were then harvested and incubated with plastic-immobilized B7-H4+C30 cells for 30 min at RT with gentle rotation. Plates were washed twice with PBS for 5 min at RT with gentle rotation and examined under microscope. Yeast clusters that were still binding to cells were harvested and grown on the cell plate O/N and transferred to new flask for further amplification. Yeast panning was repeated 4 times. Yeast displayed scFvs were converted into soluble forms as described previously (Dangaj et al., 2011, PLoS One 6(12): e28386; Zhao et al., 2011, J Immunol Methods 363(2):221-32).

Human T Cell Transduction

Primary human T cells were purchased from the Human Immunology Core at University of Pennsylvania and were isolated from healthy volunteer donors following leukapheresis by negative selection. All specimens were collected under a University Institutional Review Board-approved protocol, and written informed consent was obtained from each donor. T cells were plated at a concentration of $1 \times 10^6$/ml in 24-well plates (Costar) in complete media (RPMI 1640 supplemented with 10% heat inactivated fetal bovine serum (FBS), 100 U/ml penicillin, 100 µg/ml streptomycin sulfate, 10 mM HEPES), and stimulated with anti-CD3 and anti-CD28 mAbs coated beads as described by manufacturer (Invitrogen) (Levine et al., 1997, J Immunol, 159(12):5921-30) for 18-24 h prior to transduction. Non-tissue culture-treated 12-well plates (Becton Dickinson Labware, Franklin Lakes, N.J.) were treated with 25 ug/ml of recombinant retronectin fragment at 4° C. as directed by the manufacturer (RetroNectin, Takara, Otsu, Japan). After an overnight incubation, the retronectin was removed and the plate was blocked with 2% BSA in PBS at RT for 30 minutes. The retroviral vector supernatant (2-3 ml) was then applied by centrifugation (2000×g for 2 hours), and after discarding the supernatant $5 \times 10^5$ of stimulated T cells were added to each well in a final volume of 1 ml RMPI growth medium per well. Plates were centrifuged for 10 min at 1000×g and incubated overnight. The transduction process was repeated the following day. After transduction, the cells were grown in the RMPI with 10% FBS and human recombinant interleukin-2 (Novartis) was added every other day to a 100 IU/ml final concentration. Cell density of $0.5-1 \times 10^6$ cells/ml was maintained. Expression of the exogenous HER-2 and MART-1 TCR was validated 5 days after transduction using APC-conjugated MHC-peptide tetramers (Becton Dickinson, San Jose, Calif.) with specificities for HLA-A2-HER2369 and HLA-A2-MART-1.

T Cell Activation

B7-H4 inhibition of T cell activation and proliferation was performed using plate-immobilized recombinant B7-H4. A day prior to T cell activation, antibodies (anti-CD3 mAb (clone OKT3) and/or anti-CD28 (eBiosciences) were plastic-immobilized at 5 µg/ml and 2 µg/ml respectively, in 100 µl/well of bicarbonate buffer on flat 96-well tissue culture plates, overnight. The antibody solution was removed the day of T cell activation, and 10 µg/ml of rB7-H4 protein was coated in 100 µl/well of bicarbonate buffer for 2 hrs at 37° C. A non relevant recombinant protein (folate receptor alpha) was used as control protein. In the meantime, T cells were labelled with 3 µM of CFSE, as instructed by manufacturer (Invitrogen). Plates were then washed two times with PBS and labelled T cells were cultured at $1 \times 10^5$ in 150 µl/well in the presence of anti-B7-H4 scFvs added at day 0 at a concentration of 2.5 µg/ml. T cell responses were analyzed five days after activation. Assays were performed in triplicates.

T Cell Co-Culture with T2 APCs

Wild type, GFP- or B7-H4-transduced T2 APCs were resuspended at 10×10$^6$/ml and loaded with HER-2 or MART-1 peptides at various peptide concentrations at 37° C. for 2 hrs. Co-culture of peptide-loaded APCs with HER-2 or MART-1 TCR specific T cells was performed at ratio of 1:1 (1×10$^5$ T2/1×10$^5$ T cells) in 200 µl of RPMI media in round bottom 96-well tissue culture plates. Anti-B7-H4 scFvs were added at day 0 at 5 µg/ml of concentration. T cell responses were analyzed two days after co-culture. Assays were performed in triplicates.

TAM-mediated TCR T cell inhibition assay were performed in 24 well transwell co-cultures at ratio of 1:1:1 (1×10$^5$ T2/1×10$^5$ T cells/1×10$^5$ TAM). TAMs were differentiated and polarized as described previously (Dangaj et al., 2011, PLoS One 6(12):e28386). Briefly M1 polarized macrophages were in transwell co-cultured with OVCAR3 ovarian cancer line for 3 days. At day 3 of tumor polarization of macrophages, TCR T cells and peptide pulsed wild type T2 cells were added in the transwells containing or not macrophages. Anti-B7-H4 scFvs were added at day 0 at 5 ug/ml concentration. T cell responses were analyzed three days after co-culture. Assays were performed in triplicates.

T Cell Co-Culture with Tumor Cells

Wild type or B7-H4$^+$624 melanoma cell line and/or wild type or B7-H4$^+$ MDA231, were co-cultured with HER-2 or MART-1 TCR specific T cells at a ratio of 1:1 (1×10$^5$ T2/1×10$^5$ T cells) in 200 µl of RPMI media. 5 g/ml of anti-B7-H4 scFvs were added at day 0 and T cell responses were analyzed two days after co-culture. Assays were performed in triplicates.

Flow Cytometry

Flow cytometry was performed as described (Dangaj et al., 2011, PLoS One 6(12):e28386). Before labelling cells were incubated with mIgG to block non-specific binding of Fcγ Receptors. 7-AAD was used to exclude dead cells.

ELISA

IFN-γ ELISA was performed as indicated by manufacturer (Biolegend).

Western Blotting

Western blotting was performed as described (Dangaj et al., 2011, PLoS One 6(12):e28386).

Statistics

P values were calculated using One Way Anova and Unpaired T test analysis.

The results of the experiments are now described.

Figure 5A:
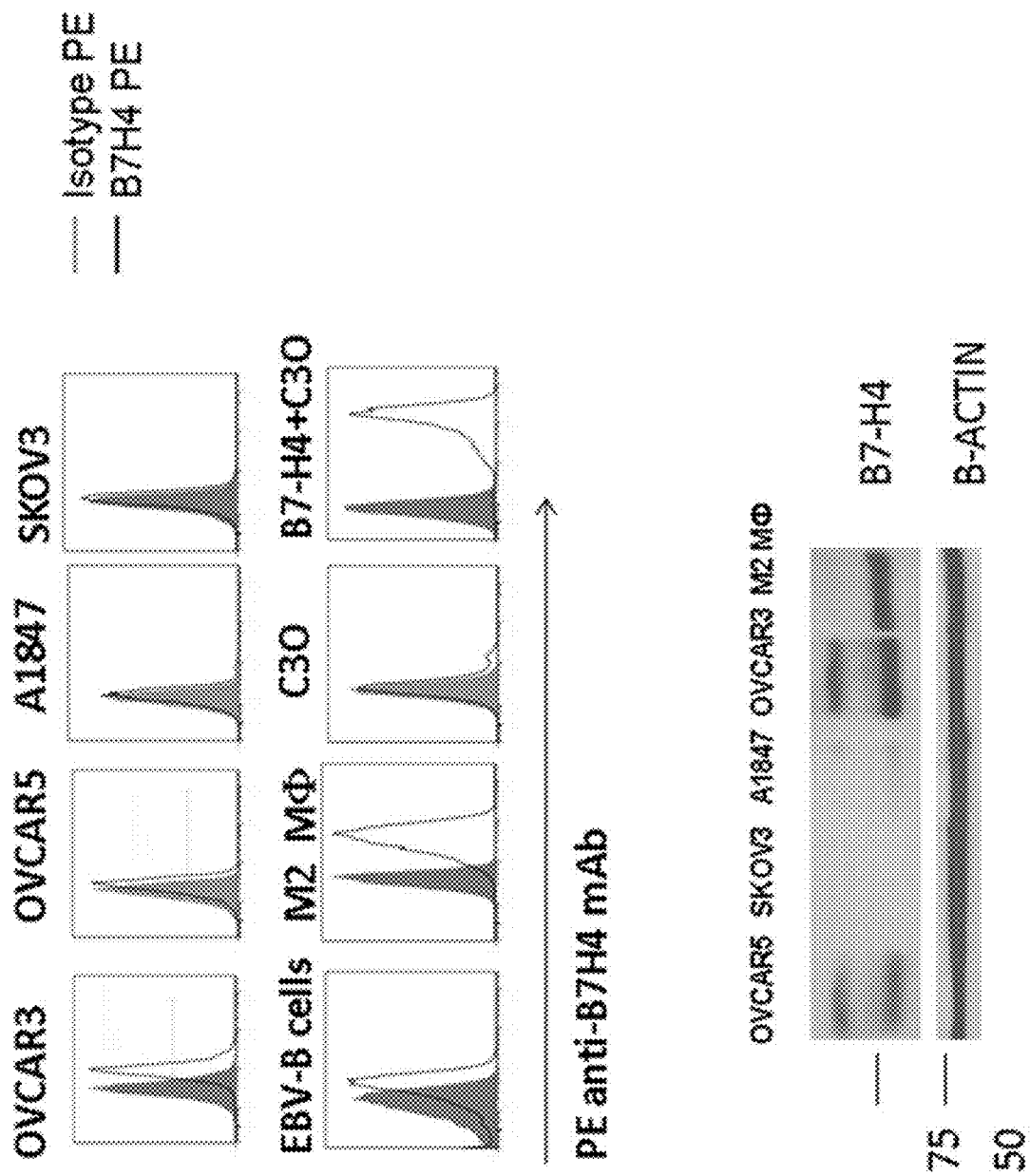
FIGS. 5A-5D are a series of images that demonstrate B7-H4 expression in human ovarian cancer cells.
Figure 5B:
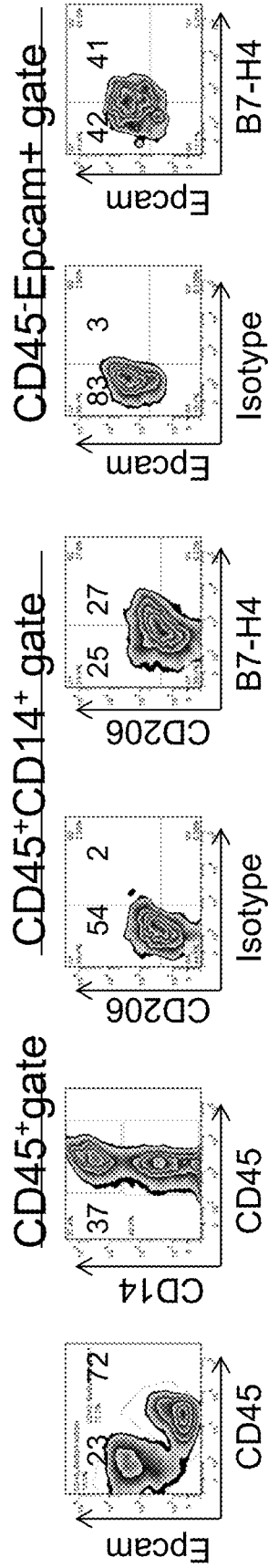
Figure 5B:
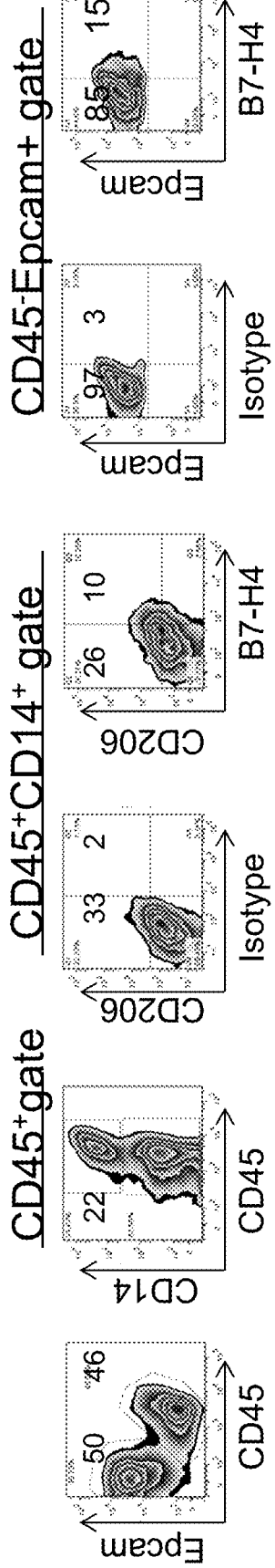
Figure 5C:
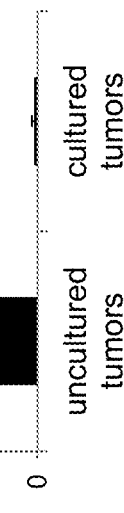
Figure 5D:
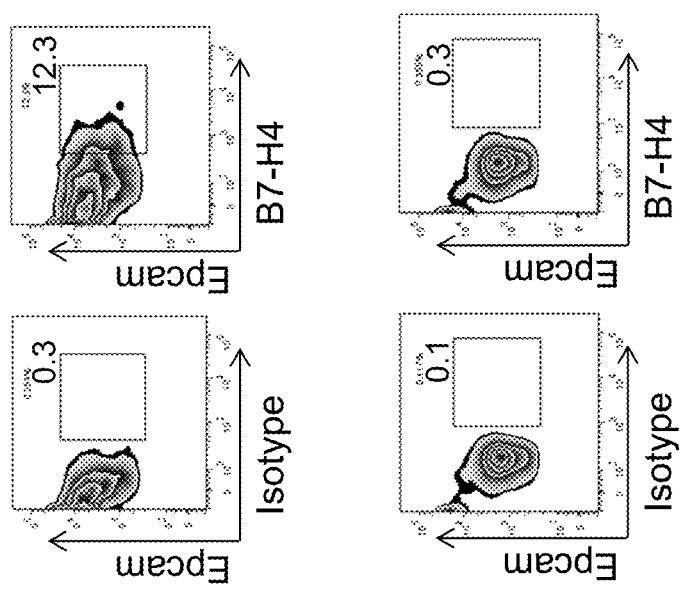

B7-H4 Expression at the Cell Surface of Tumor-Infiltrating Monocytes and Tumor Cells is Up-Regulated In Vivo and Down Regulated by In Vitro Culture Cell surface-targeting requires the presence of membrane-bound molecules. B7-H4 cell surface expression in established ovarian cancer cell lines (n=5) and in ovarian cancer samples (ascites and solid tumors) (n=16) analyzed using flow cytometry. It was observed that cell surface expression of B7-H4 was limited in established ovarian cancer cell lines (1 out of 5, OVCAR3, FIG. 5A), consistently with previous report (Choi et al., 2003, J Immunol 171(9):4650-4). As positive controls of B7-H4 cell surface expression, EBV B cells were used (Quandt et al., 2011, Clin Cancer Res 17(10):3100-11), in vitro differentiated macrophages stimulated with IL4 and IL-10, and B7-H4 transduced C30 cells (FIG. 5A, as indicated). In contrast, a broad cell surface expression of B7-H4 among 16 solid tumors and ascites from ovarian cancer patient samples was observed (FIG. 5B; Tables 1 and 2). Mean B7-H4 expression in CD45-Epcam$^+$ tumor cells was of 28%±17.84 in ascites (Table 1) and 9.44%±8.31 in solid tumors (Table 2). Twenty five percent of patients had more than 30% of CD45$^-$ Epcam$^+$ tumor cells expressing B7-H4, and more than half of the patients expressed B7-H4 on 4 to 15% of their tumor cells. B7-H4 expression was also observed in CD45$^-$Epcam$^-$ cells derived from solid tumors (Table 2). In addition, B7-H4 cell surface expression on tumor-associated CD45$^+$CD14$^+$ monocytes was confirmed, as reported by Cryczek et al. (Kryczek et al., 2006, J Exp Med 203(4):871-81), and 3 to 40% of CD45$^+$CD14$^+$ cells expressed both B7-H4 and CD206/mannose receptor, a marker of mature M2 macrophages and of TAMs (Table 2). To address whether B7-H4 expression in tumor cells is an in vivo inducible effect, a human ovarian cancer cell line with undetectable surface B7-H4 expression, OVCAR5 (FIG. 5A), was used to establish intraperitoneal tumors in Balb C/nude mice. Nine weeks after tumor injection, 6 ascites and solid tumors were collected and analyzed for B7-H4 expression by flow cytometry. B7-H4 cell surface expression in Epcam$^+$ tumor cells was upregulated in all freshly harvested OVCAR5 tumors (n=6), ranging from 4 to 38% (mean=12.8±5.18) (FIGS. 5C and 5D). However, after a short term culture of OVCAR5 cells from ascites or solid tumor, B7-H4 cell surface expression was back to undetectable levels (FIGS. 5C and 5D). These results demonstrated that B7-H4 cell surface expression in ovarian tumor cells is induced in vivo and down-regulated by short term culture.

TABLE 1

B7H4 expression on tumor-infiltrating monocytes and tumor cells in human ovarian cancer ascites

| Specimen ID | % CD45$^+$ | % CD45$^+$ CD14$^+$ | % CD45$^+$ CD14$^+$ B7H4$^+$ | % CD45$^+$ CD14$^+$ CD206$^+$ | % CD45$^+$ CD14$^+$ CD206$^+$ B7H4$^+$ | % CD45$^-$ Epcam$^+$ | % CD45$^-$ Epcam$^+$ B7H4$^+$ |
|---|---|---|---|---|---|---|---|
| 1647 | 97.90 | 40.00 | 40.5 | 49.00 | 58.16 | 1.00 | 32.00 |
| 1686 | 98.90 | 20.30 | 0.70 | 58.00 | 1.72 | 0.15 | 13.00 |
| 1714 | 96.50 | 3.49 | 1.80 | 42.00 | 2.86 | 2.10 | 13.36 |
| 1753 | 95.70 | 72.80 | 17.80 | 55.00 | 32.73 | 2.43 | 14.74 |
| 1773 | 71.70 | 37.40 | 25.00 | 75.00 | 22.67 | 23.30 | 38.90 |
| 1756 | 49.00 | 49.00 | 17.00 | 52.00 | 48.08 | 42.90 | 57.00 |
| Mean | 84.95 | 37.16 | 17.13 | 55.17 | 27.7 | 11.98 | 28.17 |
| St. Dev | 20.39 | 23.81 | 14.92 | 11.16 | 23.18 | 17.51 | 17.84 |

Surface B7-H4 expression was assessed in human ovarian cancer ascites using flow cytometry (n = 6); results were expressed in percentage of stained cells and plotted as indicated.

TABLE 2

B7H4 expression on tumor-infiltrating monocytes and tumor cells in human ovarian solid tumors

| ID | % CD45+ | % CD45+ CD14+ | % CD45+ CD14+ B7H4+ | % CD45+ CD14+ CD206+ | % CD45+ CD14+ CD206+ B7H4+ | % CD45− Epcam+ | % CD45− Epcam+ B7H4+ | % CD45− Epcam− | % CD45− Epcam− B7H4+ |
|---|---|---|---|---|---|---|---|---|---|
| 1789 | 10.50 | 39.40 | 29.75 | 58.00 | 39.65 | 9.20 | 7.00 | 76.00 | 0.00 |
| 1790 | 24.70 | 26.00 | 22.8 | 36.00 | 27.78 | 6.86 | 11.00 | 66.50 | 0.00 |
| 1746 | 45.58 | 21.62 | 15.00 | 35.00 | 29.29 | 49.78 | 13.00 | 0.00 | — |
| 1751 | 62.50 | 21.40 | 8.40 | 42.00 | 20.24 | 12.30 | 29.80 | 22.30 | 11.75 |
| 1761 | 66.10 | 23.20 | 7.75 | 42.00 | 14.52 | 11.50 | 9.60 | 20.30 | 10.62 |
| 1767 | 86.00 | 5.26 | 1.70 | 70.00 | 2.86 | 0.00 | 0.00 | 11.80 | 3.99 |
| 1791 | 4.66 | 40.80 | 13.00 | 70.00 | 14.29 | 37.20 | 5.00 | 54.60 | 5.20 |
| 1761 | 51.80 | 61.20 | 7.69 | 45.00 | 13.33 | 4.18 | 12.00 | 42.50 | 4.00 |
| 1791 | 44.00 | 43.00 | 10.00 | 25.00 | 4.73 | 35.00 | 4.00 | 16.30 | 31.00 |
| 1801 | 40.00 | 25.00 | 44.00 | 32.00 | 17.20 | 27.00 | 3.00 | 27.00 | 13.00 |
| Mean | 43.58 | 30.69 | 16.10 | 45.50 | 18.39 | 19.30 | 9.44 | 33.73 | 8.84 |
| St. Dev | 25.20 | 15.59 | 12.757 | 15.59 | 11.30 | 16.74 | 8.31 | 25.06 | 9.60 |

Surface B7-H4 expression was assessed in human solid ovarian tumors using flow cytometry (n = 10); results were expressed in percentage of stained cells and plotted as indicated.

Generation of a Yeast Display Library Derived from Tumor-Associated B Cells from Ovarian Cancer Patients A novel yeast-display library of recombinant antibodies (scFvs) derived from the variable regions of the heavy and light chains of B cells isolated from human ovarian cancer ascites (n=10) and PBMCs (n=1) was constructed. The insertion of $V_H$-$V_L$ fragments encoding the scFv in pAGA2 vector (Zhao et al., 2011, J Immunol Methods 363(2):221-32) was performed using homologous recombination in yeast combining $V_H$ PCR fragments, $V_L$ PCR fragments and linearized pAGA2 vector. $V_H$ and $V_L$ were linked together by the linker (GGSSRSSSSGGGGSGGGG; SEQ ID NO: 13 (Zhang et al., 2012, Mol Ther 20(7):1298-304; Andris-Widhopf et al., 2011, Cold Spring Harb Protoc, 2011(9)). The diversity of the library was estimated at $10^9$.

Isolation and Validation by Capture ELISA of Novel Anti-B7-H4 scFvs

Figures 6B, 6C:
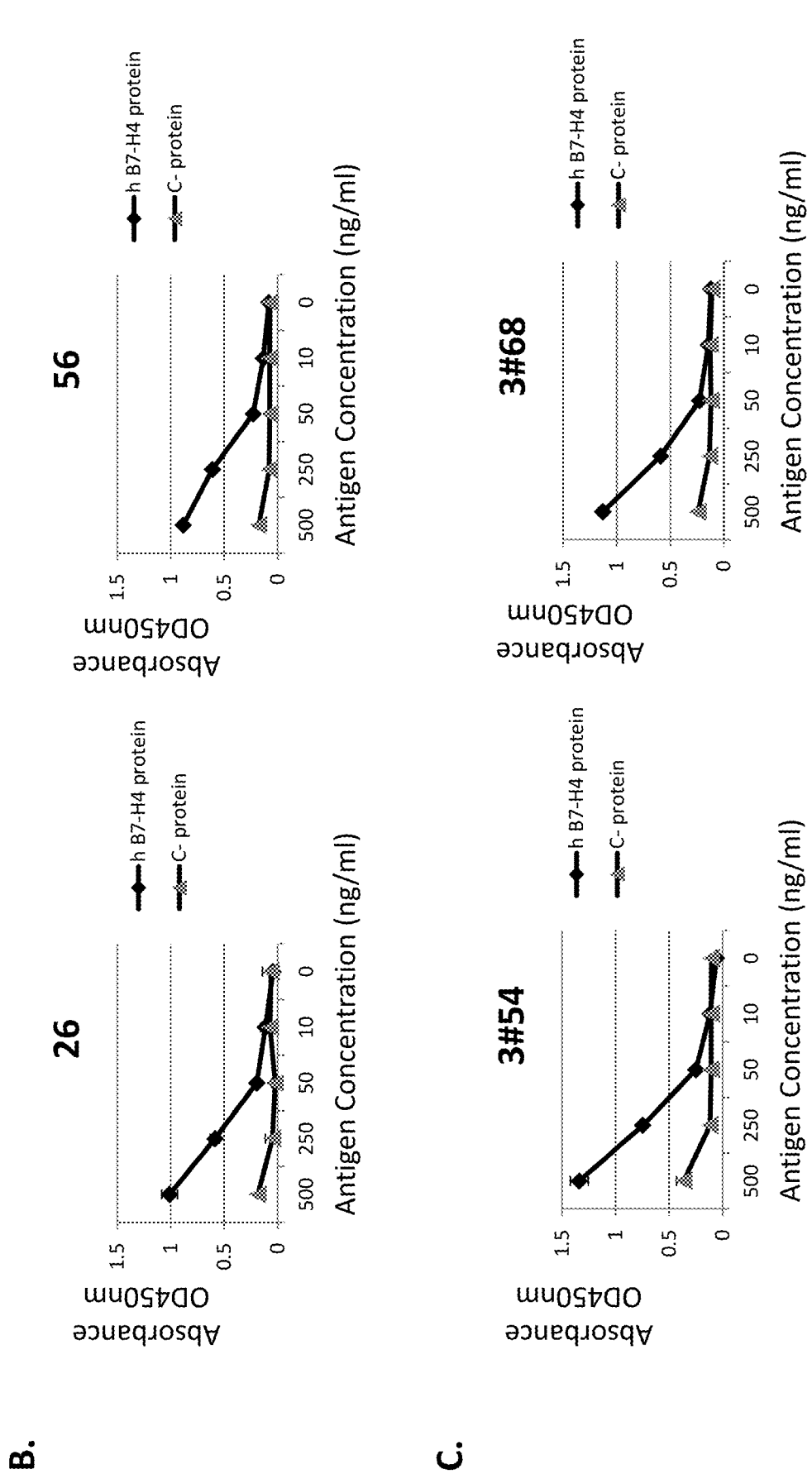

The method of soluble scFv isolation is described elsewhere herein and recapitulated in FIG. 6A. Briefly 3 magnetic and 2 flow sortings of the yeast-display scFv library was performed from which a subpopulation of yeast display scFvs that bound to soluble recombinant B7-H4 (rB7-H4) was isolated. The selected subpopulation of yeast-display scFvs was then directly transformed in soluble scFvs by homologous recombination in p416-BCCP vector, as previously described (Zhao et al., 2011, J Immunol Methods 363(2):221-32; Scholler et al., 2006, J Immunol Methods 317(1-2): 132-43; Bergan et al., 2007, Cancer Lett 255(2): 263-74) as referred to as "protein-based screening strategy." Alternatively, screening was completed by further enrichment with four rounds of panning on C30 cell line transduced to express B7-H4 at the cell surface, or GFP as negative control. This screening method is referred to as "cell-based screening strategy." After transformation into soluble forms, isolated scFvs were high-throughput purified from yeast supernatants (Zhao et al., 2011, J Immunol Methods 363(2):221-32; Bergan et al., 2007, Cancer Lett 255(2):263-74), and screened by capture ELISA for specific binding to 500 ng/ml of rB7-H4 (data not shown). Two scFvs (#26 and #56) issued from the protein-based screening strategy, and 2 scFvs (3#54 and 3#68) issued from the cell-based screening strategy were selected for further analysis. Selected scFv were assayed by capture ELISA for binding to serial dilutions of rB7-H4 with similar results; BSA was used as control protein (FIGS. 6B-6C). ScFvs were sequenced and analyzed for their germline immunoglobulin gene usage of the predicted amino-acid sequence by the Kabat system (Table 3). Immunoglobulin gene usage comparison of protein-based isolated scFv clones #26 and #56 demonstrated substantial differences of immunoglobulin gene usage in both heavy and light chains. ScFv clones 3#54 and 3#68 displayed different immunoglobulin gene usage for heavy chains, but essentially same light chains. Clone #26 and 3#68 shared the same IGHV and IGHD gene usage but different IGHJ genes for the heavy chains and different usage for the light chains. Sequence identifiers for the scFvs are depicted in Table 4:

TABLE 3

Germline immunoglobulin gene usages of the predicted amino-acid sequence of the anti-B7-H4 scFvs

| B7-H4 scFv Ig Gene Usage | HEAVY CHAIN | | | LIGHT CHAIN | |
|---|---|---|---|---|---|
| | VH GENE | D GENE | JH GENE | VL GENE | JK, L GENE |
| 26 scFv | IGHV1-2*02 (92.1%) | IGHD5-24*01 (91.7%) | IGHJ6*02 (94.1%) | IGKV3-20*01 (94.8%) | IGKJ2*02 (97.0%) |
| 56 scFv | IGHV4-39*07 (98.7%) | IGHD6-13*01 (100%) | IGHJ3*02 (100%) | IGLV6-57*01 (93.8%) | IGLJ3*02 (91.4%) |
| 3#54 scFv | IGHV4-b*02 (93.2%) | IGHD6-19*01 IGHD6-13*01 (100%) | IGHJ6*02 (100%) | IGLV1-47*01 (97.9%) | IGLJ3*02 (97.3%) |
| 3#68 scFv | IGHV1-2*02 (92.1%) | IGHD5-24*01 (91.7%) | IGHJ3*01 (100%) | IGLV1-47*01 (98.3%) | IGLJ3*02 (94.6%) |

Kabat analysis of the homology of heavy (H) and light (L) chain variable regions to germline immunoglobulin genes is displayed for each anti-B7-H4 scFv clone.

TABLE 4

Sequence Identifiers for anti-B7-H4 antibodies

| SEQ ID NO: # | IDENTITY |
|---|---|
| SEQ ID NO: 1 | anti-B7H4 scFv clone 56 (amino acid) |
| SEQ ID NO: 2 | anti-B7H4 scFv clone 26 (amino acid) |
| SEQ ID NO: 3 | anti-B7H4 scFv clone 54 (amino acid) |
| SEQ ID NO: 4 | anti-B7H4 scFv clone 68 (amino acid) |
| SEQ ID NO: 5 | anti-B7H4 scFv clone 56 (nucleic acid) |
| SEQ ID NO: 6 | anti-B7H4 scFv clone 26 (nucleic acid) |
| SEQ ID NO: 7 | anti-B7H4 scFv clone 54 (nucleic acid) |
| SEQ ID NO: 8 | anti-B7H4 scFv clone 68 (nucleic acid) |

Figure 7A:
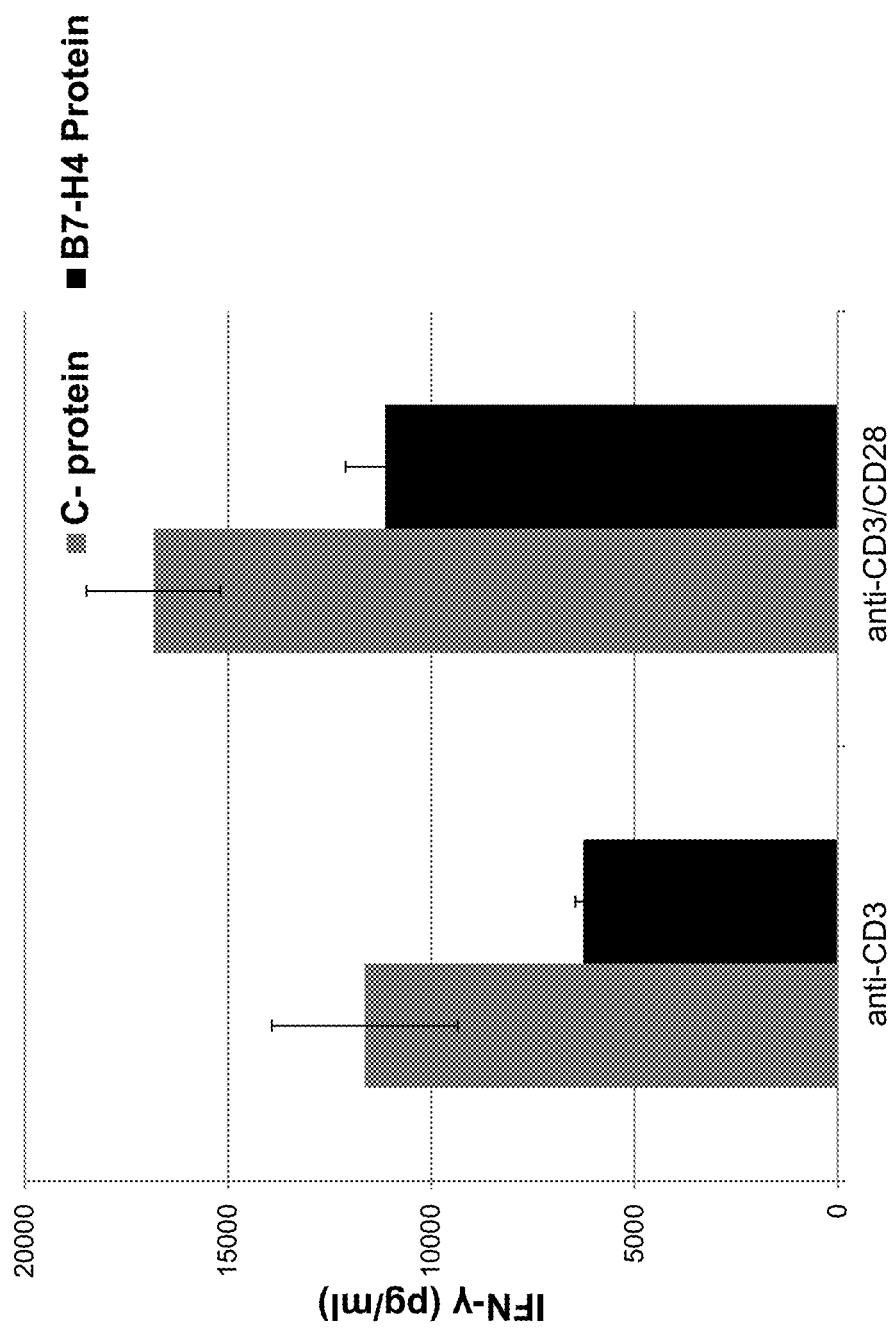
FIGS. 7A-7D are a series of images demonstrating that recombinant B7-H4 protein inhibits polyclonal T cell stimulation and anti-B7-H4 scFvs reverse T cell inhibition. T cells were stimulated with plate bound anti-CD3 and/or anti-CD28 in the presence of immobilized recombinant B7-H4 (black bars) or irrelevant control protein (FOLR1, grey bars).
Figure 7B:
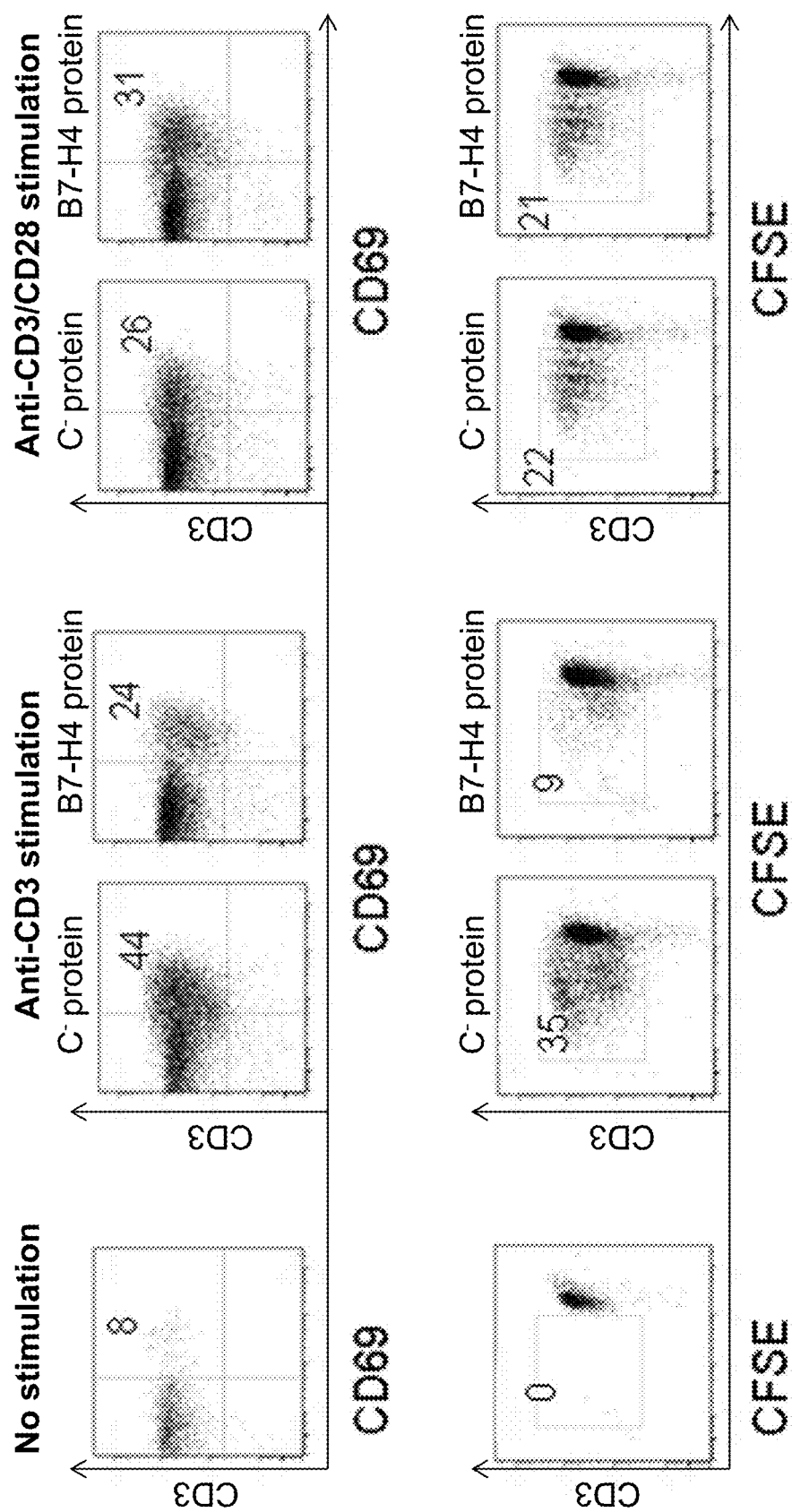
Figure 7C:
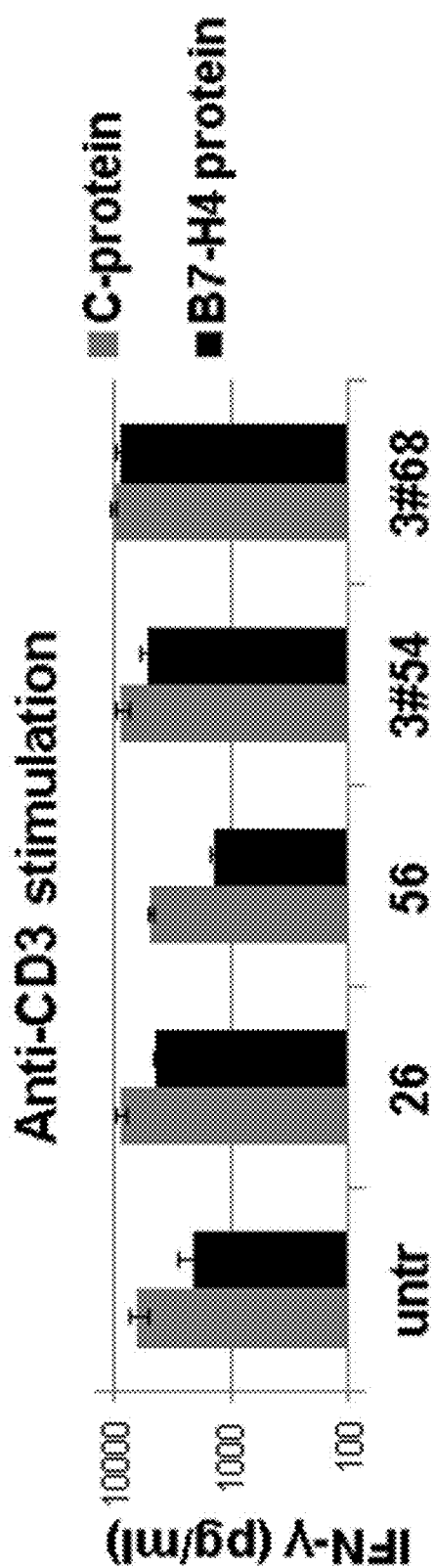
Figure 7D:
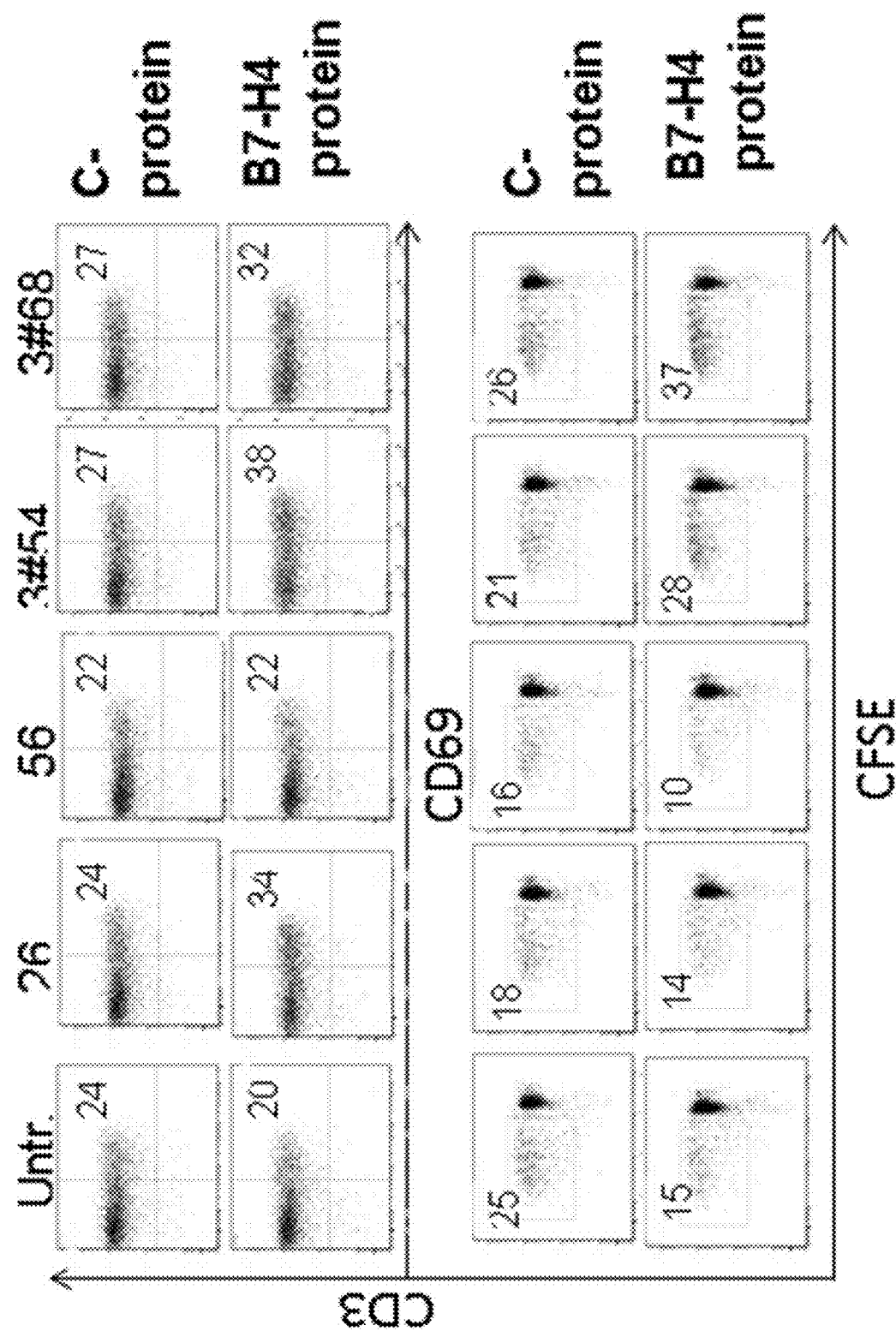

Recombinant B7-H4 (rB7-H4) Protein Inhibits T Cell Polyclonal Activation and Anti-B7-H4 scFvs Blocks rB7-H4-Dependant T Cell Inhibition Normal donor T cells were stimulated with anti-CD3 and/or anti-CD28 immobilized antibodies (Abs) in the presence of soluble rB7-H4 or of a control protein (soluble recombinant alpha-folate receptor). T cells stimulated by anti-CD3 and/or anti-CD28 Abs secreted IFN-γ, expressed the activation marker CD69 and proliferated as assessed by CFSE labeling (FIGS. 7A-7B). However, the presence of plate-bound rB7-H4 inhibited IFN-γ secretion (p=0.03 comparing rB7-H4 to control protein), CD69 expression and proliferation mediated by CD3 stimulation. While rB7-H4 inhibited T-cell activation in response to CD3-stimulation, T cell IFN-γ secretion and proliferation mediated by a combination of anti-CD3 and anti-CD28 mAbs were not significantly inhibited by the presence of rB7-H4 (p=0.09) (FIGS. 7A-7B). Thus, CD3-mediated T cell stimulation was chosen to functionally characterize the anti-B7-H4 scFvs in the rest of the study. FIGS. 7C-7D shows that several anti-B7-H4 scFvs could reverse rB7-H4 inhibition of T-cell polyclonal activation (FIGS. 7C and 7D). Anti-B7-H4 scFvs #26 significantly reduced the inhibition of IFN-γ T cell secretion (p=0.0128 when comparing to untreated condition) but did not fully overcome B7-H4-mediated inhibition of IFN-γ secretion nor reconstituted T cell proliferation (FIG. 7D). In contrast, anti-B7-H4 scFvs 3#54 and 3#68 restored T cell IFN-γ secretion (FIG. 7C) and reversed rB7-H4-dependent inhibition of T cell proliferation to normal levels (p=0.0406 for 3#54; p=0.1305 for 3#68) (FIG. 7D). Of note, the presence of anti-B7-H4 scFv 3#68 in CD3-activated T cells triggered higher IFN-γ secretion in the absence of any protein or in the presence of control protein (FIG. 7C) but did not modify T cell proliferation (FIG. 7D). These results support the hypothesis that scFv interfering with functional interactions between B7-H4 and B7-H4 putative T cell ligand can block B7-H4-dependent T cell inhibition.

Figures 8A, 8B, 8C, 8D, 8E:
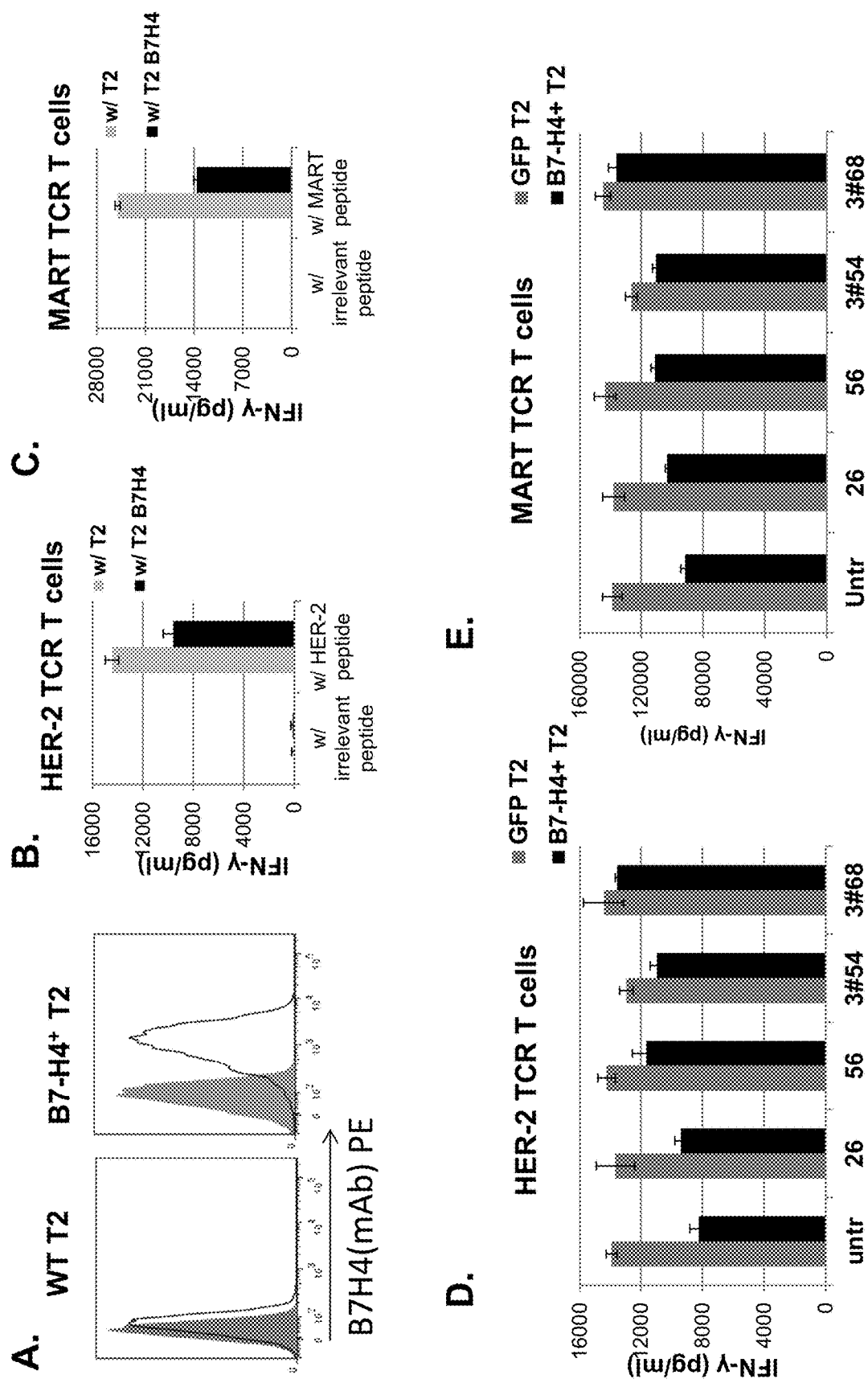
FIGS. 8A-8E are a series of images demonstrating that $B7-H4^+$ APCs inhibit antigen-specific T cells and anti-B7-H4 scFvs reverse T cell inhibition.

Antigen-Specific T Cell Activation is Inhibited by Peptide-Pulsed APCs Expressing B7-H4 and can be Restored by Anti-B7-H4 scFvs B7-H4 expression has been reported on tumor-infiltrated DCs (Cheng et al., 2011, J Immunoassay Immunochem 32(4):353-64). To model in vitro the role of B7-H4 in a system of antigen presentation that elicits tumor antigen-specific T cell responses, T2 antigen presenting cells (T2 APCs (Salter and Cresswell, 1986, EMBO J 5(5):943-9; Levine et al., 1997, J Immunol, 159(12):5921-30) were transduced with full-length B7-H4 (FIG. 8A), and peripheral human T cells were transduced with HER-2 specific TCR (Lanitis E. et al, manuscript in preparation) (FIG. 8B) or MART-1 specific TCR (Johnson et al., 2006, J Immunol 177(9):6548-59) (FIG. 8C). As negative control, T2 APC was transduced with GFP. T2 APCs were pulsed with MART-1 or HER-2 peptides and used to activated TCR transduced T cells. HER-2 and MART-1 TCR transduced T cells were activated with B7-H4 transduced (T2 B7-H4) or GFP transduced (T2), peptide-pulsed T2 APCs, and IFN-γ production was measured. MART-1 peptide was used as an irrelevant peptide for the stimulation of HER-2 TCR T cells and HER-2 peptide as an irrelevant peptide for the stimulation of MART-1 TCR T cells. FIGS. 8B and 8C show that B7-H4 expression on T2 APCs down-regulated antigen-specific T cell activation in both HER-2 and MART-1 specific T cells (p=0.0$^{362}$ for HER-2 TCR T cells and p=0.0024 for MART-1), demonstrating that B7-H4-dependent inhibition was not antigen-restricted. B7-H4-mediated inhibition of HER-2 and MART-1 specific T cells was partially reversed by anti-B7-H4 scFvs #56 and 3#54, but anti-B7-H4 scFv 3#68 could fully overcome B7-H4-mediated inhibition and restored MART-1 and HER-2 specific T cell responses (p=0.5748 and p=0.2892 respectively for B7-H4$^+$ T2 vs. T2) (FIGS. 8D and 8E). One Way Anova analysis of the differentially treated GFP$^+$ T2 conditions resulted in no significant statistical difference (p=0.7893 for HER-2 and p=0.2931 for MART-1 TCR T cells) whereas the same analysis for T2 B7-H4 resulted in statistical significant differences among the different conditions (p=0.00$^{66}$ for HER-2 and p<0.0001 for MART-1 TCR T cells). These results confirmed that blocking functional interactions between B7-H4-expressing APCs and T cells using anti-B7-H4 scFv 3#68 could overcome B7-H4-dependent T cell inhibition. In addition, functional variations observed between the different anti-B7-H4 scFvs suggested that the mechanism underlying B7-H4-mediated T cell inhibition depends on a specific epitope.

Figure 9A:
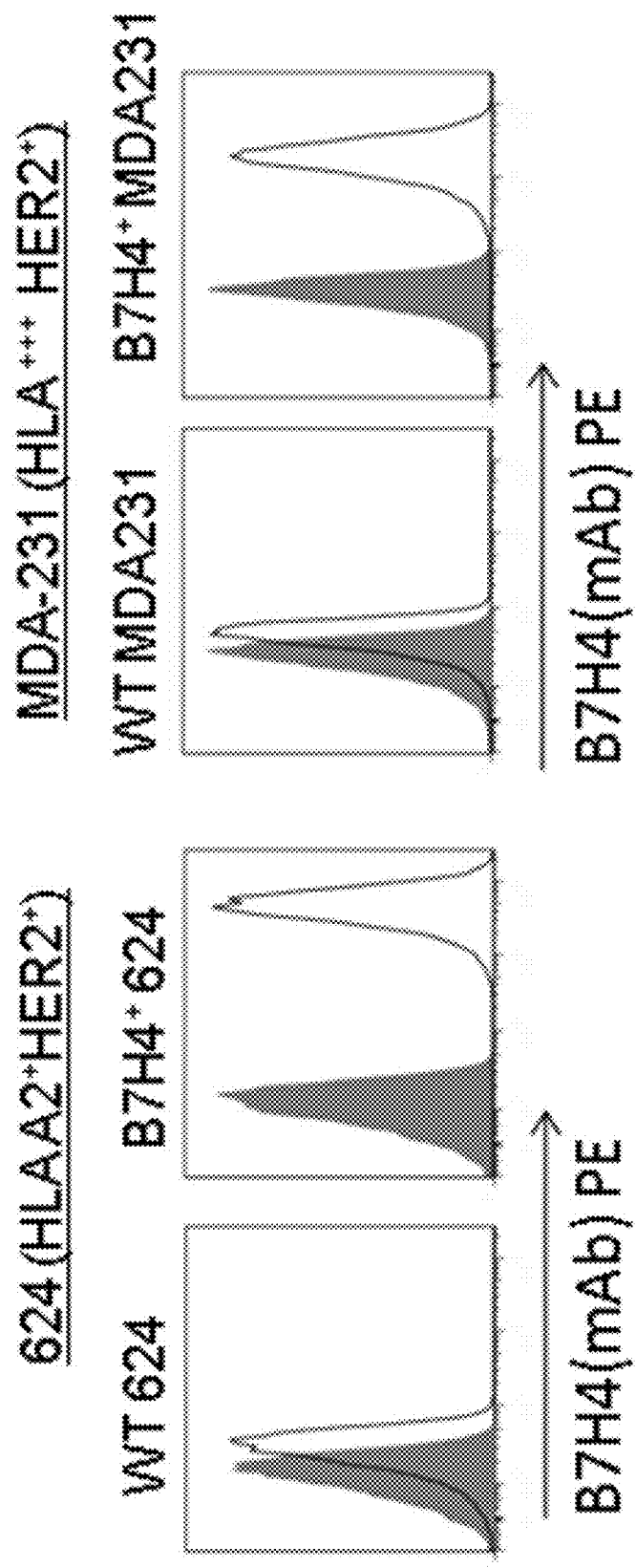
FIGS. 9A-9C are a series of images demonstrating that B7-H4$^+$ HER2$^+$ tumor cells inhibit HER2-TCR transduced T cell activation and anti-B7-H4 scFv 3#68 overcomes T cell inhibition.
Figure 9B:
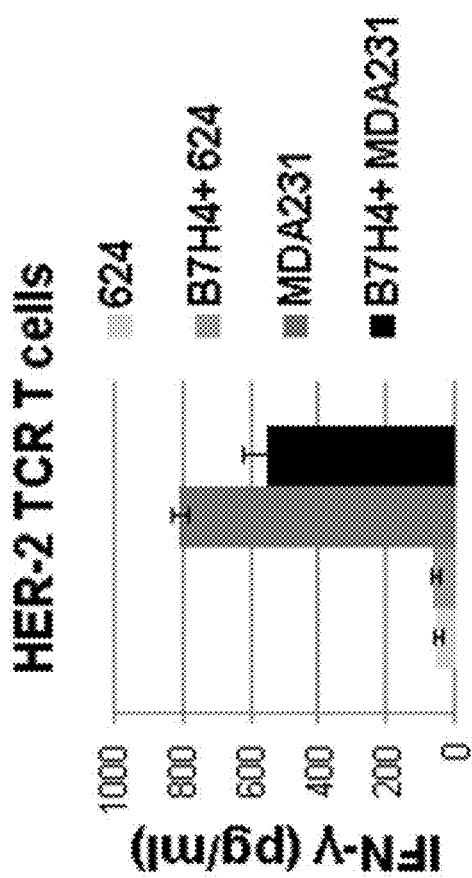
Figure 9C:
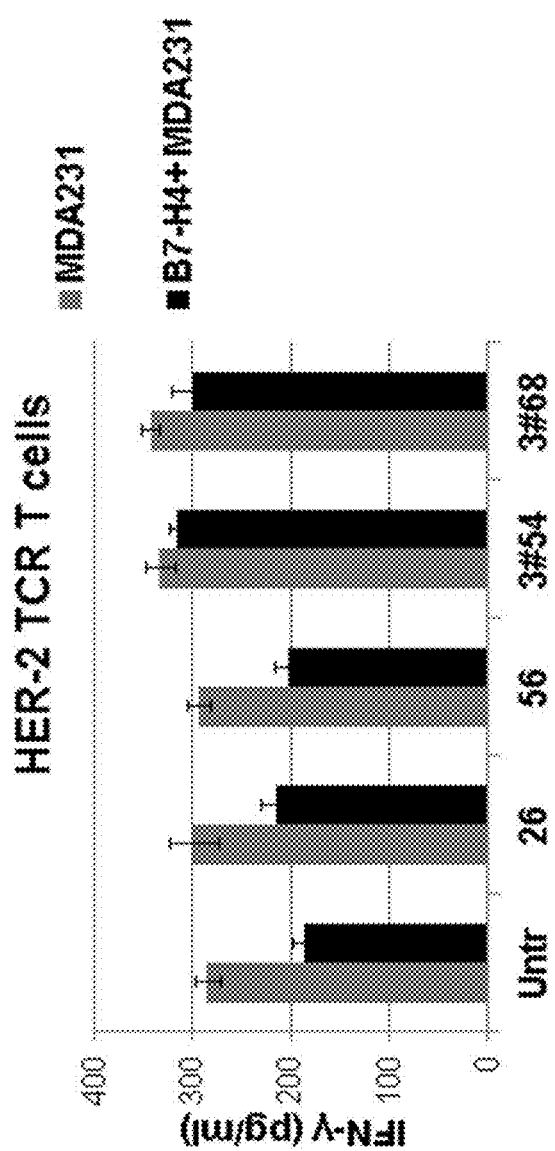

Antigen-Specific T Cell Activation is Inhibited by Tumor Cells Expressing B7-H4 and can be Restored by Anti-B7-H4 scFvs Since B7-H4 can also be expressed at the tumor cell surfaces (FIG. 5), experiments were designed to address whether B7-H4 expressed by tumor cells could inhibit antigen-specific T cell function. Full length B7-H4 was transduced in HER-2+/HLA-A2$^+$ MDA231 breast cancer cell line (positive target) and in HER-2$^+$/HLA-A2$^{low}$ 624 melanoma cell line (negative target) (FIG. 9A). These cell lines were assayed for recognition by HER-2 specific TCR T cells. HER-2 TCR T cells secreted IFN-γ in presence of HER-2 expressing tumor cells (MDA231, dark grey bar) but not in presence of HER-2 negative tumor cells (624, light grey bar). Furthermore, IFN-γ secretion was substantially inhibited in presence of B7-H4 transduced MDA231 cells (black bar; p=0.0451) (FIG. 9B). As previously observed, anti-B7-H4 scFvs 3#54 and 3#68 could completely restore IFN-γ secretion of HER-2 T cells, thus seemingly bypassing the inhibitory function of B7-H4 transduced MDA231 (p=0.4393 for scFv 3#54; p=0.2179 for scFv 3#68) (FIG. 9C). These results further corroborated with the hypothesis that blocking B7-H4 can overcome antigen-specific T cell inhibition mediated by B7-H4 expressed on tumor cell surface.

Figures 10A, 10B:
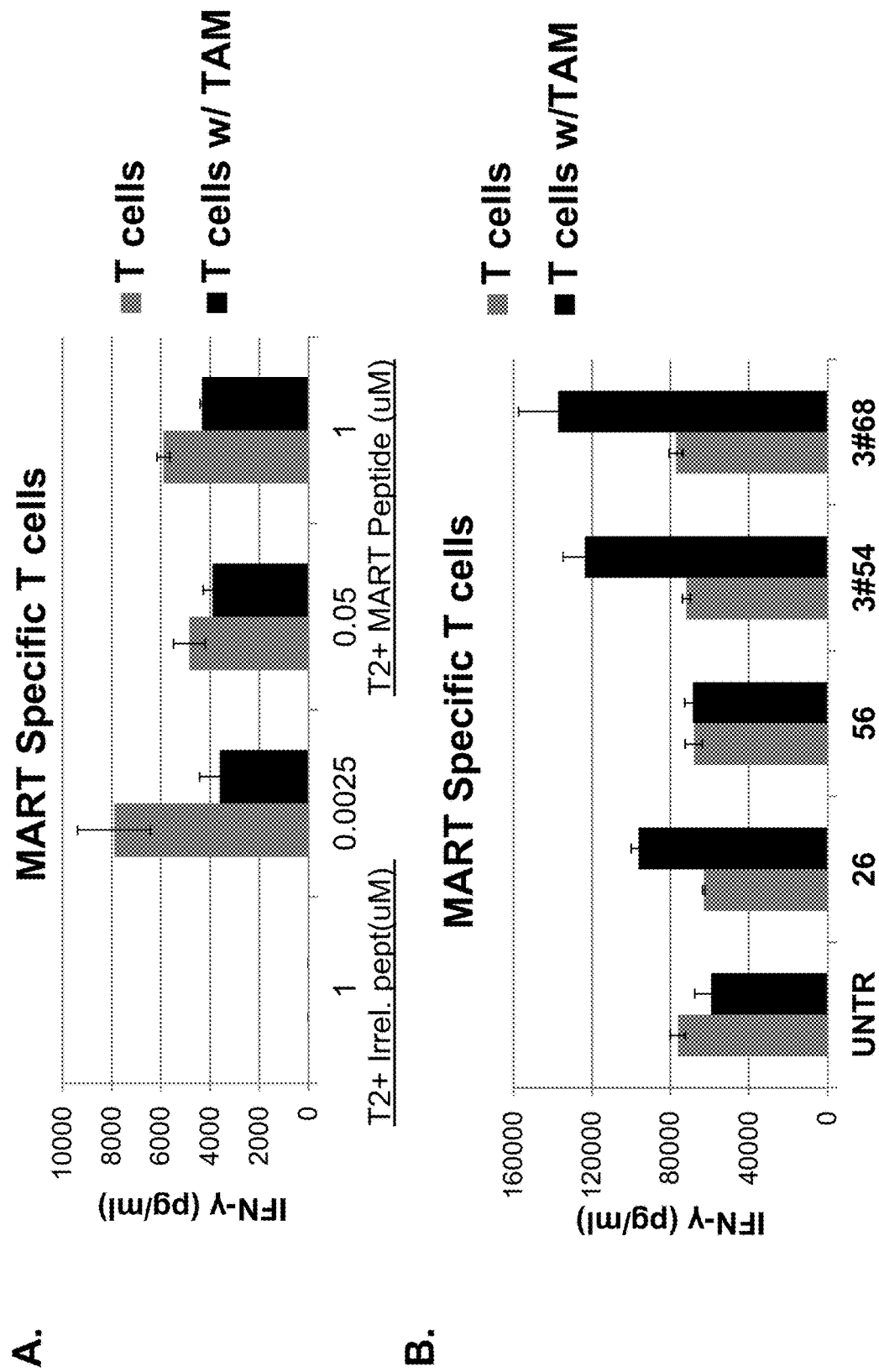
FIGS. 10A-10B are a series of images demonstrating that B7-H4 TAMs inhibit antigen-specific T cells and anti-B7-H4 scFvs reverse T cell inhibition.

Antigen-Specific T Cell Activation is Inhibited by B7-H4 Expressing Tumor-Polarized Macrophages in Presence of Peptide-Pulsed T2 APCs and can be Restored by Anti-B7-H4 scFvs Macrophages can be polarized towards TAMs by transwell co-culture with tumor cells via exchange of soluble factors (Dangaj et al., 2011, PLoS One 6(12):e28386; Hagemann et al., 2006, J Immunol 176(8):5023-32). Thus, to study the effect of B7-H4 expressed in trans by tumor-polarized macrophages, experiments were designed to set up transwell co-cultures of ovarian cancer cells and in vitro differentiated M1 macrophages. In vitro tumor-polarized macrophages expressed B7-H4 (FIGS. 11A-11C) and are referred herein as B7-H4+ TAMs. B7-H4+ TAMs were tested for their ability to inhibit MART-specific T cells stimulated with peptide-pulsed T2 APCs. Antigen-specific T cell responses were down-regulated in the presence of B7-H4+ TAMs pulsed with low concentrations of MART peptide (p=0.0$^{287}$ for 0.0025 μM) (FIG. 10A). Activation and proliferation of antigen-specific T cells as measured by CFSE staining and CD137 expression were more evidently reduced at low peptide concentration (0.0025 μM and 0.05 μM) (As previously observed, anti-B7-H4 scFvs 3#54 and 3#68 could completely restore IFN-γ secretion of HER-2 T cells, thus seemingly bypassing the inhibitory function of B7-H4 transduced MDA231 (p=0.4393 for scFv 3#54; p=0.2179 for scFv 3#68) (FIG. 9C). These results further corroborated with the hypothesis that blocking B7-H4 can overcome antigen-specific T cell inhibition mediated by B7-H4 expressed on tumor cell surface.). Anti-B7-H4 scFvs could reverse T cell inhibitory signals mediated by B7-H4+ TAMs. While anti-B7-H4 scFv #26 restored and significantly enhanced T-cell IFN-γ secretion by 1.5 fold (p=0.0144), anti-B7-H4 scFv 3#54 and 3#68 further enhanced T cell IFN-γ production by >2 folds (p=0.00$^{37}$ for scFv 3#54 and p=0.0061 for scFv 3#68) (FIG. 10B).

B7-H4-Based Targeted Therapy

B7-H4 expression in various types of human cancer tissues and correlation with advanced stages, poor patient survival, and tumor infiltration of T regulatory cells (Zang et al., 2007, Proc Natl Acad Sci USA, 104(49):19458-63), makes it a candidate of choice for targeted therapy. However, B7-H4 expression has been reported to be mainly intracellular for ovarian cancer cells (Kryczek et al., 2006, J Exp Med 203(4):871-81; Choi et al., 2003, J Immunol 171(9):4650-4), thus limiting targeted therapeutic strategies.

The results presented herein demonstrate that B7-H4 was present at the surface of Epcam+ cancer cells freshly harvested from ascites and solid tumors from ovarian cancer patients, as well as on tumor-infiltrating monocytes. Consistent with this observation, ovarian cancer xenografts developed from long term cultured ovarian cancer cell lines upregulated B7-H4 expression on freshly harvested tumors, and drastically downregulated it after short term in vitro culture. Without being bound to any particular theory, these results support the hypothesis that B7-H4 cell surface expression is regulated by environmental conditions, possibly because B7-H4 expression specifically enhances tumor cell ability to escape immune recognition in vivo, but might not be non-essential for cell survival in vitro (Pardoll, 2012, Nat Rev Cancer 12(4):252-64). One possible environmental condition able to trigger surface B7-H4 presentation may be hypoxic stress that is of common occurrence in the tumor microenvironment. However, hypoxic culture conditions did not upregulate B7-H4 cell-surface expression in any of the ovarian cancer cell lines tested, including OVCAR5. The cytokine milieu of the tumor microenvironment could be another possible mechanism and in fact, Chen et al. recently reported that macrophage-derived TNF-α induced B7-H4 cell-surface expression in mouse lung carcinoma (Chen et al., 2012, Cancer Lett 317(1):99-105).

The demonstration that B7-H4 is expressed at the cell surface of tumor and tumor-infiltrating cells opens a new paradigm for simultaneous immune-modulation of the tumor microenvironment and direct ovarian cancer cell eradication using B7-H4-based targeting. To isolate recombinant antibodies specific for human B7-H4, a novel yeast-display scFv library derived from B cells of human ovarian cancer ascites was constructed. Selected anti-B7-H4 scFvs were then evaluated for their functional ability to reverse B7-H4-mediated T cell inhibition, through rB7-H4 protein, B7-H4+ APCs or B7-H4+ tumor cells. The results presented herein demonstrate that the activation of tumor antigen-TCR specific T cells was inhibited by the presentation of B7-H4 in cis on APCs or on tumor cells, and in trans on tumor-polarized macrophages. These results confirmed that B7-H4 is a regulatory molecule engaged in negative signaling that impacts T cell anti-tumor responses. Furthermore, while B7-H4 transduced APCs impair the activation of antigen-specific T cells, tumor cells transduced to express cell surface B7-H4 can also significantly impair tumor antigen-specific T cell responses. In addition, the results presented herein demonstrate that B7-H4-mediated inhibition in cis or in trans could be partially reversed by anti-B7-H4 scFv clone 3#54 and fully restored by anti-B7-H4 scFv 3#68. In fact, in transwell cocultures including blockade with anti-B7-H4 scFv, MART-TCR specific T cell responses were not only restored in presence of TAMs but further enhanced. Without wishing to be bound to any particular theory, it is believed that in addition to blocking B7-H4, anti-B7-H4 also restored Th1 proinflammatory environment which could further polarize macrophages into an M1-like phenotype and stimulate antigen-specific T cells. Similar results were obtained when using HER-2 TCR specific T cells.

Two strategies were used to isolate the anti-B7-H4 scFvs, one representing the conventional enrichment of the yeast display library on soluble recombinant protein by magnetic and flow sortings and a second one where the yeast display scFv library was further enriched using cells differentially expressing surface B7-H4. Analysis of the scFv binding to recombinant B7-H4 by capture ELISA did not highlight differences between the differentially isolated scFv categories. However, when testing their functional ability to block B7-H4 mediated inhibition, the cell-based isolated scFvs showed superior blockade capacity. This may be due to the epitope each scFv recognizes which in case of scFv 3#68 could be identical with that of the putative B7-H4 ligand. It also strongly suggests that isolating scFvs by differential panning of the yeast-display scFv library on cells could permit access to epitopes that are not readily available in recombinant soluble antigens. In addition, the above approach might not be possible in the case of monoclonal antibody isolation since the host or hybridoma cells are immunized with soluble antigens.

The antibodies of the invention exhibit activities in blocking B7-H4 in vitro and their human sequence could avoid a potential HAMA response and possible inhibition by endogenous antibodies in vivo. Notably these recombinant antibodies have a smaller size than conventional antibodies favoring their potential binding to target cells expressing B7-H4 even in areas small penetration.

Targeting B7-H4 can simultaneously modify critical components of the tumor microenvironment, including tumor-associated macrophages, DCs and tumor cells. Blocking the inhibitory signals mediated by B7-H4 can potentiate T cell anti-tumor responses and could also decrease tumor endothelial T cell barrier because B7-H4 expression on tumor endothelial cells has also been observed in RCC tissues (Krambeck et al., 2006, Proc Natl Acad Sci USA 103(27):10391-6). Targeting immune checkpoint molecules such as CTLA-4 and PD-1 has elicited clinical results especially in patients with pre-existing immune responses. Ovarian cancer is a disease largely involving immune circuits that could predict better patient survival (Zhang et al., 2003, N Engl J Med 348(3):203-13) or poorer outcome (Kryczek et al., 2007, Cancer Res 67(18):8900-5; Curiel et al., 2004, Nat Med 10(9):942-9).

Example 3: B7-H4-Specific CAR

The following experiments were performed to validate a chimeric antigen receptor to redirect T-cells against B7-H4-expressing targets using the antibodies of the present invention.

B7-H4-Specific CAR Construction

Anti-B7H4 scFv clones #56, #26, 3#54, and 3#68 were selected to construct B7-H4-specific CAR for the reason of relative high antigen binding affinity among the identified scFvs. The lentiviral CAR-expressed vector presently used in the experiment has been optimized before (Carpenito, et al., 2009, Proc Natl Acad Sci USA 106:3360-3365) and constitute a CD8a hinge and transmembrane region, followed by a CD3ξ signaling moiety and in tandem with the CD28 intracellular signaling motif. The cDNA of the respective scFv was sub-cloned into these lentiviral-CAR vectors. Further, these vectors were transformed into 293T cells and western blot probed to CD3 confirmed successful expression by these vectors.

Figure 13:
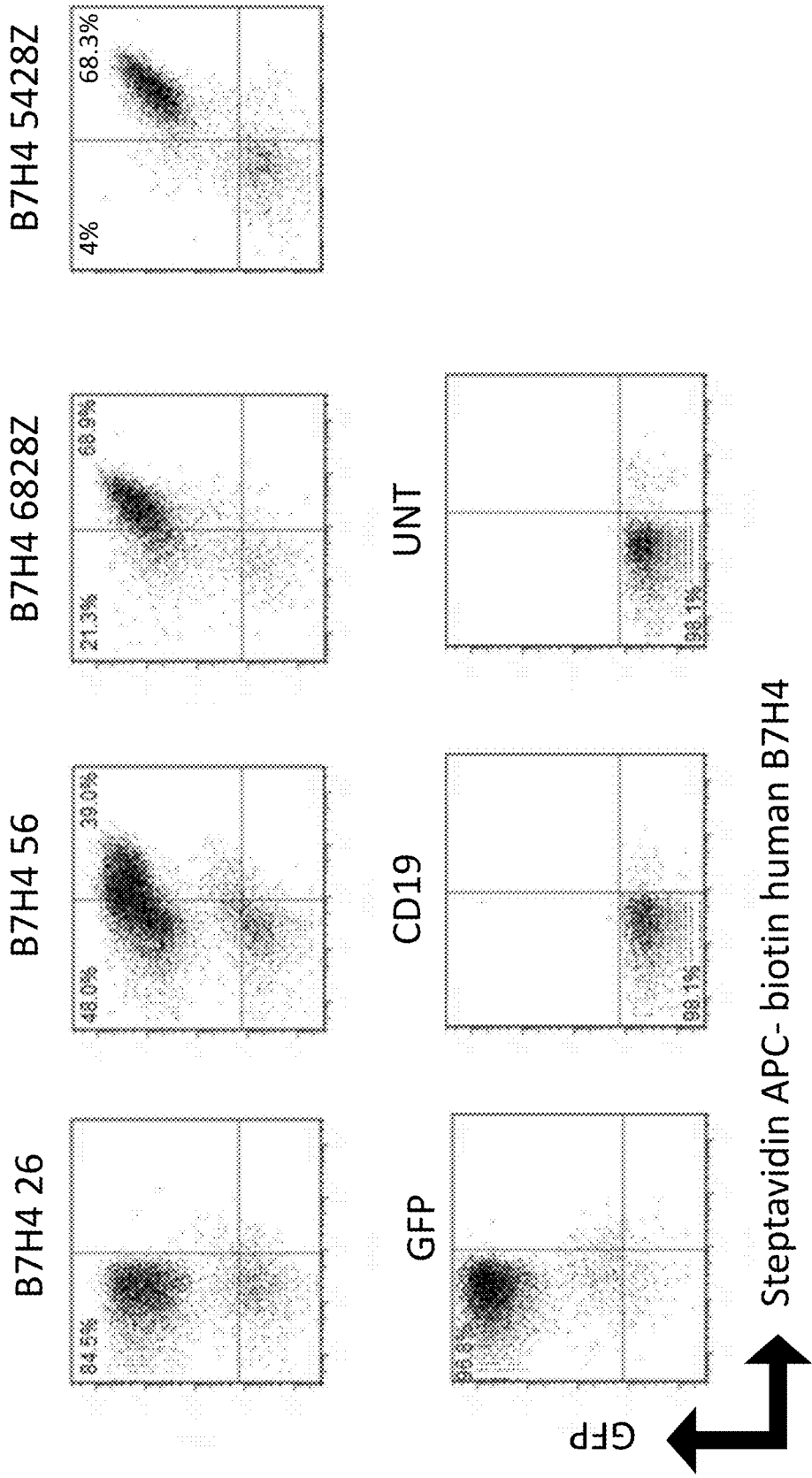
FIG. 13 is an image demonstrating that T cells bearing B7-H4 CARs comprised of scFvs bind human and recombinant B7-H4 with different affinity.
Figure 14:
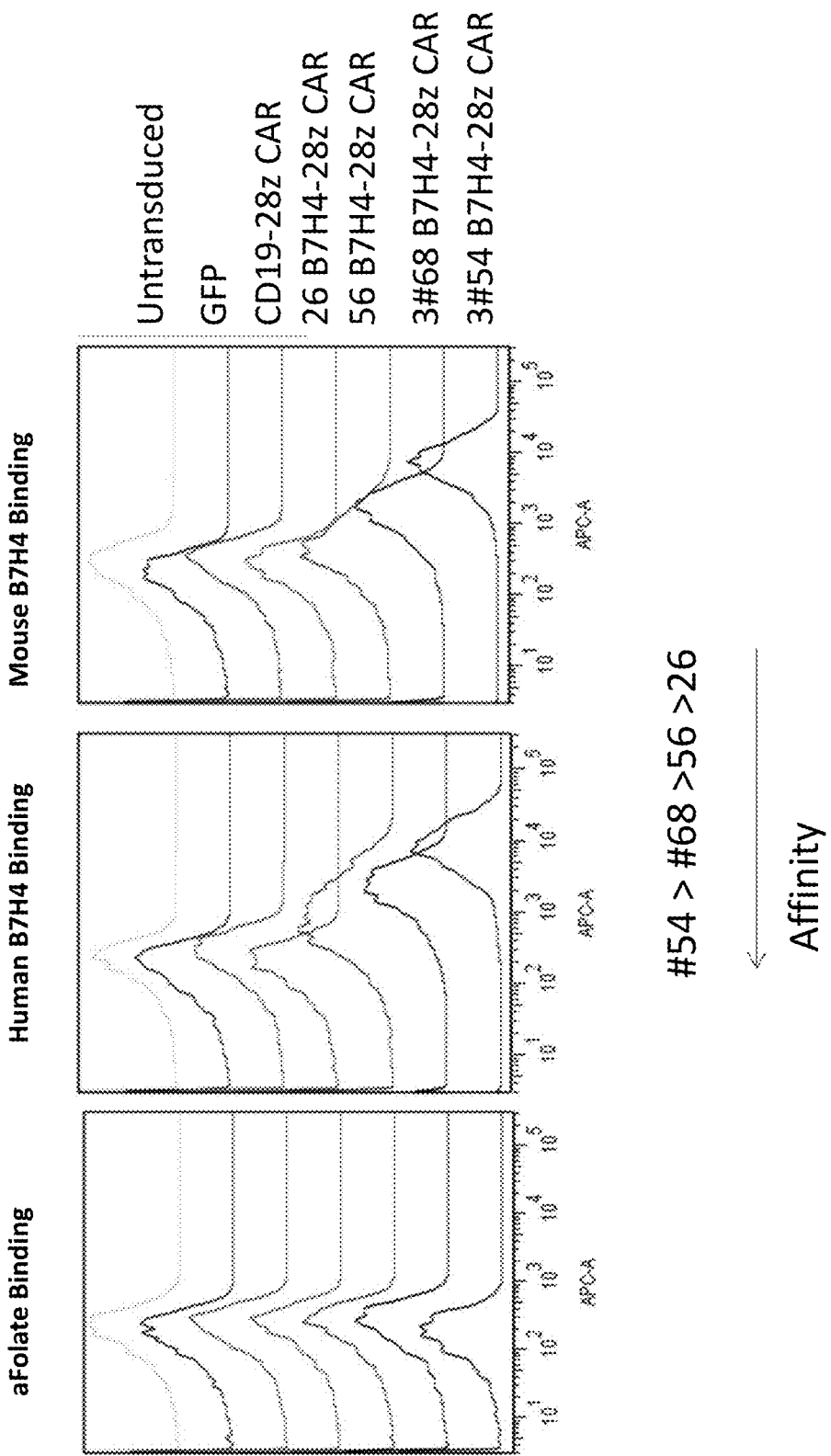
FIG. 14 is an image demonstrating that CARs bind both mouse and human B7-H4 proteins.

For effective lentiviral transduction, human T lymphocytes from peripheral blood were activated by CD3/CD28 beads. To test the transduction efficiency, T cells were transduced with GFP-expressed lentiviral vector, and the stable consistent GFP expression can be observed after 5 days transduction. FIG. 13 shows that creation of 4 anti-B7-H4 CARs of different binding affinities (Low to high 26, 56, 68, 54) in first or second generation constructs (+/− costim). CARs with different B7-H4 single chains exhibited varying affinity to human B7-H4 antigen. The B7-H4 CARs bind both mouse and human B7-H4 proteins (FIG. 14).

3E11-CAR+T Cells Showed B7-H4-Specific Cytotoxicity In Vitro

Figure 15A:
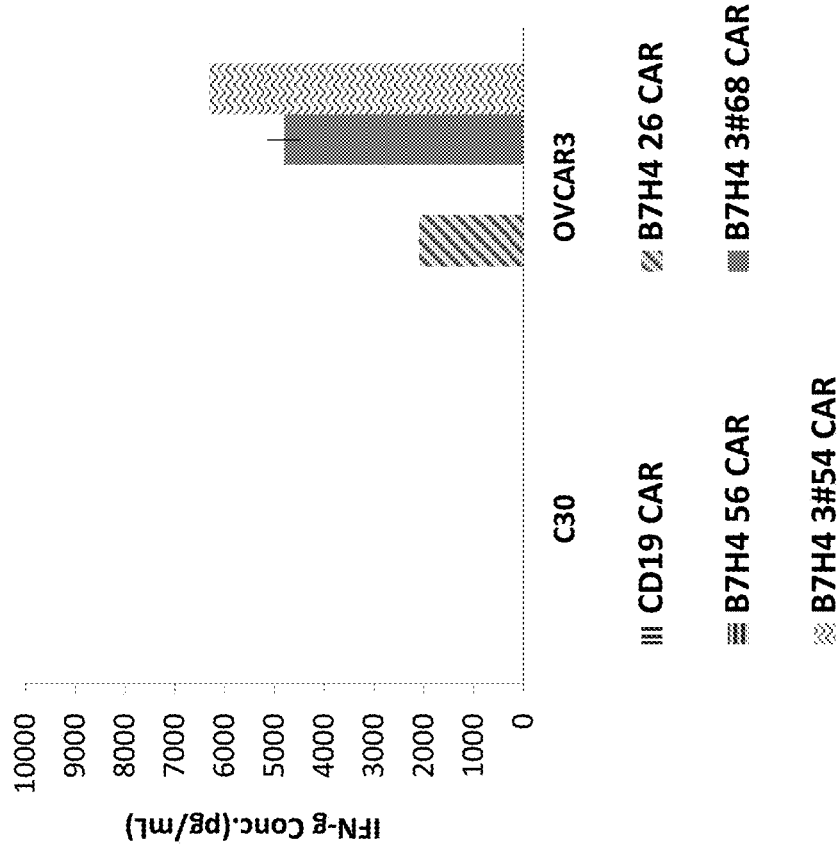
FIGS. 15A-15B are series of images demonstrating that T cells bearing B7-H4 CARs specifically react against B7H4+ cells.
Figure 15B:
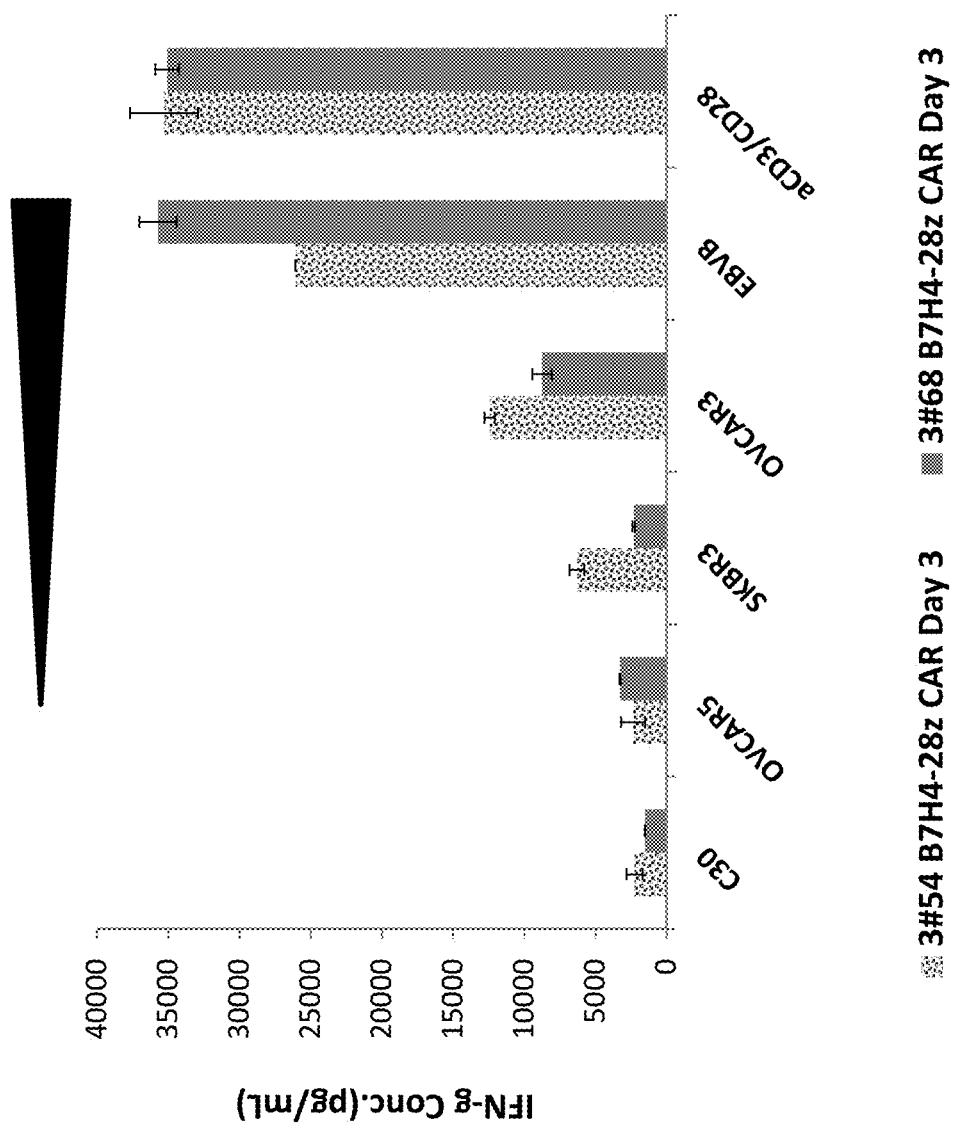

Engineered T cells were cocultured with B7-H4+ovarian cancer cells to determine the effects of antigen specific cytotoxicity. T cells were transduced by lentiviral vector of the respective B7-H4 scFv-28z (CD28 and CD3zeta) and applied to cytotoxicity assays as measured by the concentration of IFN-γ (FIGS. 15A-15B). As shown in FIG. 15A, T cells transduced with B7-H4-28z have significant cellular lysis of OVCAR3, while no lysis effects on CD19-28z transduced T cells. CARs 68, 54 and 26 reacted against a human cancer cell line expressing B7-H4 on the surface (A1847), but not against a B7-H4 negative line (c30) (FIG. 15A). FIG. 15B demonstrates that CAR 68 reacts against a variety of human cancer cells expressing B7-H4 on the surface. CAR 56 has low activity against an EBV cancer cell line.

These results demonstrate that the CAR transduced T cells can be used to target B7-H4 expressing tumors as a type of T cell-based immunotherapy of ovarian cancer. The results presented herein provide a specific and human-sourced scFv for CAR-transduced T cells-based immunotherapy.

Figure 16A:
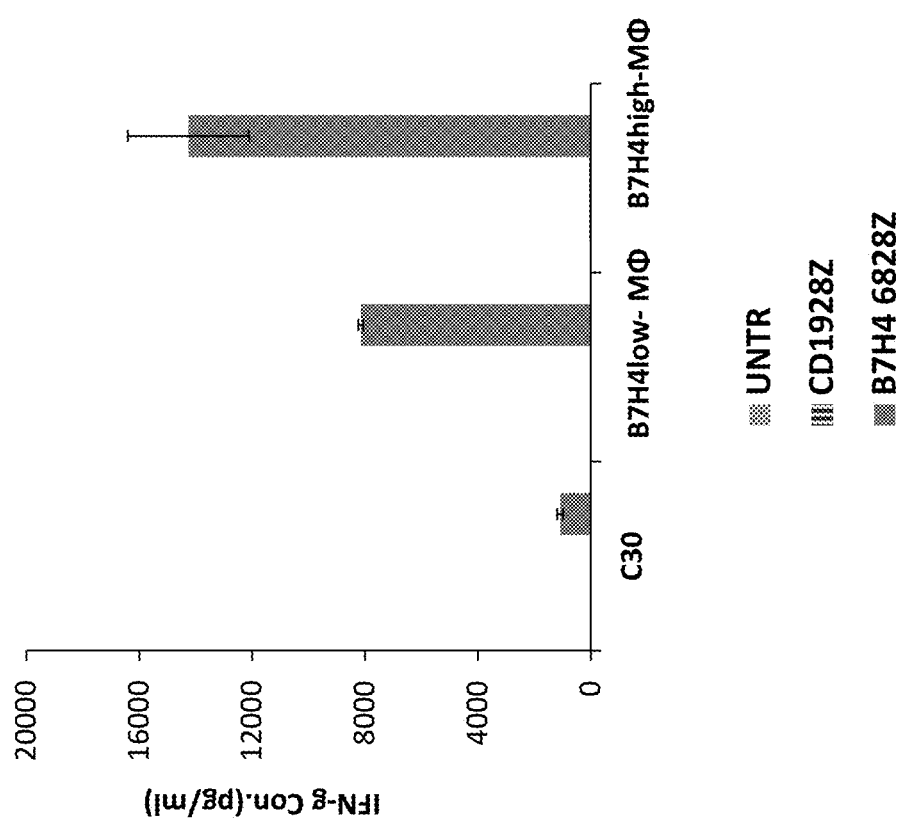
FIGS. 16A-16B are a series of images demonstrating the reactivity of B7-H4 CAR transduced T cells.

Experiments were conducted to assess whether B7H4 CAR transduced T cells are reactive against macrophages that express B7H4. FIG. 16A demonstrates that B7H4 CAR (e.g., 68-28z) transduced T cells are reactive against macrophages that express different levels of B7H4 as measured by the concentration of IFN-γ. CAR 68 reacted against human macrophages expressing high or low levels of surface B7-H4, and therefore are suited for targeting immunosuppressive tumor associated macrophages (TAMs).

Figure 16B:
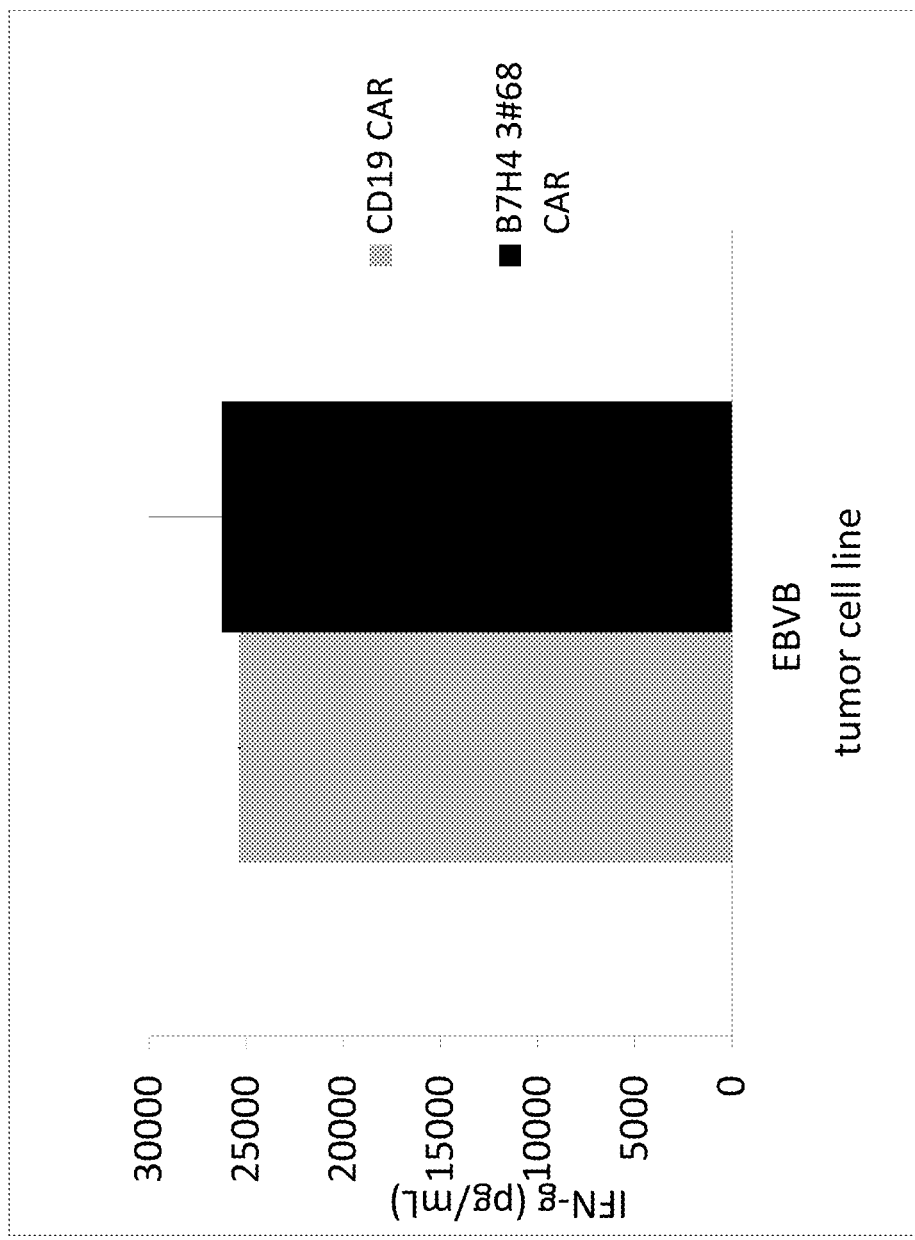

The results presented herein demonstrate that B7H4 CARs are able to respond to tumor cell lines expressing endogenous B7H4 antigen, including both solid and lymphoma cell lines. Most robust level of recognition was observed by 68 B7H4 CAR, comparable to well characterized CD19 CAR against B cell lymphoma cell line (FIG. 16B). B7H4 CARs also recognized macrophages expressing both low and high levels of B7H4, which can aid in reducing B7-H4+ tumor associated macrophages in the tumor microenvironment.

Figure 17A:
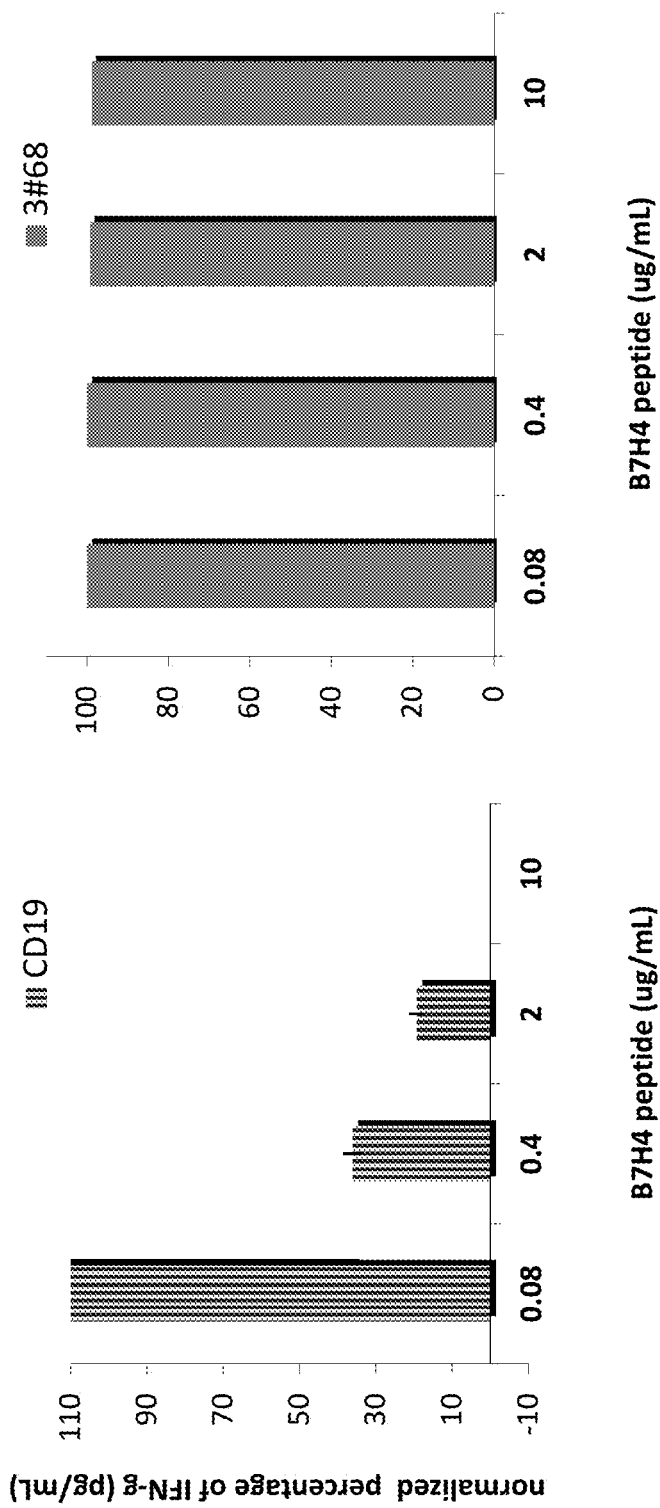
Figure 17B:
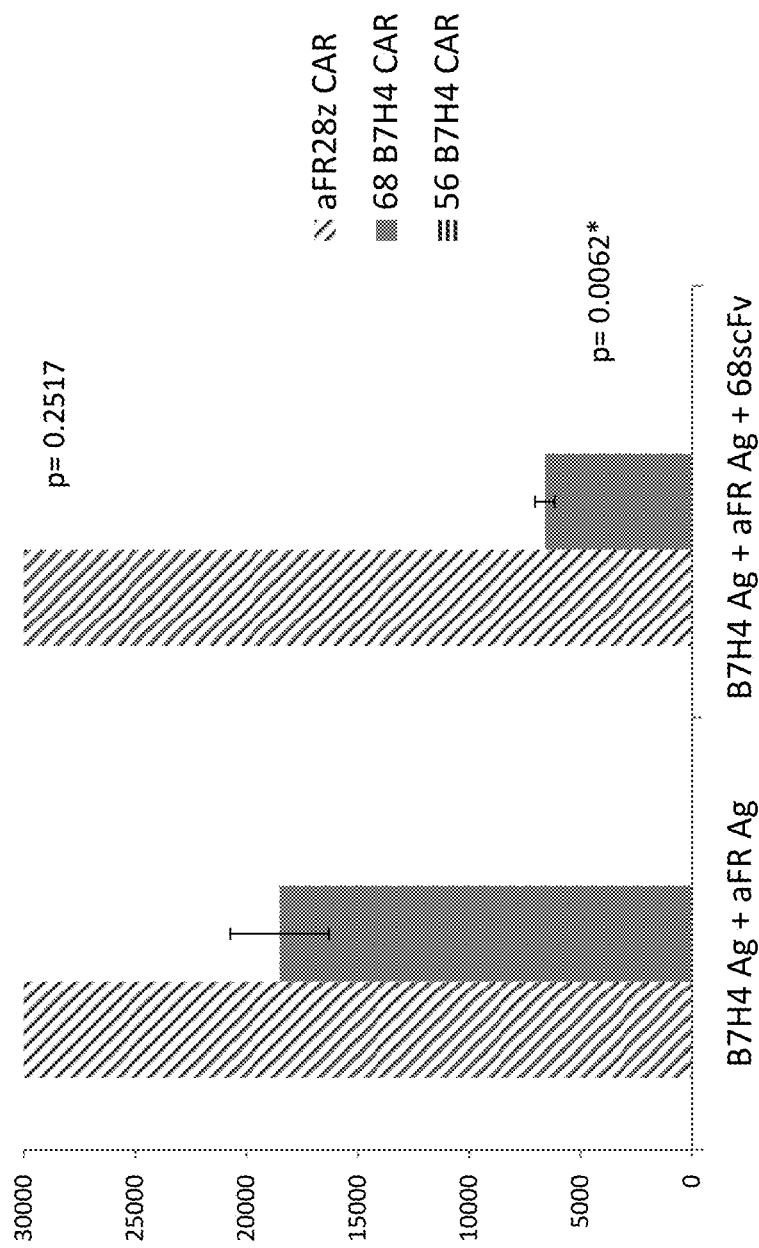
FIG. 17B is an image depicting that the addition of soluble #68scFv to the culture specifically inhibits #68 B7H4 CAR activity (IFNγ secretion) against immobilized B7-H4 protein, thus demonstrating the B7-H4 CAR is specifically blocked.

The next set of experiments was conducted to assess whether B7-H4 CARs can be inhibited by the addition of a corresponding B7-H4 scFv (FIG. 17A). All T cells were stimulated with anti-CD3 OKT-3 Ab (1 ug/mL) in the presence of increasing concentrations of B7-H4 protein. Values were normalized to anti-CD3 Ab plus control protein (folate receptor) at equivalent concentrations (**Normalized to IFN-γ % with OKT3+αFolate (irrelevant) Ag as 100% activity). Specific inhibition of 68 B7H4 CAR IFN-γ secretion was observed by the addition of 68scFv (FIG. 17B). It was also observed that 68 B7H4 CAR IFN-γ secretion in response to B7H4 Ag is not significantly reduced by B7H4 inhibitory signaling. CAR 68 T cells were found to be resistant to inhibition delivered by negative B7-H4 signals, whereas conventional (e.g., CD19 specific) CARs for other antigens are not.

Figure 18:
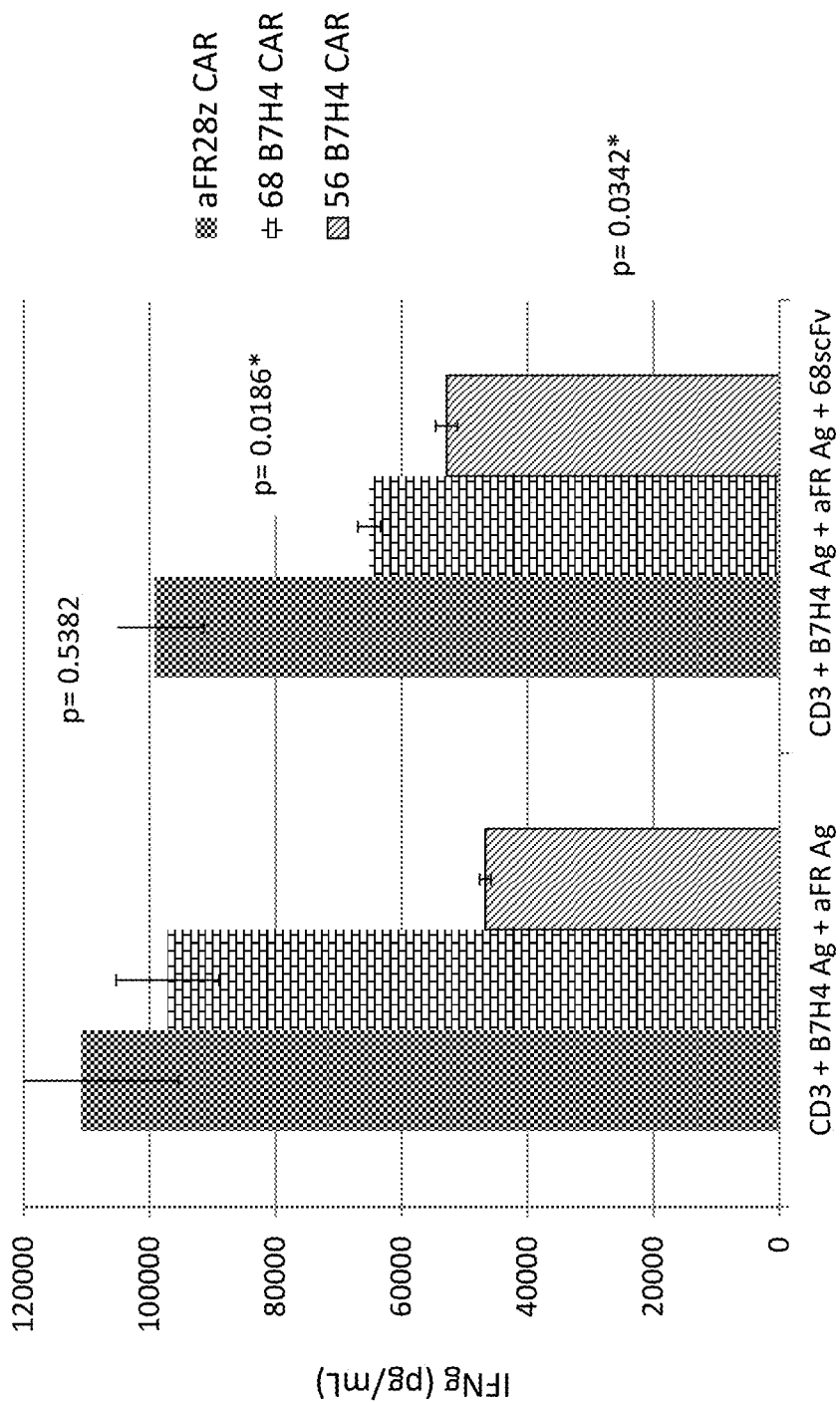
FIG. 18 is an image demonstrating that the addition of 68 scFv in the presence of CD3 leads to specific inhibition of 68 B7-H4 CAR IFN-γ secretion and specific moderate rescue of 56 B-7H4 CAR IFN-γ secretion.

Also, the addition of 68scFv in the presence of CD3 led to specific inhibition of 68 B7H4 CAR IFN-γ secretion and specific moderate rescue of 56 B7H4 CAR IFN-γ secretion (FIG. 18). For example, CAR 68 T cells were found to be specific for B7-H4 since their activity was blocked by pre-blocking B7-H4 with soluble anti-B7-H4 scFv 68 before culture).

It was also observed that 68scFv B7H4 CAR MIP1a cytokine secretion is not diminished as a result of B7H4 CAR-B7H4 Ag signaling (FIG. 19).

The results presented here demonstrate that 68 B7H4 CAR IFNγ and MIP1a secretion in response to B7H4 Ag is not significantly reduced by B7H4 inhibitory signaling; however, CARs of other specificity are. The addition of soluble #68scFv led to specific masking of B7-H4 and thus inhibited 68 B7H4 CAR IFNγ and MIP1a secretion.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of inhibiting B7-H4-dependent T cell inhibition, the method comprising contacting a cell with a human anti-B7-H4 antibody or fragment thereof, wherein the antibody or a fragment thereof comprises an amino acid sequence selected from the group consisting of SEQ ID NOs: 1-4.

2. The method of claim 1, wherein the cell is selected from the group consisting of a B7-H4-expressing tumor cell, a tumor-associated macrophage (TAM), and any combination thereof.

3. The method of claim 2, wherein the B7-H4-expressing tumor cell is an ovarian tumor cell.

4. A method of blocking T-cell inhibition mediated by a B7-H4-expressing cell and altering the tumor microenvironment to inhibit tumor growth in a mammal, the method comprising administering to the mammal an effective amount of a composition comprising an isolated anti-B7-H4 antibody or fragment thereof, wherein the antibody or a fragment thereof comprises an amino acid sequence selected from the group consisting of SEQ ID NOs: 1-4.

5. The method of claim 4, wherein the cell is selected from the group consisting of a B7-H4-expressing tumor cell, a tumor-associated macrophage (TAM), and any combination thereof.

6. The method of claim 5, wherein the B7-H4-expressing tumor cell is an ovarian tumor cell.

7. A method of inhibiting, suppressing or preventing immunosuppression of an anti-tumor or anti-cancer immune response in a mammal, the method comprising administering to the mammal an effective amount of a composition comprising an isolated anti-B7-H4 antibody or fragment thereof, wherein the antibody or a fragment thereof comprises an amino acid sequence selected from the group consisting of SEQ ID NOs: 1-4.

8. The method of claim 7, wherein the antibody or fragment thereof inhibits the interaction between a first cell with a T cell, wherein the first cell is selected from the group consisting of a B7-H4-expressing tumor cell, a tumor-associated macrophage (TAM), and any combination thereof.

9. The method of claim 8, wherein the B7-H4-expressing tumor cell is an ovarian tumor cell.

* * * * *

SEQUENCE LISTING

<160> NUMBER OF SEQ ID NOS: 22

<210> SEQ ID NO 1
<211> LENGTH: 263
<212> TYPE: PRT

-continued

<213> ORGANISM: Artificial
<220> FEATURE:
<223> OTHER INFORMATION: Chemically synthesized

<400> SEQUENCE: 1

```
Gln Pro Val Leu Thr Gln Ser His Ser Val Ser Glu Ser Pro Gly Lys
1               5                   10                  15

Thr Val Thr Ile Thr Cys Thr Gly Ser Gly Gly Asn Ile Ala Thr Gln
            20                  25                  30

Tyr Val Gln Trp Tyr Gln Arg Pro Gly Ser Gly Pro Thr Thr Val
        35                  40                  45

Ile Tyr Asp Asp Asp Gln Arg Pro Ser Gly Val Pro Asp Arg Phe Thr
50                  55                  60

Gly Ser Ile Asp Ser Ser Asn Ser Ala Ser Leu Thr Ile Ser Gly
65                  70                  75                  80

Leu Lys Thr Glu Asp Glu Ala Asp Tyr Tyr Cys Gln Ser Tyr Asp Ser
                85                  90                  95

Thr Asn His Gly Val Phe Gly Gly Gly Ala Lys Val Thr Val Leu Gly
            100                 105                 110

Gly Ser Ser Arg Ser Ser Ser Gly Gly Gly Ser Gly Gly Gly
            115                 120                 125

Gly Gln Val Gln Leu Gln Gln Trp Gly Pro Gly Leu Val Lys Pro Ser
130                 135                 140

Glu Thr Leu Ser Leu Thr Cys Thr Val Ser Gly Ser Ile Ser Ser
145                 150                 155                 160

Ser Ser Tyr Tyr Trp Gly Trp Ile Arg Gln Pro Pro Gly Lys Gly Leu
                165                 170                 175

Glu Trp Ile Gly Ser Ile Tyr Tyr Ser Gly Ser Thr Tyr Tyr Asn Pro
            180                 185                 190

Ser Leu Lys Ser Arg Val Thr Ile Ser Val Asp Thr Ser Lys Asn Gln
        195                 200                 205

Phe Ser Leu Lys Leu Ser Ser Val Thr Ala Ala Asp Thr Ala Val Tyr
210                 215                 220

Tyr Cys Ala Arg Leu Ser Lys Gly Tyr Ser Ser Ser Trp Ala Tyr Ser
225                 230                 235                 240

Tyr Tyr Gly Pro Asp Ala Trp Gly Gln Gly Thr Met Val Thr Val Ser
                245                 250                 255

Ser Phe Glu Gly Ser Glu Gln
            260
```

<210> SEQ ID NO 2
<211> LENGTH: 253
<212> TYPE: PRT
<213> ORGANISM: Artificial
<220> FEATURE:
<223> OTHER INFORMATION: Chemically synthesized

<400> SEQUENCE: 2

```
Asp Ile Val Met Thr Gln Thr Pro Ala Thr Leu Ser Val Ser Pro Gly
1               5                   10                  15

Lys Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Arg Arg Ala Thr Gly Ile Pro Asp Arg Phe Ser
50                  55                  60
```

```
Gly Ser Gly Ser Gly Thr Asp Phe Thr Leu Thr Ile Ser Ser Leu Gln
 65                  70                  75                  80

Ala Glu Asp Val Ala Val Tyr Tyr Cys Gln Gln Tyr Gly Ser Ser Pro
                 85                  90                  95

Arg Thr Phe Gly Gln Gly Thr Lys Leu Glu Ile Lys Gly Ser Ser
            100                 105                 110

Arg Ser Ser Ser Gly Gly Gly Ser Gly Gly Gly Gln Val
            115                 120                 125

Thr Leu Lys Glu Ser Gly Ala Glu Val Lys Asn Pro Gly Ser Ser Val
            130                 135                 140

Lys Val Ser Cys Lys Ala Ser Gly Gly Thr Phe Ser Ser Tyr Ala Ile
145                 150                 155                 160

Ser Trp Leu Arg Gln Ala Pro Gly Gln Gly Leu Glu Trp Met Gly Trp
                165                 170                 175

Ile Asn Pro Asn Ser Gly Gly Ser Asp Tyr Ala Gln Arg Phe Gln Gly
                180                 185                 190

Arg Val Thr Met Thr Arg Asp Thr Ser Ile Asn Thr Val Tyr Met Glu
            195                 200                 205

Leu Ser Arg Leu Arg Ser Asp Asp Thr Ala Val Tyr Tyr Cys Ala Arg
210                 215                 220

Val Glu Lys Arg Gly Tyr Tyr Tyr Gly Met Asp Val Trp Gly Gln Gly
225                 230                 235                 240

Thr Met Val Thr Val Ser Ser Phe Glu Gly Ser Glu Gln
                245                 250

<210> SEQ ID NO 3
<211> LENGTH: 254
<212> TYPE: PRT
<213> ORGANISM: Artificial
<220> FEATURE:
<223> OTHER INFORMATION: Chemically synthesized

<400> SEQUENCE: 3

Arg Pro Val Leu Thr Gln Pro Pro Ser Ala Ala Gly Thr Pro Gly Gln
 1               5                  10                  15

Arg Val Thr Ile Ser Cys Ser Gly Ser Ser Ser Asn Ile Gly Ser Asn
                 20                  25                  30

Tyr Val Tyr Trp Tyr Gln Gln Leu Pro Gly Met Ala Pro Lys Leu Leu
             35                  40                  45

Ile Tyr Thr Asn Asn Gln Arg Pro Ser Gly Val Pro Gly Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ala Trp Asp Asp Ser Leu
                 85                  90                  95

Asn Gly Trp Val Phe Gly Gly Gly Thr Glu Leu Thr Val Leu Gly Gly
            100                 105                 110

Ser Ser Arg Ser Ser Ser Ser Gly Gly Gly Ser Gly Gly Gly
            115                 120                 125

Gln Val Gln Leu Gln Glu Ser Gly Pro Gly Leu Val Lys Pro Ser Glu
130                 135                 140

Thr Leu Ser Leu Thr Cys Asn Val Ser Gly Arg Ser Val Ser Ser Gly
145                 150                 155                 160

Phe Tyr Trp Ser Trp Ile Arg Gln Arg Pro Gly Lys Gly Leu Glu Trp
                165                 170                 175
```

Val Gly Ser Ile Tyr Arg Ser Gly Leu Thr Tyr Tyr Asn Pro Ser Leu
            180                 185                 190

Lys Ser Arg Val Thr Ile Ser Val Asp Thr Ser Lys Asn Gln Phe Ser
            195                 200                 205

Leu Lys Leu Ser Ser Val Thr Ala Ala Asp Thr Ala Val Tyr Tyr Cys
            210                 215                 220

Ala Arg Ala Thr Pro Trp Tyr Tyr Gly Met Asp Val Trp Gly Gln
225                 230                 235                 240

Gly Thr Thr Val Thr Val Ser Ser Phe Glu Gly Ser Glu Gln
            245                 250

<210> SEQ ID NO 4
<211> LENGTH: 255
<212> TYPE: PRT
<213> ORGANISM: Artificial
<220> FEATURE:
<223> OTHER INFORMATION: Chemically synthesized

<400> SEQUENCE: 4

Gln Pro Gly Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Tyr Val Tyr Trp Tyr Gln Gln Phe Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Val Trp Val Phe Gly Gly Gly Thr Lys Val Thr Val Leu Gly Gly
            100                 105                 110

Ser Ser Arg Ser Ser Ser Ser Gly Gly Ser Gly Ser Gly Gly Gly Gly
            115                 120                 125

Gln Val Thr Leu Lys Glu Ser Gly Ala Glu Val Lys Asn Pro Gly Ser
        130                 135                 140

Ser Val Lys Val Ser Cys Lys Ala Ser Gly Gly Thr Phe Ser Ser Tyr
145                 150                 155                 160

Ala Ile Ser Trp Leu Arg Gln Ala Pro Gly Gln Gly Leu Glu Trp Met
                165                 170                 175

Gly Trp Ile Asn Pro Asn Ser Gly Gly Ser Asp Tyr Ala Gln Arg Phe
            180                 185                 190

Gln Gly Arg Val Thr Met Thr Arg Asp Thr Ser Ile Asn Thr Val Tyr
        195                 200                 205

Met Glu Leu Ser Arg Leu Arg Ser Asp Asp Thr Ala Val Tyr Tyr Cys
    210                 215                 220

Ala Arg Val Glu Lys Arg Gly Tyr Tyr Tyr Gly Met Asp Val Trp Gly
225                 230                 235                 240

Gln Gly Thr Met Val Thr Val Ser Ser Phe Glu Gly Ser Glu Gln
                245                 250                 255

<210> SEQ ID NO 5
<211> LENGTH: 789
<212> TYPE: DNA
<213> ORGANISM: Artificial
<220> FEATURE:

<223> OTHER INFORMATION: Chemically synthesized

<400> SEQUENCE: 5

```
cagcctgtgc tgactcagtc ccactctgtg tcggagtctc cggggaagac ggtaaccatc      60
acctgtaccg gcagcggtgg caacatcgcc acccaatatg tgcagtggta ccagcagcgc     120
ccgggcagtg gccccaccac tgtgatctat gacgatgacc aaaggccctc tggggtccct     180
gatcggttca ctggctccat cgacagttcc tccaactctg cctccctcac catctctgga     240
ctgaagactg aggacgaggc tgactactac tgtcagtctt atgatagcac caatcatggg     300
gtgttcggcg aggggccaa ggtcaccgtc ctaggcggat cctctaggtc aagttccagc     360
ggcggcggtg gcagcggagg cggcggtcag gtgcagctac agcagtgggg cccaggactg     420
gtgaagcctt cggagaccct gtccctcacc tgcactgtct ctggtggctc catcagcagt     480
agtagttact actgggggctg gatccgccag cccccaggga aggggctgga gtggattggg     540
agtatctatt atagtgggag cacctactac aacccgtccc tcaagagtcg agtcaccata     600
tcagtagaca cgtccaagaa ccagttctcc ctgaagctga gctctgtgac cgccgcggac     660
acggccgtgt attactgtgc gagactcagc aaggggtata gcagcagctg ggcctactcc     720
tactacggtc cggacgcctg gggccaaggg acaatggtca ccgtctcttc attcgaggga     780
tccgaacaa                                                              789
```

<210> SEQ ID NO 6
<211> LENGTH: 759
<212> TYPE: DNA
<213> ORGANISM: Artificial
<220> FEATURE:
<223> OTHER INFORMATION: Chemically synthesized

<400> SEQUENCE: 6

```
gatattgtga tgactcagac tccagccacc ctgtctgtgt ctccaggaa aagagccacc      60
ctctcctgca gggccagtca gagtgttagc agcaactact tagcctggta ccagcagaaa     120
cctggccagg ctcccaggct cctcatctat ggtgcatcca ggagggccac tggcatccca     180
gacaggttca gtggcagtgg gtctgggaca gacttcactc tcaccatcag cagcctgcag     240
gctgaagatg tggcagtttta ttactgtcag cagtatggta gctcacctcg acttttggc      300
caagggacca gctggagat caaaggcgga tcctctaggt caagttccag cggcggcggt     360
ggcagcggag gcggcggtca ggtcaccttg aaggagtctg gggctgaggt gaagaaccct     420
gggtcctcgg tgaaggtctc ctgcaaggct tctggaggca cttcagcag ctatgctatc      480
agctggctgc gacaggcccc tggacaaggg cttgagtgga tgggatggat caaccctaac     540
agtggtggct cagactatgc acagaggttt cagggcaggg tcaccatgac cagggacacg     600
tccatcaaca cagtctacat ggaactgagc aggctgagat ctgacgacac ggccgtctat     660
tactgtgcaa gagtggaaaa gaggggctac tattacggta tggacgtctg gggccaaggg     720
acaatggtca ccgtctcttc attcgaggga tccgaacaa                              759
```

<210> SEQ ID NO 7
<211> LENGTH: 762
<212> TYPE: DNA
<213> ORGANISM: Artificial
<220> FEATURE:
<223> OTHER INFORMATION: Chemically synthesized

<400> SEQUENCE: 7

```
cggcccgtgc tgactcagcc accctcagcg gctgggaccc ccgggcagag ggtcaccatc      60
```

-continued

```
tcttgttctg gaagcagctc aacatcgga agtaattatg tatattggta ccagcagctc    120
ccaggaatgg cccccaaact cctcatctat acgaataatc agcggccctc agggtccct    180 ggccgattct ctggctccaa gtctggcacc tcagcctccc tggccatcag tgggctccgg    240
tccgaggatg aggctgatta ttactgtgca gcatgggatg acagcctgaa tggttgggtg    300
ttcggcggag ggaccgagct gaccgtccta ggcggatcct ctaggtcaag ttccagcggc    360
ggcggtggca gcgaggcgg cggtcaggtg cagctgcagg agtcgggccc aggactggtg    420
aagccttcgg agaccctgtc cctcacctgc aatgtctccg gtcgttccgt cagcagtggt    480
ttctactgga gctggatccg gcagcgccca gggaaggggc tggagtgggt tggcagtatc    540
tatcgtagtg gactcactta ctacaacccg tccctcaaga gtcgagtcac catctcagtt    600
gacacgtcca agaaccagtt ctccctgaag ctgagctctg tgaccgctgc ggacacggcc    660
gtgtattact gtgcgagggc cacaccttgg tactactacg gtatggacgt ctggggccaa    720
gggaccacgg tcaccgtctc ctcattcgag ggatccgaac aa    762
```

<210> SEQ ID NO 8  
<211> LENGTH: 765  
<212> TYPE: DNA  
<213> ORGANISM: Artificial  
<220> FEATURE:  
<223> OTHER INFORMATION: Chemically synthesized

<400> SEQUENCE: 8

```
cagcctgggc tgactcagcc accctcagcg tctgggaccc ccgggcagag ggtcaccatc     60
tcttgttctg gaagcagctc aacatcgga agtaattatg tatactggta ccagcagttc    120
ccaggaacgg cccccaaact cctcatctat aggaataatc agcggccctc agggtccct    180 gaccgattct ctggctccaa gtctggcacc tcagcctccc tggccatcag tgggctccgg    240
tccgaggatg aggctgatta ttactgtgcg cgtgggatg acagcctgag tgtttgggtg    300
ttcggcggag ggaccaaggt caccgtccta ggcggatcct ctaggtcaag ttccagcggc    360
ggcagtggca gcgaggcgg cggtcaggtc accttgaagg agtctgggc tgaggtgaag    420 aaccctgggt cctcggtgaa ggtctcctgc aaggcttctg gaggcacctt cagcagctat    480
gctatcagct ggctgcgaca ggcccctgga caagggcttg agtggatggg atggatcaac    540
cctaacagtg gtggctcaga ctatgcacag aggtttcagg gcagggtcac catgaccagg    600
gacacgtcca tcaacacagt ctacatggaa ctgagcaggc tgagatctga cgacacggcc    660
gtctattact gtgcaagagt ggaaaagagg ggctactatt acggtatgga cgtctggggc    720
caagggacaa tggtcaccgt ctcttcattc gagggatccg aacaa    765
```

<210> SEQ ID NO 9  
<211> LENGTH: 231  
<212> TYPE: PRT  
<213> ORGANISM: Artificial  
<220> FEATURE:  
<223> OTHER INFORMATION: Chemically synthesized

<400> SEQUENCE: 9

Phe Gly Ile Ser Gly Arg His Ser Ile Thr Val Thr Thr Val Ala Ser
1               5                   10                  15

Ala Gly Asn Ile Gly Glu Asp Gly Ile Leu Ser Cys Thr Phe Glu Pro
            20                  25                  30

Asp Ile Lys Leu Ser Asp Ile Val Ile Gln Trp Leu Lys Glu Gly Val
        35                  40                  45

Leu Gly Leu Val His Glu Phe Lys Glu Gly Lys Asp Glu Leu Ser Glu
            50                  55                  60

Gln Asp Glu Met Phe Arg Gly Arg Thr Ala Val Phe Ala Asp Gln Val
 65                  70                  75                  80

Ile Val Gly Asn Ala Ser Leu Arg Leu Lys Asn Val Gln Leu Thr Asp
                85                  90                  95

Ala Gly Thr Tyr Lys Cys Tyr Ile Ile Thr Ser Lys Gly Lys Gly Asn
            100                 105                 110

Ala Asn Leu Glu Tyr Lys Thr Gly Ala Phe Ser Met Pro Glu Val Asn
        115                 120                 125

Val Asp Tyr Asn Ala Ser Ser Glu Thr Leu Arg Cys Glu Ala Pro Arg
    130                 135                 140

Trp Phe Pro Gln Pro Thr Val Val Trp Ala Ser Gln Val Asp Gln Gly
145                 150                 155                 160

Ala Asn Phe Ser Glu Val Ser Asn Thr Ser Phe Glu Leu Asn Ser Glu
                165                 170                 175

Asn Val Thr Met Lys Val Val Ser Val Leu Tyr Asn Val Thr Ile Asn
            180                 185                 190

Asn Thr Tyr Ser Cys Met Ile Glu Asn Asp Ile Ala Lys Ala Thr Gly
        195                 200                 205

Asp Ile Lys Val Thr Glu Ser Glu Ile Lys Arg Arg Ser His Leu Gln
    210                 215                 220

Leu Leu Asn Ser Lys Ala Ser
225                 230

<210> SEQ ID NO 10
<211> LENGTH: 693
<212> TYPE: DNA
<213> ORGANISM: Artificial
<220> FEATURE:
<223> OTHER INFORMATION: Chemically synthesized

<400> SEQUENCE: 10

```
tttggtattt cagggagaca ctccatcaca gtcactactg tcgcctcagc tgggaacatt      60
ggggaggatg gaatcctgag ctgcactttt gaacctgaca tcaaactttc tgatatcgtg     120
atacaatggc tgaaggaagg tgttttaggc ttggtccatg agttcaaaga aggcaaagat     180
gagctgtcgg agcaggatga aatgttcaga ggccggacag cagtgtttgc tgatcaagtg     240
atagttggca atgcctcttt gcggctgaaa acgtgcaac tcacagatgc tggcacctac      300
aaatgttata tcatcacttc taaaggcaag ggaatgcta accttgagta taaaactgga     360
gccttcagca tgccggaagt gaatgtggac tataatgcca gctcagagac cttgcggtgt     420
gaggctcccc gatggttccc ccagcccaca gtggtctggg catcccaagt tgaccaggga     480
gccaacttct cggaagtctc caataccagc tttgagctga actctgagaa tgtgaccatg     540
aaggttgtgt ctgtgctcta caatgttacg atcaacaaca catactcctg tatgattgaa     600
aatgacattg ccaaagcaac aggggatatc aaagtgacag aatcggagat caaaaggcgg     660
agtcacctac agctgctaaa ctcaaaggct tct                                  693
```

<210> SEQ ID NO 11
<211> LENGTH: 37
<212> TYPE: DNA
<213> ORGANISM: Artificial
<220> FEATURE:
<223> OTHER INFORMATION: Chemically synthesized

```
<400> SEQUENCE: 11
ggttctggtg gtggaggttc tggtggtggt ggatctg                        37

<210> SEQ ID NO 12
<211> LENGTH: 63
<212> TYPE: DNA
<213> ORGANISM: Artificial
<220> FEATURE:
<223> OTHER INFORMATION: Chemically synthesized

<400> SEQUENCE: 12
gagaccgagg agagggttag ggataggctt accgtcgacc aagtcttctt cagaaataag    60
ctt                                                             63

<210> SEQ ID NO 13
<211> LENGTH: 18
<212> TYPE: PRT
<213> ORGANISM: Artificial
<220> FEATURE:
<223> OTHER INFORMATION: Chemically synthesized

<400> SEQUENCE: 13

Gly Gly Ser Ser Arg Ser Ser Ser Gly Gly Gly Gly Ser Gly Gly
1               5                   10                  15

Gly Gly

<210> SEQ ID NO 14
<211> LENGTH: 54
<212> TYPE: DNA
<213> ORGANISM: Artificial
<220> FEATURE:
<223> OTHER INFORMATION: Chemically synthesized

<400> SEQUENCE: 14
ggtggttcct ctagatcttc ctcctctggt ggcggtggct cgggcggtgg tggg       54

<210> SEQ ID NO 15
<211> LENGTH: 33
<212> TYPE: DNA
<213> ORGANISM: Artificial
<220> FEATURE:
<223> OTHER INFORMATION: Chemically synthesized

<400> SEQUENCE: 15
ggtggtggag gttctggtgg tggtggatct gtc                            33

<210> SEQ ID NO 16
<211> LENGTH: 43
<212> TYPE: DNA
<213> ORGANISM: Artificial
<220> FEATURE:
<223> OTHER INFORMATION: Chemically synthesized

<400> SEQUENCE: 16
cgctgccacc gccgccgctg gaacttgacc tagaggatcc gcc                 43

<210> SEQ ID NO 17
<211> LENGTH: 44
<212> TYPE: DNA
<213> ORGANISM: Artificial
<220> FEATURE:
<223> OTHER INFORMATION: Chemically synthesized

<400> SEQUENCE: 17
```

```
ctaggtcaag ttccagcggc ggcggtggca gcggaggcgg cggt          44

<210> SEQ ID NO 18
<211> LENGTH: 39
<212> TYPE: DNA
<213> ORGANISM: Artificial
<220> FEATURE:
<223> OTHER INFORMATION: Chemically synthesized

<400> SEQUENCE: 18
gtcttcttca gaaataagct tttgttcgga tccctcgaa               39

<210> SEQ ID NO 19
<211> LENGTH: 67
<212> TYPE: DNA
<213> ORGANISM: Artificial
<220> FEATURE:
<223> OTHER INFORMATION: Chemically synthesized

<400> SEQUENCE: 19
ggttctggtg gtggaggttc tggtggtggt ggatctgagt ttggtatttc agggagacac   60
tccatca                                                             67

<210> SEQ ID NO 20
<211> LENGTH: 65
<212> TYPE: DNA
<213> ORGANISM: Artificial
<220> FEATURE:
<223> OTHER INFORMATION: Chemically synthesized

<400> SEQUENCE: 20
agaccgagga gagggttagg gataggctta ccgtcgacag aagcctttga gtttagcagc   60
tgtag                                                               65

<210> SEQ ID NO 21
<211> LENGTH: 35
<212> TYPE: DNA
<213> ORGANISM: Artificial
<220> FEATURE:
<223> OTHER INFORMATION: Chemically synthesized

<400> SEQUENCE: 21
acgctctaga atggcttccc tggggcagat cctct                   35

<210> SEQ ID NO 22
<211> LENGTH: 35
<212> TYPE: DNA
<213> ORGANISM: Artificial
<220> FEATURE:
<223> OTHER INFORMATION: Chemically synthesized

<400> SEQUENCE: 22
acgcgtcgac ttattttagc atcaggtaag ggctg                   35
```